(12) United States Patent
Tolan et al.

(10) Patent No.: US 10,662,455 B2
(45) Date of Patent: May 26, 2020

(54) SULFUR DIOXIDE AND/OR SULFUROUS ACID PRETREATMENT

(71) Applicant: Iogen Corporation, Ottawa (CA)

(72) Inventors: Jeffrey S. Tolan, Ottawa (CA); Daniel G. MacDonald, Ottawa (CA); Kristin Martens, Ottawa (CA); Natacha Leduc, Ottawa (CA); Brian Foody, Ottawa (CA)

(73) Assignee: Iogen Corporation, Ottawa, ON (CA)

( * ) Notice: Subject to any disclaimer, the term of this patent is extended or adjusted under 35 U.S.C. 154(b) by 179 days.

(21) Appl. No.: 16/061,254

(22) PCT Filed: Sep. 16, 2016

(86) PCT No.: PCT/CA2016/051088
§ 371 (c)(1),
(2) Date: Jun. 11, 2018

(87) PCT Pub. No.: WO2017/100907
PCT Pub. Date: Jun. 22, 2017

(65) Prior Publication Data
US 2018/0363017 A1  Dec. 20, 2018

Related U.S. Application Data

(60) Provisional application No. 62/269,339, filed on Dec. 18, 2015, provisional application No. 62/293,481, filed on Feb. 10, 2016, provisional application No. 62/364,219, filed on Jul. 19, 2016.

(30) Foreign Application Priority Data

Mar. 16, 2016 (WO) ................ PCT/CA2016/050291

(51) Int. Cl.
| | |
|---|---|
| *C12P 19/02* | (2006.01) |
| *C12P 19/14* | (2006.01) |
| *C13K 1/02* | (2006.01) |
| *C12P 7/10* | (2006.01) |
| *C12M 1/00* | (2006.01) |
| *D21C 1/04* | (2006.01) |
| *C13K 13/00* | (2006.01) |
| *B01D 3/06* | (2006.01) |

(52) U.S. Cl.
CPC ............ *C12P 19/02* (2013.01); *C12M 45/06* (2013.01); *C12M 45/09* (2013.01); *C12P 7/10* (2013.01); *C12P 19/14* (2013.01); *C13K 1/02* (2013.01); *C13K 13/002* (2013.01); *D21C 1/04* (2013.01); *B01D 3/06* (2013.01); *C12P 2201/00* (2013.01); *Y02E 50/16* (2013.01)

(58) Field of Classification Search
CPC ....... C12P 19/02; C12P 19/14; C12P 2201/00; C12P 7/10; C12P 2203/00; C12P 7/14; Y02E 50/16; C12M 45/09; C12M 45/06; C12M 45/03; C12M 45/20; C13K 1/02; C13K 13/002; D21C 1/04; D21C 1/02; D21C 3/06; B01D 3/06; B01D 2251/60; B01D 2252/10; B01D 2252/102; B01D 2257/302; B01D 53/002; B01D 53/1481; B01D 53/501; C12Y 302/01004; C10L 1/02

See application file for complete search history.

(56) References Cited

U.S. PATENT DOCUMENTS

| | | |
|---|---|---|
| 2,418,167 A | 4/1947 | Du Bois |
| 4,461,648 A | 7/1984 | Foody |
| 5,424,417 A | 6/1995 | Torget et al. |
| 5,789,210 A | 8/1998 | Ho et al. |
| 5,866,382 A | 2/1999 | Hallborn et al. |
| 6,475,768 B1 | 11/2002 | Otero et al. |
| 6,582,944 B1 | 6/2003 | Hallborn et al. |
| 7,527,927 B1 | 5/2009 | Ho et al. |
| 7,527,951 B2 | 5/2009 | Londesborough et al. |
| 7,622,284 B2 | 11/2009 | Op Den Camp et al. |
| 8,038,842 B2 | 10/2011 | Retsina et al. |
| 8,268,125 B2 | 9/2012 | Retsina et al. |
| 8,409,836 B2 | 4/2013 | Vehmaanpera et al. |
| 8,709,770 B2 | 4/2014 | Harlick et al. |
| 8,728,243 B2 | 5/2014 | Van Der Meulen et al. |
| 8,815,499 B2 | 8/2014 | Alriksson et al. |

(Continued)

FOREIGN PATENT DOCUMENTS

| | | |
|---|---|---|
| EP | 0 450 430 B1 | 10/1991 |
| EP | 0 715 657 B1 | 6/1996 |

(Continued)

OTHER PUBLICATIONS

Behera et al., "Importance of chemical pretreatment for bioconversion of lignocellulosic biomass" 2014, Renewable and Sustainable Energy Reviews, pp. 91-106, vol. 36.

Bensah, E. and Mensah, M., "Chemical Pretreatment Methods for the Production of Cellulosic Ethanol: Technologies and Innovations," International Journal of Chemical Engineering, 2013, pp. 1-21, vol. 2013.

Bhalla et al., "Improved lignocellulose conversion to biofuels with thermophilic bacteria and thermostable enzymes," Bioresource Technology, 2013, pp. 751-759, vol. 128.

(Continued)

*Primary Examiner* — Deborah K Ware
(74) *Attorney, Agent, or Firm* — Knobbe Martens Olson & Bear LLP

(57) ABSTRACT

A process for producing alcohol from lignocellulosic biomass includes adding at least one of sulfur dioxide and sulfurous acid to the lignocellulosic biomass to provide an effective sulfur dioxide dosage and/or effective sulfur dioxide slurry concentration, each of which is calculated using the ratio of the volume of the slurry in the pretreatment reactor to the total volume of the pretreatment reactor, within a predetermined range.

23 Claims, 12 Drawing Sheets

(56) References Cited

U.S. PATENT DOCUMENTS

| | | | |
|---|---|---|---|
| 8,834,633 | B2 | 9/2014 | Van Der Meulen et al. |
| 8,871,475 | B2 | 10/2014 | Alriksson et al. |
| 9,012,188 | B2 | 4/2015 | Van Heiningen et al. |
| 9,090,915 | B2 | 7/2015 | Wang et al. |
| 9,102,951 | B2 | 8/2015 | Griffin et al. |
| 9,284,382 | B2 | 3/2016 | Chen et al. |
| 9,290,821 | B2 | 3/2016 | Blackbourn et al. |
| 9,574,212 | B2 | 2/2017 | Foody et al. |
| 2005/0244934 | A1* | 11/2005 | Foody .................. B01B 1/005 435/101 |
| 2006/0068475 | A1* | 3/2006 | Foody .................. C12P 7/10 435/105 |
| 2009/0118477 | A1 | 5/2009 | Hallberg et al. |
| 2010/0056774 | A1 | 3/2010 | Anand et al. |
| 2010/0279361 | A1 | 11/2010 | South et al. |
| 2011/0300586 | A1 | 12/2011 | Liu et al. |
| 2012/0041186 | A1 | 2/2012 | Pschorn et al. |
| 2013/0071903 | A1 | 3/2013 | Rowland et al. |
| 2014/0053827 | A1 | 2/2014 | Macedo Baudel et al. |
| 2014/0154746 | A1 | 6/2014 | Jonsson et al. |
| 2014/0163210 | A1 | 6/2014 | Retsina et al. |
| 2014/0178944 | A1 | 6/2014 | Parekh et al. |
| 2014/0182582 | A1 | 7/2014 | Retsina et al. |
| 2014/0186899 | A1 | 7/2014 | Retsina et al. |
| 2014/0186903 | A1* | 7/2014 | Retsina .................. C07C 51/09 435/126 |
| 2015/0259709 | A1 | 9/2015 | Retsina et al. |
| 2016/0312249 | A1* | 10/2016 | Foody .................. C12M 45/20 |
| 2018/0037862 | A1* | 2/2018 | Foody .................. C12M 45/20 |
| 2018/0037863 | A1* | 2/2018 | Foody .................. C12M 45/03 |
| 2019/0194697 | A1* | 6/2019 | Dechman .............. C12P 19/02 |

FOREIGN PATENT DOCUMENTS

| | | |
|---|---|---|
| WO | WO 2002/070753 A3 | 9/2002 |
| WO | WO 2006/026863 A1 | 3/2006 |
| WO | WO 2006/034590 A1 | 4/2006 |
| WO | WO 2006/034591 A1 | 4/2006 |
| WO | WO 2006/128304 A1 | 12/2006 |
| WO | WO 2008/041840 A1 | 4/2008 |
| WO | WO 2009/026722 A1 | 3/2009 |
| WO | WO 2010/022511 A1 | 3/2010 |
| WO | WO 2013/113579 A1 | 8/2013 |
| WO | WO 2014/106222 A2 | 7/2014 |
| WO | WO 2016/145527 A1 | 9/2016 |
| WO | WO 2016/145528 A1 | 9/2016 |
| WO | WO 2016/145529 A1 | 9/2016 |
| WO | WO 2016/145531 A1 | 9/2016 |
| WO | WO 2017/136915 A1 | 8/2017 |

OTHER PUBLICATIONS

Boussaid et al., "Fermentability of the Hemicellulose-Derived Sugars from Steam-Exploded Softwood (Douglas Fir)," Biotechnology and Bioengineering, 1999, pp. 284-289, vol. 64, No. 3.
Brownell, H. and Saddler, J., "Steam Pretreatment of Lignocellulosic Material for Enhanced Enzymatic Hydrolysis," Biotechnology and Bioengineering, 1987, pp. 228-235, vol. 29.
Bura et al., "Influence of Xylan on the Enzymatic Hydrolysis of Steam-Pretreated Corn Stover and Hybrid Poplar," Biotechnol Prog, 2009, pp. 315-322, vol. 25, No. 2.
Bura et al., "Moving towards commercialization of lignocellulosic biomass to fuels to chemicals. How to deal with heterogeneous biomass?" University of Washington Biofuels and Bioproducts Laboratory, 2012.
Bura et al., "Optimization of SO2-Catalyzed Steam Pretreatment of Corn Fiber for Ethanol Production", Applied Biochemistry and Biotechnology, 2003, vol. 105-108, pp. 319-335.
Bura et al., "SO2-Catalyzed Steam Explosion of Corn Fiber for Ethanol Production," Applied Biochemistry and Biotechnology, 2002, pp. 59-72, vols. 98-100.
Carrasco et al., "SO2-catalysed steam pretreatment of quinoa stalks," J Chem Technol Biotechnol, 2015, pp. 64-71, vol. 90.

Carrasco et al., "SO2-catalyzed steam pretreatment and fermentation of enzymatically hydrolyzed sugarcane bagasse," Enzyme and Microbial Technology, 2010, pp. 64-73, vol. 46.
Carrasco, "Arabinosylated phenolics obtained from SO2-steam-pretreated sugarcane bagasse," Journal of Chemical Technology and Biotechnology, 2012, pp. 1723-1726, vol. 87.
Chacha et al., "Steam Pretreatment of Pine (*Pinus patula*) Wood Residue for the Production of Reducing Sugars," Cellulose Chemistry and Technology, 2011, pp. 495-501, vol. 45 (7-8).
Chandra et al., "Enhancing Hemicellulose Recovery and the Enzymatic Hydrolysis of Cellulose by Adding Lignosulfonates during the Two-Stage Steam Pretreatment of Poplar," ACS Sustainable Chem Eng, 2015, pp. 986-991, vol. 3.
Cheng et al., "High titer and yield ethanol production from undetoxified whole slurry of Douglas-fir forest residue using pH profiling in SPORL," Biotechnology for Biofuels, 2015, pp. 1-10, vol. 8:22.
Clark et al., "Steam Explosion of the Softwood Pinus Radiata with Sulphur Dioxide Addition. II. Process Characterisation," Journal of Wood Chemistry and Technology, 1989, pp. 135-166, vol. 9:2.
Clark et al., "Steam Explosion of the Softwood Pinus Radiata with Sulphur Dioxide Addition. I. Process Optimization," Journal of Wood Chemistry and Technology, 1987, pp. 373-403, vol. 7:3.
Corrales et al., "Structural evaluation of sugar cane bagasse steam pretreated in the presence of CO2 and SO2," Biotechnology for Biofuels, 2012, pp. 1-8, vol. 5:36.
De Bari et al., "SO2-Catalyzed Steam Fractionation of Aspen Chips for Bioethanol Production: Optimization of the Catalyst Impregnation," Ind. Eng. Chem. Res, 2007, pp. 7711-7720, vol. 46.
Dekker, R.F.H. et al., "Enzymic Saccharification of Sugarcane Bagasse Pretreated by Autohydrolysis-Steam Explosion," Biotechnology and Bioengineering, 1983, pp. 3027-3048, vol. XXV.
Dekker, Robert F. H., "The Utilization of Autohydrolysis-Exploded Hardwood (*Eucalyptus regnans*) and Softwood (*Pinus radiata*) Sawdust for the Production of Cellulolytic Enzymes and Fermentable Substrates," Biocatalysis, 1987, pp. 63-75, vol. 1.
Ehsanipour, Mandana, "Bioconversion of lignocellulosic hydrolysate to acetic acid using Moorella thermoacetica," a thesis submitted in partial fulfillment of the requirements for the degree of Master of Science at University of Washington, 2015.
Eklund et al., "The Influence of SO2 and H2SO4 Impregnation of Willow Prior to Steam Pretreatment," 1995, Bioresource Engineering, pp. 225-229, vol. 52.
Elander et al., "Summary of findings from the Biomass Refining Consortium for Applied Fundamentals and Innovation (CAFI): corn stover pretreatment," 2009, Cellulose, pp. 649-659, vol. 16.
Ewanick et al., "The effect of biomass moisture content on bioethanol yields from steam pretreated switchgrass and sugarcane bagasse," 2011, Bioresource Technology, pp. 2651-2658, vol. 102.
Fan et al., "Optimization of SO2-catalyzed hydrolysis of corncob for xylose and xylitol production," 2014, J Chem Technol Biotechnol, pp. 1720-1726, vol. 89.
Galbe et al., "A review of the production of ethanol from softwood," 2002, Appl Microbial Biotechnol, pp. 618-628, vol. 59.
Garlock et al., "Comparative material balances around pretreatment technologies for the conversion of switchgrass to soluble sugars," 2011, Bioresource Technology, pp. 11063-11071, vol. 102.
Gregg et al., "A Techno-Economic Assessment of the Pretreatment and Fractionation Steps of a Biomass-to-Ethanol Process," 1996, Applied Biochemistry and Biotechnology, pp. 711-727, vol. 57/58.
Gu et al., "Fermentative High-Titer Ethanol Production from Douglas-Fir Forest Residue Without Detoxification Using SPORL: High SO2 Loading at Low Temperature," 2016, Industrial Biotechnology, pp. 168-175, vol. 12, No. 3.
Harris et al., "Stimulation of Lignocellulosic Biomass Hydrolysis by Proteins of Glycoside Hydrolase Family 61: Structure and Function of a Large, Enigmatic Family," 2010, Biochemistry, pp. 3305-3316, vol. 49.
Hodge et al., "Soluble and insoluble solids contributions to high-solids enzymatic hydrolysis of lignocellulose," 2008, Bioresource Technology, pp. 8940-8948, vol. 99.
Kumar et al., "Access of Cellulase to Cellulose and Lignin for Poplar Solids Produced by Leading Pretreatment Technologies," 2009, Biotechnol. Prog., pp. 807-819, vol. 25, No. 3.

(56) References Cited

OTHER PUBLICATIONS

Lan et al., "High titer ethanol production from SPORL-pretreated lodgepole pine by simultaneous enzymatic saccharification and combined fermentation," 2013, Bioresource Technology, pp. 291-297, vol. 127.

Leu et al., "Substrate-Related Factors Affecting Enzymatic Saccharification of Lignocelluloses; Our Recent Understanding," 2013, Bioenerg. Res., pp. 405-415, vol. 6.

Liu et al., "Effect of Sulfite Pretreatment to Overcome the Recalcitrance of Lignin (SPORL) on Enzymatic Saccharification of Corn Stalk," 2011, Bioresouces, 5001-5011, vol. 6(4).

Mackie et al., "Effect of Sulphur Dioxide and Sulphuric Acid on Steam Explosion of Aspenwood," 1985, Journal of Wood Chemistry and Technology, pp. 405-425, vol. 5(3).

Mamers et al., "Explosion pretreatment of Pinus radiata woodchips for the production of fermentation substrates," 1984, Apita, pp. 644-649, vol. 37, No. 8.

Martin et al., "Comparison of the Fermentability of Enzymatic Hydrolyzates of Sugarcane Bagasse Pretreated by Steam Explosion Using Different Impregnating Agents," 2002, Applied Biochemistry and Biotechnology, pp. 699-716, vol. 98-100.

Monavari et al., "Improved One-Step Steam Pretreatment if SO2-Impregnated Softwood with Time-Dependant Temperature Profile for Ethanol Production," 2010, Biotechnol. Prog., pp. 1054-1060, vol. 26, No. 4.

Nguyen et al., "Dilute Acid Pretreatment of Softwoods," 1998, Applied Biochemistry and Biotechnology, pp. 77-89, vol. 70-72.

Nguyen et al., "Two-Stage Dilute Acid Pretreatment of Softwoods," 2000, Applied Biochemistry and Biotechnology, 561-576, vol. 84-86.

Ohgren et al., "Optimization of Steam Pretreatment of SO2-Impregnated Corn Stover for Fuel Ethanol Production," 2005, Applied Biochemistry and Biotechnology, pp. 1055-1067, vol. 121-124.

Pedersen et al., "Low temperature lignocellulose pretreatment: effects and interactions of pretreatment pH are critical for maximizing enzymatic monosaccharide yields from wheat straw," 2011, Biotechnology for Biofuels, pp. 1-10, vol. 4:11.

Rakkolainen et al., "SO2-Ethanol-Water Fractionation of Forest Biomass and Implications for Biofuel Production by Abe Fermentation," 2010, Cellulose Chem. Technol., pp. 139-145, vol. 44.

Ramos et al., "Characterization of Residual Lignin after SO2-Catalyzed Steam Explosion and Enzymatic Hydrolysis of Eucalyptus viminalis Wood Chips," 1999, J. Agric. Food Chem., pp. 2295-2302, vol. 47.

Ramos et al., "Comparison of Steam Pretreatment of Eucalyptus, Aspen, and Spruce Wood Chips and their Enzymatic Hydrolysis," 1992, Applied Biochemistry and Biotechnology, pp. 37-48, vol. 34/35.

Ramos et al., "Effect of enzymatic hydrolysis on the morphology and fine structure of pretreated cellulosic residues," 1993, Enzyme Microb. Technol., pp. 821-831, vol. 15.

Sassner et al., "Steam Pretreatment of Salix with and without SO2 Impregnation for Production of Bioethanol," 2005, Applied Biochemistry and Biotechnology, pp. 1101-1117, vol. 121-124.

Schell et al., "A Technical and Economic Analysis of Acid-Catalyzed Steam Explosion and Dilute Sulfuric Acid Pretreatments Using Wheat Straw or Aspen Wood Chips," 1991, Applied Biochemistry and Biotechnology, pp. 87-97, vol. 28/29.

Schell et al., "Pretreatment of Softwood by Acid-Catalyzed Steam Explosion Followed by Alkali Extraction," 1998, Applied Biochemistry and Biotechnology, pp. 17-24, vol. 70-72.

Schwald et al., "Assessment of Pretreatment Conditions to Obtain Fast Complete Hydrolysis on High Substrate Concentrations," 1989, Applied Biochemistry and Biotechnology, pp. 29-44, vol. 20/21.

Sendelius, "Steam Pretreatment Optimisation for Sugarcane Bagasse in Bioethanol Production," 2005, Master of Science Thesis, Lund University, Sweden.

Shevchenko et al., "Optimization of monosaccharide recovery by post-hydrolysis of the water-soluble hemicellulose component after steam explosion of softwood chips," 2000, Bioresource Technology, pp. 207-211, vol 72.

Shevchenko et al., "The Nature of Lignin from Steam Explosion/ Enzymatic Hydrolysis of Softwood," 1999, Applied Biochemistry and Biotechnology, pp. 867-876, vol. 77-79.

Shi et al., "Sugar yields from dilute sulfuric acid and sulfur dioxide pretreatments and subsequent enzymatic hydrolysis of switchgrass," 2011, Bioresource Technology, pp. 8930-8938, vol. 102.

Shuai et al., "Comparative study of SPORL and dilute-acid pretreatments of spruce for cellulosic ethanol production," 2010, Bioresource Technology, pp. 3106-3114, vol. 101.

Sipos et al., "Steam pretreatment of dry and ensiled industrial hemp for ethanol production," 2010, Biomass and Bioenergy, pp. 1-11.

Sluiter et al., "Determination of Structural Carbohydrates and Lignin in Biomass," NREL Technical Report 2012.

Soderstrom et al., "Effect of Washing on Yield in One- and Two-Step Steam Pretreatment of Softwood for Production of Ethanol," 2004, Biotechnol. Prog., pp. 744-749, vol. 20.

Soderstrom et al., "Separate versus Simultaneous Saccharification and Fermentation of Two-Step Steam Pretreated Softwood for Ethanol Production," 2005, Journal of Wood Chemistry, pp. 187-202, vol. 25.

Soderstrom et al., "Two-Step Steam Pretreatment of Softwood with SO2 Impregnation for Ethanol Production," 2002, Applied Biochemistry and Biotechnology, pp. 5-21, vol. 98-100.

Stenberg et al, "Optimisation of Steam Pretreatment of SO2-Impregnated Mixed Softwoods for Ethanol Production," 1998, J. Chem. Technol. Biotechnol, pp. 299-308, vol. 71.

Szengyel et al., "Cellulase Production of Trichoderma reesei Rut C 30 Using Steam-Pretreated Spruce," 2000, Applied Biochemistry and Biotechnology, pp. 679-691, vol. 84-86.

Tao et al.,"Process and technoeconomic analysis of leading pretreatment technologies for lignocellulosic ethanol production using switchgrass," 2011, Bioresource Technology, pp. 11105-11114, vol. 102.

Tengborg et al., "Comparison of SO2 and H2SO4 Impregnation of Softwood Prior to Steam Pretreatment on Ethanol Production," 1998, Applied Biochemistry and Biotechnology, pp. 3-15, vol. 70-72.

Tengborg et al., "Reduced inhibition of enzymatic hydrolysis of steam-pretreated softwood," 2001, Enzyme and Microbial Technology, pp. 835-844, vol. 28.

Tian et al., "Comparisons of SPORL and Dilute Acid Pretreatments for Sugar and Ethanol Productions from Aspen," 2011, Biotechnol. Prog. pp. 419-427, vol. 27, No. 2.

Tian et al., "Robust cellulosic ethanol production from SPORL-pretreated lodgepole pine using an adapted strain Saccharomyces cerevisiae without detoxification," 2010, Bioresource Technology, pp. 8678-8685, vol. 101.

Trajano et al., "Fundamentals of Biomass Pretreatment at Low pH," 2013, Aqueous Pretreatment of Plant Biomass for Biological and Chemical Conversion to Fuels and Chemicals, pp. 103-128.

Vera et al., "Synergistic effects of mixing hybrid poplar and wheat straw biomass for bioconversion processes," 2015, Biotechnol Biofuels, pp. 1-10, vol. 8:226.

Von Sivers et al., "A Techno-Economical Comparison of Three Processes for the Production of Ethanol from Pine," 1995, Bioresource Technology, pp. 43-52, vol. 51.

Wang et al., "Ethanol production from poplar wood through enzymatic saccharification and fermentation by dilute acid and SPORL pretreatments," 2012, Fuel, pp. 606-614, vol. 95.

Wang et al., "Lignosulfonate and elevated pH can enhance enzymatic saccharification of lignocelluloses," 2013, Biotechnology for Biofuels, pp. 1-10, vol. 6:9.

Wang et al., "Sulfite Pretreatment to Overcome Recalcitrance of Lignocellulose (SPORL) for Robust Enzymatic Saccharification of Hardwoods," 2009, Biotechnol. Prog., pp. 1086-1093, vol. 25, No. 4.

Wayman et al., "Hydrolysis of Biomass by Sulphur Dioxide," 1984, Biomass, pp. 183-191, vol. 6.

(56) References Cited

OTHER PUBLICATIONS

Wayman et al., "SO2 Catalysed Prehydrolysis of Coniferous Wood for Ethanol Production," 1986, Biotechnology Letters, pp. 749-752, vol. 8, No. 10.

Wiman et al., "Cellulose accessibility determines the rate of enzymatic hydrolysis of steam-pretreated spruce," 2012, Bioresource Technology, pp. 208-215, vol. 126.

Wolfinger et al., "Modeling of the Acid Sulfite Pulping Process.—Problem Definition and Theoretical Approach for a Solution with the Main Focus on the Recovery of Cooking Chemicals," 2004, Lenzinger Berichte, pp. 35-45, vol. 83.

Wooley, Bob, "Production of 1,000 Gallons of BioJet," 2015, Presentation from 2015 Annual Meeting of Northwest Advanced Renewables Alliance (NARA).

Wyman et al., "Comparative data on effects of leading pretreatments and enzyme loadings and formulations on sugar yields from different switchgrass sources," 2011, Bioresource Technology, 11052-11062, vol. 102.

Wyman et al., "Comparative Sugar Recovery and Fermentation Data Following Pretreatment of Poplar Wood by Leading Technologies," 2009, Biotechnol. Prog., pp. 333-339, vol. 25, No. 2.

Zhang et al., "Sulfite (SPORL) pretreatment of switchgrass for enzymatic saccharification," 2013, Bioresource Technology, pp. 127-134, vol. 129.

Zhou et al., "Bioconversion of Beetle-Killed Lodgepole Pine Using SPORL: Process Scale-Up Design, Lignin Coproduct, and High Solids Fermentation without Detoxification," 2013, Industrial & Engineering Chemistry Research, pp. A-I.

Zhu et al., "Ethanol production from SPORL-pretreated lodgepole pine: preliminary evaluation of mass balance and process energy efficiency," 2010, Appl Microbiol Biotechnol, pp. 1355-1365, vol. 86.

Zhu et al., "High Titer Ethanol Production from Forest Residue Using Sulfite Mill Pulping Chemistry," 2015, Presentation at 2015 TAPPI IBBC.

Zhu et al., "High titer ethanol production from simultaneous enzymatic saccharification and fermentation of aspen at high solids: A comparison between SPORL and dilute acid pretreatments," 2011, Bioresource Technology, pp. 8921-8929, vol. 102.

Zhu et al., "On Polydispersity of Plant Biomass Recalcitrance and Its Effects on Pretreatment Optimization for Sugar Production," 2011, Bioenerg. Res., pp. 201-210, vol. 4.

Zhu et al., "Quantitative predictions of bioconversion of aspen by dilute acid and SPORL pretreatments using a unified combined hydrolysis factor (CHF)," 2012, Process Biochemistry, pp. 785-791, vol. 47.

Zhu et al., "Sulfite pretreatment (SPORL) for robust enzymatic saccharification of spruce and red pine," 2009, Bioresource Technology, pp. 2411-2418, vol. 100.

Zhu et al., "Using sulfite chemistry for robust bioconversion of Douglas-fir forest residue to bioethanol at high titer and lignosulfonate: A pilot-scale evaluation," 2015, Bioresource Technology, pp. 390-397, vol. 179.

Zhu et al., "Woody biomass pretreatment for cellulosic ethanol production: Technology and energy consumption evaluation," 2010, Bioresource Technology, pp. 4992-5002, vol. 101.

International Search Report and Written Opinion dated Nov. 9, 2016 for PCT Application No. PCT/CA2016/051088, filed Sep. 16, 2016.

\* cited by examiner

SULFUR DIOXIDE AND/OR SULFUROUS ACID PRETREATMENT

CROSS-REFERENCE TO RELATED APPLICATIONS

This application is a national stage application of PCT/CA2016/051088 having an international filing date of Sep. 16, 2016, which claims benefit of U.S. provisional application No. 62/269,339 filed Dec. 18 2015, U.S. provisional application No. 62/293,481 filed Feb. 10, 2016, U.S. provisional application No. 62/364,219 filed Jul. 19, 2016, and international application PCT/CA2016/050291 filed Mar. 16, 2016.

TECHNICAL FIELD

The present disclosure relates to a process and/or system for pretreating lignocellulosic biomass with sulfur dioxide and/or sulfurous acid prior to enzymatic hydrolysis.

BACKGROUND

The production of transportation fuels from biomass (e.g., ethanol, butanol, methane, biodiesel) continues to attract interest, due to the low cost and wide availability of biomass, and because biofuels may be used to displace the use of fossil fuels. For example, bioethanol may be blended into gasoline at predetermined concentrations (e.g., 10%).

First generation biofuels, also referred to as conventional biofuels, are made from biomass that contains sugar, starch, or vegetable oil (e.g., food crops). For example, ethanol may be produced by fermenting sugars that are easily extracted from sugar crops (e.g., sugar cane or sugar beets), or may be produced by fermenting sugars derived from starch-based feedstocks (e.g., corn grain, barley, wheat, potatoes, cassava). However, the diversion of farmland or crops for first generation biofuel production has led to much debate about increased food prices and/or decreased food supplies associated therewith. In addition, there are concerns related to the energy and environmental impact of these production processes.

Second generation biofuels, also referred to as advanced biofuels, wherein the biomass contains lignocellulosic material and/or is obtained from agricultural residues or waste (e.g., corn cobs, corn stover (e.g., stocks and leaves), bagasse, wood chips, wood waste), may allay some of these concerns. For example, when bioethanol produced using second generation processes (i.e., also referred to as cellulosic ethanol) is derived from agricultural waste or residue, its production should not affect the food supply. Accordingly, tremendous effort is currently being expended to advance cellulosic ethanol production processes.

Lignocellulosic biomass typically contains cellulose, hemicellulose and lignin, each of which is commonly present in plant cell walls. Cellulose (e.g., a type of glucan) is an unbranched chain polysaccharide including hexose (C6) sugar monomers (e.g., glucose). Hemicellulose is a branched chain polysaccharide that may include different pentose (C5) sugar monomers (e.g., xylose and arabinose) in addition to glucose. Lignin is a complex organic polymer, which typically includes cross-linked phenol polymers. Although generally insoluble in water at mild conditions, lignin may be soluble in varying degrees in dilute acid or base alkali. The ratio and/or structure of these components (e.g., cellulose, hemicellulose, and lignin) may vary depending on the biomass source.

Unfortunately, since cellulose, hemicellulose, and/or lignin found in lignocellulosic biomass typically is structured to resist degradation, it can be difficult to release sugars from this naturally recalcitrant material. Accordingly, a pretreatment step often is used to open up the structure of the lignocellulosic material and/or to make it accessible for enzymes. The pretreated material, which is more amenable to enzymatic hydrolysis, may then be converted to sugars, such as glucose, with enzymes, and then fermented with a microorganism. The fermentation product (e.g., an alcohol such as ethanol or butanol), may then be recovered (e.g., distillation) and used as a transportation fuel or other product.

Some examples of pretreatments used to prepare the lignocellulosic biomass for enzymatic hydrolysis include dilute acid pretreatment, alkali pretreatment (e.g., lime), ammonia fiber expansion, autohydrolysis (e.g., hot water extraction that does not require the addition of acid or base), steam explosion, organic solvent, and/or wet oxidation.

One type of pretreatment that has been studied is sulfur dioxide ($SO_2$)-catalyzed steam pretreatment. Sulfur dioxide is a gas, which when dissolved in water, may be referred to as sulfurous acid. Sulfur dioxide and/or sulfurous acid may be a suitable catalyst for acid-catalyzed steam pretreatment since it may produce a more digestible substrate. In addition, it may produce less and/or fewer inhibitors and/or inactivators relative to dilute sulfuric acid pretreatment.

However, pretreatment with sulfur dioxide has been limited. First, sulfur dioxide costs more than sulfuric acid (e.g., on a weight basis). Second, sulfur dioxide is a weaker acid than sulfuric acid, so more acid required. As a result of the increased cost and amount of acid required, and/or as a result of environmental concerns, it may be desirable to recover and/or the reuse the sulfur dioxide, which adds to the cost. To date, the performance with sulfur dioxide has not offset these additional costs.

In particular, the use of sulfur dioxide has not been adopted in commercial ethanol plants, where the use of sulfuric acid has been preferred. In particular, the observed hydrolysis performance of sulfur dioxide catalyzed steam pretreated lignocellulosic material (e.g., which has been similar to the hydrolysis performance of sulfuric acid catalyzed steam pretreated lignocellulosic material) has not been exceptional enough to outweigh the added cost (e.g., the cost of sulfur dioxide is greater than the cost of sulfuric acid) and/or increased process complexity (e.g., careful handling to address safety and environmental concerns) of using sulfur dioxide.

SUMMARY

The present disclosure describes one or more embodiments wherein the conditions of sulfur dioxide and/or sulfurous acid pretreatment significantly increase the hydrolysis performance relative to a comparative process including a sulfuric acid catalyzed steam pretreatment (e.g., which may result in the amount of enzyme required to be cut in half). Since the cost of enzyme(s) has been regarded as one of the key hurdles towards economic viability of cellulosic ethanol production, the present disclosure may provide a better process for the commercial production of ethanol.

In particular, the present disclosure recognizes that the effectiveness of the pretreatment may be improved by selecting the sulfur dioxide loading in dependence upon the volume of slurry ($V_s$)) and the total volume of the pretreatment reactor ($V_r$). More specifically, the present disclosure recognizes that since sulfur dioxide is volatile, it may be partitioned between the vapour phase (e.g., in the headspace of the pretreatment reactor) and the liquid phase (e.g., in the slurry in the pretreatment reactor), and thus, that the ratio of the volume of slurry to the total volume of the pretreatment reactor ($V_s/V_r$) may determine, at least in part, the effectiveness of pretreatment.

In particular, the instant disclosure recognizes that the effectiveness of the pretreatment may be improved when the sulfur dioxide loading (i.e., $SO_2$ wt % added, based on dry feedstock), sulfur dioxide slurry concentration (i.e., $SO_2$ wt % added, based on moisture in the slurry) are within certain values after being corrected for the partition of sulfur dioxide between the vapour phase and the liquid phase. In one embodiment, the correction is achieved using the ratio of the volume of slurry to the total volume of the pretreatment reactor ($V_s/V_r$). The resulting volume adjusted parameters, including the volume adjusted sulfur dioxide loading and volume adjusted sulfur dioxide slurry concentration, may be used to not only provide and/or predict a more effective pretreatment, but also to improve consistency in pretreatment performance, thus further advancing sulfur dioxide catalyzed pretreatment towards commercialization.

In one embodiment, improved pretreatment is provided by selecting pretreatment conditions such that the product of sulfur dioxide loading and ($V_s/V_r$) is greater than 0.8 wt %. In one embodiment, improved pretreatment is provided by selecting pretreatment conditions such that the product of sulfur dioxide loading and ($V_s/V_r$) is greater than 2 wt %. In one embodiment, improved pretreatment is provided by selecting pretreatment conditions such that the product of sulfur dioxide slurry concentration and ($V_s/V_r$) is between 0.25 wt % and 1.5 wt %. In one embodiment, improved pretreatment is provided by selecting pretreatment conditions such that the product of sulfur dioxide loading and ($V_s/V_r$) is greater than 0.8 wt % and the product of sulfur dioxide slurry concentration and ($V_s/V_r$) is between 0.25 wt % and 1.5 wt %. Advantageously, selecting the amount (e.g. grams) of sulfur dioxide added, both in terms of the amount of dry feedstock and moisture in the slurry, may contribute to improving the pretreatment. In addition, selecting the amount (e.g., grams) of sulfur dioxide added in terms of the amount of headspace available (e.g., using ($V_s/V_r$)) may further improve pretreatment and/or consistency between pretreatments. It has also been recognized that a significant amount of work with sulfur dioxide pretreatment has been carried out in pretreatment reactors, including steam guns, in which a relatively small volume of feedstock slurry impregnated with sulfur dioxide is placed in a vessel with a large headspace volume. As sulfur dioxide is volatile, and especially so at the elevated temperatures used in pretreatment, a proportion of the sulfur dioxide migrates to the vapor phase, and thus may not participate in the pretreatment reactions occurring in the wet feedstock slurry. It has been recognized that the performance of sulfur dioxide pretreatment may be improved by taking the migration of sulfur dioxide into the vapor phase into account when selecting the amount of sulfur dioxide to use in the pretreatment.

For example, it has been recognized that the effectiveness of the pretreatment is not only dependent on using a particular optimized parameter (e.g. sulfur dioxide loading), but that a more effective pretreatment may be obtained if the optimized parameter is selected in dependence upon other parameters and/or used to select other parameters. For example, while selecting the amount of sulfur dioxide added (e.g., $SO_2$ wt % concentration, based on dry feedstock or amount of moisture in the slurry), to be within a predetermined range may improve pretreatment, further selecting the amount of sulfur dioxide added to be within a predetermined range in dependence on another parameter (e.g., amount of headspace available or $V_s/V_r$) may further improve pretreatment and/or consistency between pretreatments. Notably, parameters such as the amount of headspace and/or $V_s/V_r$, have been previously neglected and/or overlooked when determining pretreatment conditions, such as sulfur dioxide loading and/or moisture level, for an effective pretreatment.

Although the amount of sulfur dioxide corresponding to pretreatment conditions wherein the product of sulfur dioxide loading and ($V_s/V_r$) is greater than 0.8 wt % and the product of sulfur dioxide slurry concentration and ($V_s/V_r$) is between 0.25 wt % and 1.5 wt %, may be relatively large, further cost savings may be achieved by recovering and/or recycling sulfur dioxide from the pretreatment, particularly, by flashing.

Additionally, or alternatively, the amount of sulfur dioxide added per amount of dry biomass added (e.g., sulfur dioxide loading) may be reduced, while still providing the same amount of sulfur dioxide present within the pretreatment reactor, by preventing at least some of the sulfur dioxide within the pretreatment reactor from leaving the reactor when at least a portion of the pretreated biomass is discharged from the reactor. In this embodiment, the sulfur dioxide prevented from leaving the reactor combines with the added make-up sulfur dioxide to build up the total amount of sulfur dioxide present within the pretreatment reactor, and thus available for pretreatment. The total amount of sulfur dioxide present within the pretreatment reactor per total amount of dry lignocellulosic biomass present within the pretreatment reactor is termed the sulfur dioxide dosage.

The product of sulfur dioxide dosage and ($V_s/V_r$) is termed the "volume adjusted sulfur dioxide loading" and/or "effective sulfur dioxide dosage", whereas the product of sulfur dioxide slurry concentration and ($V_s/V_r$) is termed the "volume adjusted sulfur dioxide slurry concentration" and/or the "effective sulfur dioxide slurry concentration".

In accordance with one aspect of the instant invention there is provided a method for pretreating and hydrolyzing lignocellulosic biomass comprising: a) adding acid to the lignocellulosic biomass to produce acidified lignocellulosic biomass, said acid comprising at least one of sulfur dioxide and sulfurous acid; b) pretreating the acidified lignocellulosic biomass in at least one pretreatment reactor to provide a pretreated slurry having a pH less than 1.5, said pretreated slurry comprising cellulose, said acidified lignocellulosic biomass having a consistency between 14.5 wt % and 51 wt %, said at least one pretreatment reactor comprising a first pretreatment reactor, said pretreating conducted at a temperature greater than 170° C. and under pretreating conditions wherein a product of sulfur dioxide dosage and $V_s/V_r$ is greater than 0.8 wt %, where $V_s/V_r$ is a ratio of slurry volume to reactor volume and where sulfur dioxide dosage is a ratio of grams of sulfur dioxide present in the first pretreatment reactor to grams of dry lignocellulosic biomass present in the first pretreatment reactor expressed as a weight percentage; and c) hydrolyzing the cellulose from the pretreated slurry with an enzyme to produce glucose.

In accordance with one aspect of the instant invention there is provided a method for pretreating and hydrolyzing lignocellulosic biomass comprising: a) adding acid to the lignocellulosic biomass to produce acidified lignocellulosic biomass, said acid comprising at least one of sulfur dioxide and sulfurous acid; b) pretreating the acidified lignocellulosic biomass in at least one pretreatment reactor to provide a pretreated slurry, said pretreated slurry comprising cellulose and having a pH that is less than 1.55, said acidified lignocellulosic biomass having a consistency that is greater than 14.5 wt % and less than 50.5 wt %, said at least one pretreatment reactor comprising a first pretreatment reactor having a reactor volume $V_r$ and a slurry volume $V_s$; and c) hydrolyzing the cellulose with an enzyme to produce glucose, wherein adding the acid to the lignocellulosic biomass comprises adding an amount of the acid that provides an effective sulfur dioxide dosage that is greater than 1 wt % and an effective sulfur dioxide slurry concentration that is between 0.25 wt % and 1.5 wt %, said effective sulfur dioxide slurry concentration calculated from the product of the sulfur dioxide slurry concentration in the first pretreatment reactor and $V_s/V_r$, said sulfur dioxide slurry concentration calculated from the ratio of grams of sulfur dioxide present to grams of moisture present expressed as a weight percentage, said effective sulfur dioxide dosage calculated from the product of sulfur dioxide dosage in the first pretreatment reactor and $V_s/V_r$, and wherein said pretreating is conducted at a temperature greater than 170° C.

In accordance with one aspect of the instant invention there is provided a method for pretreating and hydrolyzing lignocellulosic biomass comprising: a) adding acid to the lignocellulosic biomass to produce acidified lignocellulosic biomass, said acid comprising at least one of sulfur dioxide and sulfurous acid; b) pretreating the acidified lignocellulosic biomass in at least one pretreatment reactor at a temperature greater than 170° C. to provide a pretreated slurry comprising cellulose, said acidified lignocellulosic biomass having a consistency that is greater than 14.5 wt % and less than 40.5 wt %, said at least one pretreatment reactor comprising a first pretreatment reactor having a reactor volume $V_r$ and a slurry volume $V_s$; and c) hydrolyzing the cellulose from the pretreated slurry with an enzyme to produce glucose, wherein adding the acid to the lignocellulosic biomass comprises adding an amount of the acid that provides an effective sulfur dioxide dosage that is greater than 2 wt %, said effective sulfur dioxide dosage calculated from the product of sulfur dioxide dosage in the first pretreatment reactor and $V_s/V_r$, and wherein the lignocellulosic biomass comprises a lignocellulosic biomass other than softwood.

In accordance with another aspect of the instant invention there is provided a system for producing a fermentation product from lignocellulosic biomass comprising: at least one pretreatment reactor configured for pretreating the lignocellulosic biomass, said at least one pretreatment reactor comprising a first pretreatment reactor having a reactor volume $V_r$ and a slurry volume $V_s$, said at least one pretreatment reactor including at least one outlet configured for discharging a pretreated slurry comprising cellulose; at least one hydrolysis tank disposed downstream of said at least one outlet and configured for hydrolyzing the cellulose with a cellulase enzyme to produce glucose; at least one fermentation tank disposed downstream of the at least one hydrolysis tank and configured for fermenting the glucose to produce the fermentation product; at least one inlet configured for introducing acid to acidify the lignocellulosic biomass, said acid comprising at least one of sulfur dioxide and sulfurous acid, said at least one inlet disposed upstream of the at least one pretreatment reactor, in the at least one pretreatment reactor, or a combination thereof; and at least one controller configured for adjusting at least one of a flow of the acid, the slurry volume $V_s$, and a consistency of the lignocellulosic biomass fed to the first pretreatment reactor, said at least one controller configured for adjusting the flow of the acid such that a pH of the pretreated slurry is lower than 1.5 and configured for adjusting at least one of the flow of the acid, the slurry volume $V_s$, and the consistency of the lignocellulosic biomass fed to the first pretreatment reactor such that an effective sulfur dioxide dosage for the first reactor is greater than 1 wt %, and an effective sulfur dioxide slurry concentration for the first reactor is between 0.25 wt % and 1.5 wt %.

In accordance with another aspect of the instant invention there is provided a method for pretreating and hydrolyzing lignocellulosic biomass comprising: pretreating lignocellulosic biomass in at least one pretreatment reactor to provide a pretreated slurry comprising cellulose, said lignocellulosic biomass having a consistency between 14.5 wt % and 51 wt %, said at least one pretreatment reactor comprising a first pretreatment reactor having a slurry volume $V_s$ and a reactor volume $V_r$, said pretreating comprising heating the lignocellulosic biomass in the first pretreatment reactor to at least 170° C. in the presence of acid, said acid comprising at least one of sulfur dioxide and sulfurous acid and present in an amount sufficient to provide a final pH less than 1.5 and a product of sulfur dioxide dosage and $V_s/V_r$ that is greater than 1 wt %; and hydrolyzing the cellulose from the pretreated slurry with an enzyme to produce glucose, wherein the sulfur dioxide dosage is a ratio of grams of sulfur dioxide present in the first pretreatment reactor to grams of dry lignocellulosic biomass present in the first pretreatment reactor expressed as a weight percentage.

DETAILED DESCRIPTION

Figure 1:
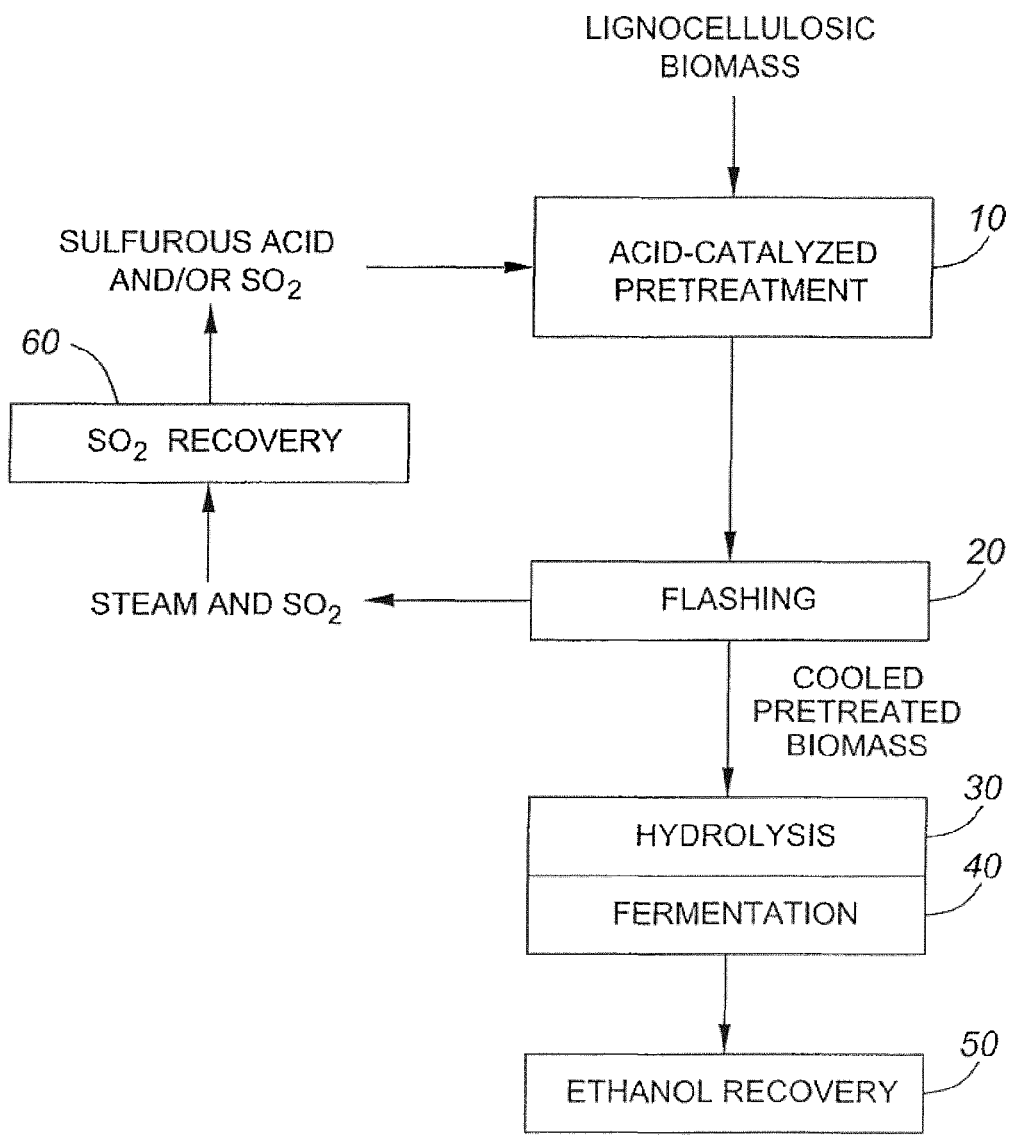
FIG. 1 is a block flow diagram of a method according to one embodiment of the invention.

Certain exemplary embodiments of the invention now will be described in more detail, with reference to the drawings, in which like features are identified by like reference numerals. The invention may, however, be embodied in many different forms and should not be construed as limited to the embodiments set forth herein.

The terminology used herein is for the purpose of describing certain embodiments only and is not intended to be limiting of the invention. For example, as used herein, the singular forms "a", "an," and "the" may include plural references unless the context clearly dictates otherwise. The terms "comprises", "comprising", "including", and/or "includes", as used herein, are intended to mean "including but not limited to". The term "and/or", as used herein, is intended to refer to either or both of the elements so conjoined. The phrase "at least one" in reference to a list of one or more elements, is intended to refer to at least one element selected from any one or more of the elements in the list of elements, but not necessarily including at least one of each and every element specifically listed within the list of elements. Thus, as a non-limiting example, the phrase "at least one of A and B" may refer to at least one A with no B present, at least one B with no A present, or at least one A and at least one B in combination. In the context of describing the combining of components by the "addition" or "adding" of one component to another, those skilled in the art will understand that the order of addition is not critical (unless stated otherwise). Thus, for example, reference herein to "adding" an acid to a biomass will be understood as a reference to the act of combining the acid and biomass, whether by adding the acid to the biomass, adding the biomass to the acid, or both. The terms "first", "second", etc., may be used to distinguish one element from another, and these elements should not be limited by these terms. Unless defined otherwise, all technical and scientific terms used herein have the same meanings as commonly understood by one of ordinary skill in the art.

Retelling to FIG. 1, there is shown a method in accordance with one embodiment of the invention. Lignocellulosic biomass is fed to a pretreatment 10, which involves a heating step, to produce pretreated biomass. The pretreatment 10, which may be conducted in one or more pressurized pretreatment reactors at a temperature above about 170° C., and typically above about 180° C. is an acid-catalyzed pretreatment. The acid, which may be added in the pretreatment reactor(s) and/or upstream of the pretreatment reactor(s), includes at least one of sulfur dioxide and sulfurous acid. In one embodiment, and as discussed in further detail below, the acid will be added in an amount that results in an effective sulfur dioxide dosage greater than about 0.8 wt %, an effective sulfur dioxide concentration in the slurry between about 0.25 wt % and 1.5 wt %, and a final pH below about 1.5. Once the acidified lignocellulosic biomass is heated to the desired temperature, and/or is maintained at or above the pretreatment temperature for the desired time, the pretreated material may be discharged. In one embodiment, the pressure on the pretreated lignocellulosic biomass is reduced by flashing 20 such that a volatile portion of the reactor contents flashes off in a flash stream comprising steam and sulfur dioxide, while the condensate portion is cooled. The cooled pretreated slurry (e.g., the condensate portion) is fed to hydrolysis 30 followed by fermentation 40, or is fed to a combined hydrolysis/fermentation 30/40. The hydrolysis 30 converts cellulose in the cooled pretreated slurry to glucose, while the fermentation converts at least a portion of the glucose to an alcohol such as ethanol, which may be recovered in an alcohol recovery step 50. The flash stream produced upon flashing 20, which may include steam and/or sulfur dioxide, may be fed to a sulfur dioxide recovery 60 (e.g., directly or indirectly). The optional sulfur recovery 60 provides sulfur dioxide and/or sulfurous acid in a form suitable for recycling back into the process.

Lignocellulosic Biomass

The term "lignocellulosic biomass", as used herein, refers to any type of biomass containing cellulose and lignin, and which may also contain hemicellulose. In general, the combined content of cellulose, hemicellulose, and lignin may be greater than 25 wt %, more preferably greater than 50 wt % or 75 wt %. In some embodiments, sucrose, fructose, and/or starch are also present, but in lesser amounts than cellulose and hemicellulose.

In general, the lignocellulosic biomass fed to the pretreatment 10 may include and/or be derived from any lignocellulosic feedstock that needs to be pretreated in order to improve accessibility and/or susceptibility to enzyme (e.g., for enzymatic hydrolysis).

Some examples of suitable lignocellulosic feedstock include: (i) energy crops; (ii) residues, byproducts, or waste from the processing of plant biomass in a facility or feedstock derived therefrom; (iii) agricultural residues; (iv) forestry biomass; (v) waste material derived from pulp and paper products; (vi) pulp and paper waste; and/or (vii) municipal waste including components removed from municipal waste.

Energy crops include biomass crops such as grasses, including C4 grasses, such as switch grass, energy cane, sorghum (including sweet sorghum), cord grass, rye grass, *miscanthus*, reed canary grass, C3 grasses such as *Arundo donax*, or a combination thereof.

Residues, byproducts, or waste from the processing of plant biomass in a facility of feedstock derived therefrom include residues remaining after obtaining sugar from plant biomass such as sugar cane bagasse, sugar cane tops and leaves, beet pulp, or residues remaining after removing sugar from Jerusalem artichoke or residues remaining after grain processing, such as corn fiber, corn stover, or bran from grains. Agricultural residues include, but are not limited to soybean stover, corn stover, rice straw, sugar cane tops and/or leaves, rice hulls, barley straw, corn cobs, wheat straw, canola straw, oat straw, oat hulls, corn fiber, and corn cobs.

Forestry biomass includes recycled wood pulp fiber, sawdust, hardwood, softwood, trimmings, and/or slash from logging operations. Pulp and paper waste includes waste from chemical pulping such as black liquor, spent sulfite liquor, sludge, and/or fines.

Municipal waste includes post-consumer material or waste from a variety of sources such as domestic, commercial, institutional and/or industrial sources. For example, in one embodiment, the lignocellulosic feedstock includes refuse from waste collection and/or sewage sludge.

In one embodiment, the lignocellulosic feedstock is (i) an energy or biomass crop, (ii) an agricultural residue, and/or (iii) hardwood. In one embodiment, the lignocellulosic feedstock is a non-woody lignocellulosic feedstock such as (i) an energy crop, (ii) residues, byproducts or waste from processing of plant biomass or feedstock derived therefrom in a facility, and/or (iii) agricultural residues. In one embodiment, the lignocellulosic feedstock is a non-woody lignocellulosic feedstock such as (i) an energy crop and/or (ii) an agricultural residue. In one embodiment, the lignocellulosic feedstock is straw, stover, or an energy crop. As used herein, the term "straw" refers to the stem, stalk and/or foliage portion of crops remaining after the removal of starch and/or sugar containing components for consumption. Examples of straw include, but are not limited to sugar cane tops and/or leaves, bagasse, oat straw, wheat straw, rye straw, oat straw, rice straw and barley straw. The term "stover" includes the stalk and foliage portion of crops after the removal of starch and/or sugar containing components of plant material for consumption. Examples of stover include, but are not limited to, soybean stover, sorghum stover, and corn stover. In one embodiment, the lignocellulosic feedstock is a mixture of fibers that originate from different kinds of plant materials, including mixtures of cellulosic and non-cellulosic feedstocks.

Biomass Preparation

In general, the lignocellulosic biomass may be subjected to one or more optional preparatory steps prior to pretreatment 10 and/or as part of the pretreatment 10. Some examples of biomass preparation include size reduction, washing, leaching, sand removal, slurry formation, soaking, wetting, dewatering, plug formation, addition of heat, and addition of chemicals (e.g., pretreatment and/or other). In general, these preparatory steps may depend on the type of biomass and/or the selected pretreatment conditions.

In one embodiment, the lignocellulosic biomass is subjected to a size reduction. Some examples of size reduction methods include milling, grinding, agitation, shredding, compression/expansion, and/or other types of mechanical action. Size reduction by mechanical action may be performed by any type of equipment adapted for the purpose, for example, but not limited to, hammer mills, tub-grinders, roll presses, refiners, hydropulpers, and hydrapulpers. In one embodiment, lignocellulosic feedstock having an average particle size that is greater than about 6-8 inches is subject to a size reduction wherein at least 90% by volume of the particles produced from the size reduction have a length between about 1/16 inch and about 6 inches. Some examples of suitable size reductions and/or equipment are described in WO 2006/026863.

In one embodiment, the lignocellulosic biomass is washed and/or leached with a liquid (e.g., water and/or an aqueous solution). Washing, which may be performed before, during, or after size reduction, may remove sand, grit, fine particles of the lignocellulosic feedstock, and/or other foreign particles that otherwise may cause damage to the downstream equipment. Leaching, which may be performed before, during, or after size reduction, may remove soluble components from the lignocellulosic feedstock. For example, in one embodiment, leaching includes contacting the biomass with water or an aqueous solution for more than about 2 minutes in order to remove salts and/or buffering agents. For example, the lignocellulosic biomass may be leached as set forth in WO 02/070753 to Griffin, which is hereby incorporated by reference and particularly for the purpose of describing such leaching.

In one embodiment, the lignocellulosic biomass is subject to a sand removal. For example, in one embodiment, the lignocellulosic biomass is washed to remove sand. Alternatively, or additionally, sand may be removed using other wet or dry sand removal techniques that are known in the art (e.g., including the use of a hydrocyclone or a sieve).

In one embodiment, the lignocellulosic biomass is slurried in liquid (e.g., water), which allows the lignocellulosic biomass to be pumped. In one embodiment, the lignocellulosic biomass is slurried subsequent to size reduction, washing, and/or leaching. The desired weight ratio of water to dry biomass solids in the slurry may be determined by factors such as pumpability, pipe-line requirements, and other practical considerations. For example, in one embodiment, the biomass is slurried to provide a consistency between about 1 wt % and about 40 wt %, or about 1 wt % and about 20 wt %, or between about 4 wt % and about 10 wt %. In general, slurries having a consistency less than about 10 wt % may be pumped using a relatively inexpensive slurry pump.

In one embodiment, the lignocellulosic biomass is soaked in water and/or an aqueous solution (e.g., comprising a pretreatment chemical). In one embodiment, the biomass is soaked subsequent to being slurried (e.g., the slurried biomass is fed to a soaking tank). Feeding the slurried biomass to a soaking tank may allow pretreatment chemical(s) to more uniformly impregnate the biomass, which in turn may provide even cooking in the heating step of pretreatment. For example, soaking the feedstock in a solution comprising a pretreatment chemical (e.g., such as sulfuric acid and/or sulfurous acid) typically provides uniform impregnation of the biomass with the pretreatment chemical. Soaking the feedstock in water, may allow gaseous pretreatment chemicals (e.g., sulfur dioxide) to more uniformly and/or completely impregnate the lignocellulosic biomass during subsequent chemical addition steps. In general, uniform impregnation of the pretreatment chemical may ensure that some material is not overcooked and/or degraded due to high localized concentration of the pretreatment chemical, and/or that some material is not undercooked (e.g., which may result in lower xylose yield and incomplete cellulose hydrolysis). Undercooking or overcooking of lignocellulosic feedstock may be particularly problematic when the heating step of pretreatment is conducted under medium or high solids consistency since the non-uniformity in the concentration of the pretreatment chemical and the temperature are more pronounced.

Soaking is typically conducted in a tank and/or other suitable equipment for handling soaked material. In one embodiment, soaking is conducted at a relatively low consistency (e.g., between about 1 wt % and about 20 wt %, or about 2 wt % and about 18 wt %, or between about 3 wt % and about 15 wt %). In general, soaking may be carried out at any suitable temperature and/or for any suitable duration. For example, in one embodiment, soaking is conducted at a temperature between about 20° C. and about 80° C. In one embodiment, the soaking duration is between about 1 minute and about 20 minutes. In another embodiment, the soaking duration is longer than 20 minutes. In one embodiment, the water or aqueous solution is provided from a recycle stream obtained from other stages of the process. In one embodiment, soaking is conducted in one or more batch or continuous vessels, or a combination thereof, each of which may be a mixed vessel or an unmixed vessel.

In one embodiment, the lignocellulosic biomass is wet with a liquid (e.g., water or an aqueous solution). For example, in one embodiment, the lignocellulosic biomass is sprayed with water in order to moisten the lignocellulosic biomass and provide a desired consistency. In general, the term consistency refers the amount of undissolved dry solids or "UDS" in a sample, and is often expressed as a ratio on a weight basis (wt:wt), or as a percent on a weight basis, for example, % (w/w), also denoted herein as wt %. For example, consistency may be determined by filtering and washing the sample to remove dissolved solids and then drying the sample at a temperature and for a period of time that is sufficient to remove water from the sample, but does not result in thermal degradation of the sample. After water removal, or drying, the dry solids are weighed and the weight of water in the sample is the difference between the weight of the sample and the weight of the dry solids. Providing lignocellulosic biomass with a higher consistency to pretreatment may advantageously reduce heating requirements (e.g., since there is less liquid to heat).

In one embodiment, the lignocellulosic biomass is at least partially dewatered to provide a desired consistency. In one embodiment, the lignocellulosic biomass is at least partially dewatered in order to increase the undissolved solids content relative to the incoming biomass. In one embodiment, the lignocellulosic biomass is at least partially dewatered in order to remove at least some of the liquid introduced during washing, leaching, slurrying, and/or soaking. In one embodiment, wherein the biomass is subject to dewatering after being slurried and/or after soaking, the liquid expressed from the biomass in dewatering is recycled back to the slurrying and/or soaking steps. In one embodiment, the expressed liquid is water. In one embodiment, the expressed liquid is an aqueous solution containing a pretreatment chemical.

In one embodiment, dewatering is achieved using a drainer, filtration device, screen, screw press, and/or extruder. In one embodiment, dewatering is achieved using a centrifuge. In one embodiment, the dewatering is achieved prior to and/or as part of plug formation. Without being limiting, a plug formation device incorporating a dewatering section may be a pressurized screw press or a plug screw feeder, as described in WO 2010/022511, which is incorporated herein by reference. In one embodiment, dewatering includes removing water from the lignocellulosic biomass under pressure. In one embodiment, dewatering includes removing water from the lignocellulosic biomass at atmospheric pressure. In one embodiment, wherein the biomass is subjected to dewatering under pressure, the pressure increase may be caused by one or more high pressure pumps. The pump, or other feeding device, may increase the pressure of the biomass prior to dewatering (e.g., from about 50 psig to about 900 psig, or about 70 psig to about 800 psig or about 140 psig to about 700 psig). The pressure may be measured with a pressure sensor located at a biomass inlet port on a dewatering device or a plug formation device that also dewaters the feedstock. Alternatively, the feedstock subjected to dewatering may be at atmospheric pressure, or at a pressure below about 50 psig.

In one embodiment, the lignocellulosic biomass (e.g., which may or may not have been subject to a previous dewatering) is subject to plug formation. In general, plug formation may be considered an integration of lignocellulosic biomass particles into a compacted mass referred to herein as a plug. Plug formation devices may or may not form a plug that acts as a seal between areas of different pressure. In general, the plug formation device is provided upstream of the pretreatment reactor(s). In one embodiment, a plug formation device is provided at the front end of a pressurized pretreatment reactor. In one embodiment, the biomass is fed to a plug formation device that dewaters the biomass and/or is disposed downstream of a dewatering device. In one embodiment, a plug formation device that dewaters the biomass includes a housing or shell with openings through which water can pass. Some examples of plug formation devices that dewater biomass include a plug screw feeder, a pressurized screw press, a co-axial piston screw feeder, and a modular screw device.

In one embodiment, the lignocellulosic biomass (e.g., which may or may not have been subject to a previous dewatering) is subject to dewatering with a pressurized screw press. In general, the pressurized screw press compresses the lignocellulosic biomass particles into a compacted accumulation of biomass (e.g., which may or may not be considered a plug). In general, the pressurized screw press is provided upstream of the pretreatment reactor(s). In one embodiment, a pressurized screw press feeds lignocellulosic biomass having a consistency between about 15 wt % and about 40 wt % to the pressurized pretreatment reactor.

In one embodiment, the dewatered biomass may have a weight ratio of water to undissolved dry solids between about 0.5:1 (67 wt % dry solids) and about 5:1 (17 wt % dry solids), or between about 1:1 (50 wt % dry solids) and about 4:1 (20 wt % dry solids), or between about 1.5:1 (40 wt % dry solids) to about 4:1 (20 wt % dry solids), or between about 1.5:1 (40 wt % dry solids) and about 3.5:1 (22 wt % dry solids).

In one embodiment, the compacted biomass provided by the plug formation device has a consistency between about 15 wt % and about 40 wt %. In one embodiment, the compacted biomass provided by the plug formation device has a consistency between about 15 wt % and about 51 wt %. Advantageously, this consistency range has been found to provide a reasonable compromise between providing sufficient moisture for a successful pretreatment with $SO_2$, without overwhelming the system with excess water.

In one embodiment, the lignocellulosic biomass is subject to a step that adds heat (e.g., applying extraneous heat, a hot liquid, and/or steam) prior to the lignocellulosic biomass entering the pretreatment reactor(s). In one embodiment, the biomass is heated as part of the soaking step, as part of a leaching step, or as a separate step. In one embodiment, the biomass is subjected to a steam addition step upstream of the pretreatment reactor(s). In one embodiment, the dewatered biomass is fed to a downstream "heating chamber" or "high shear heating chamber" prior to being fed to the pretreatment reactor(s). For example, the heating chamber, which may be a horizontally-oriented or essentially horizontally-oriented elongate chamber, may include disintegrating elements for disintegrating plugs of biomass into particles (e.g., the compacted/compressed biomass forming the plug is fluffed up such that the particles forming the plug expand and/or spread out with respect to volume) and/or may include inlets for direct steam injection (e.g., to preheat the biomass and provide efficient heat transfer) and/or adding pretreatment chemicals. In one embodiment, a pretreatment chemical such as sulfur dioxide is added during direct steam injection in the heating chamber. In one embodiment, the biomass is preheated prior to being fed to a pretreatment reactor using a heating chamber as disclosed, for example, in U.S. Publication No. 2013/0071903, which is hereby incorporated by reference. In one embodiment, the operating pressure and temperature of the heating chamber corresponds to the pressure and temperature of a downstream pretreatment reactor. In one embodiment, the resident time in the "heating chamber" or "high shear heating chamber" is between about 1 second and about 120 seconds. In one embodiment, the resident time in the "heating chamber" or "high shear heating chamber" is greater than 120 seconds. In one embodiment, the resident time in the "heating chamber" or "high shear heating chamber" is less than 60 seconds. In one embodiment, the resident time in the "heating chamber" or "high shear heating chamber" is less than 30 seconds. In one embodiment, the resident time in the "heating chamber" or "high shear heating chamber" is selected to be equal to or less than the time required to heat the lignocellulosic biomass to the pretreatment temperature. Advantageously, limiting the resident time in the heating chamber to about, or less than, the time required to heat the lignocellulosic biomass to the pretreatment temperature minimizes the amount of pretreatment occurring in the heating chamber, and the subsequent degradation of sugar in the pretreatment reactor. In one embodiment, direct steam injection into the heating chamber heats the lignocellulosic biomass to the pretreatment temperature prior to the lignocellulosic biomass being discharged into the pretreatments reactor. In one embodiment, direct steam injection into the heating chamber heats the lignocellulosic biomass to a temperature lower than the pretreatment temperature prior to the lignocellulosic biomass being discharged into the pretreatments reactor, where the lignocellulosic biomass is further heated to the pretreatment temperature.

As described above, each of the washing, leaching, slurrying, soaking, dewatering, and preheating stages are optional and may or may not be included in the process. In general, if the process is a continuous-flow process, it may be advantageous to include steps of slurrying and dewatering prior to pretreatment in order to improve process economics and efficiency. In addition, providing soaking, preheating, and chemical addition steps upstream of the pretreatment reactor(s) may provide a more uniform and/or efficient pretreatment. Providing acid addition downstream of dewatering and immediately upstream (e.g., in the heating device) and/or directly to pretreatment may advantageously reduce corrosion. In any case, one or more additional steps/devices may also be provided. For example, without being limiting, examples of such devices include mechanical restricting devices, restraining devices, scrapers and conveyors. For example, in one embodiment, a component and/or device is provided downstream and/or as part of the plug formation device that breaks the plug into segments as it is discharged from the plug formation device, or into other devices positioned downstream of the plug formation device (e.g., into a heating chamber).

Pretreatment

The term "pretreatment", as used herein, refers to one or more steps wherein the lignocellulosic biomass is treated such that the structure thereof is disrupted in order to make the cellulose in the lignocellulosic biomass more susceptible and/or accessible to enzymes in a subsequent hydrolysis.

In general, the pretreatment 10 includes feeding the lignocellulosic biomass into a pretreatment reactor, wherein it resides for a time (e.g., residence time) at or above a specific temperature (e.g., pretreatment temperature). In one embodiment, the pretreatment temperature is a predetermined temperature selected to provide the desired level of pretreatment. In one embodiment, the pretreatment temperature is part of a predetermined thermal profile.

In one embodiment, the pretreatment reactor is part of a pretreatment system, which may include a plurality of components/devices in addition to the pretreatment rector. Some examples of these devices/components include a biomass conveyer, washing system, dewatering system, a plug formation device, a heating chamber, a high shear heating chamber, a pre-steaming chamber, an acid impregnation chamber, vapour reservoir chamber, an additional pretreatment reactor, connecting conduits, valves, pumps, etc. For example, in one embodiment, the pretreatment system includes a high shear heating chamber disposed upstream of the pretreatment reactor. In general, the pretreatment system may be formed from different devices/components that are connected in the desired sequence and/or may be constructed such that different devices/components are integrated.

In general, the pretreatment reactor and/or pretreatment system is pressurizable. For example, in one embodiment, the pretreatment reactor and/or pretreatment system includes a plurality of valves and/or other pressure increasing, pressure decreasing, or pressure maintaining components for providing and/or maintaining the pretreatment reactor at a specific pressure. In one embodiment, the pretreatment reactor is held at a pressure greater than about 620 kPa (90 psia). In one embodiment, the pretreatment reactor is held at a pressure between about 620 kPa (90 psia) and about 4,688 kPa (680 psia). The devices/components within the pretreatment system may be held at a same pressure or may be held at different pressures. For example, in one embodiment, the pretreatment system includes a pressurized screw press, a high shear heating chamber, a pretreatment reactor, and a discharge valve (e.g., blow-valve), disposed in sequence, all of which are in fluid communication such that the system pressure between the output of the pressurized screw press and the discharge valve is about the same. In another embodiment, at least one of the devices/components is held at a different pressure.

In general, the pretreatment reactor and/or pretreatment system may include a heater, or some other heating means, for heating the lignocellulosic biomass to the pretreatment temperature. For example, in one embodiment, the pretreatment reactor is clad in a heating jacket. In another embodiment, the pretreatment reactor and/or the pretreatment system includes direct steam injection inlets. In one embodiment, the lignocellulosic biomass is heated (e.g., directly or indirectly) in the pretreatment reactor. In another embodiment, the lignocellulosic biomass is heated prior to entering the pretreatment reactor (e.g., in an upstream heating chamber). In one embodiment, the lignocellulosic biomass is heated both upstream of and in the pretreatment reactor. In any case, direct steam injection may be advantageous in terms of quickly and uniformly heating high consistency biomass and/or for breaking down the biomass structure via steam explosion (e.g., if used).

In general, the lignocellulosic material is heated to a temperature greater than about 120° C., and more preferably above 170° C. For example, in one embodiment, the pretreatment temperature is between about 180° C. and about 300° C., between about 180° C. and about 280° C., and/or between about 185° C. and about 240° C. In one embodiment, the pretreatment temperature is above about 185° C. In one embodiment, the pretreatment temperature is above about 190° C. Providing a pretreatment temperature between about 185° C. and about 240° C. has been found to correspond to relatively good enzymatic hydrolysis, when the pretreatment time is between about 1 minute and about 10 minutes. In practice, there may be a time delay between the time at which the heating process is started and the time when the biomass reaches the pretreatment temperature.

In general, the pretreatment is conducted under acidic conditions (i.e., in the presence of sulfur dioxide and/or sulfurous acid, although other acids, such as sulfuric acid, may be also present). In one embodiment, the pretreatment reactor and/or pretreatment system includes one or more inlets for adding acid into the pretreatment system. For example, in one embodiment, sulfur dioxide and/or sulfurous acid is injected into the pretreatment reactor such that the lignocellulosic biomass and the acid are added separately (i.e., separate inlets). In another embodiment, the lignocellulosic biomass is impregnated with sulfur dioxide and/or sulfurous acid (and optionally another acid such as sulfuric acid) upstream of the pretreatment reactor, such that at least a portion of the sulfur dioxide and/or sulfurous acid is added to the pretreatment reactor with the lignocellulosic biomass (i.e., through the same inlet). In one embodiment, the sulfur dioxide and/or sulfurous acid is added to the lignocellulosic biomass during a soaking step, prior to or after dewatering, prior to or after plug formation, into a heating chamber, into the plug formation device, into a pretreatment reactor, or any combination thereof. For example, in one embodiment, the lignocellulosic biomass is soaked in aqueous sulfurous acid solution, whereas in another embodiment, the lignocellulosic biomass is soaked in water and is at least partially dewatered before gaseous sulfur dioxide is added (e.g., in the heating chamber and/or pretreatment reactor). In one embodiment, acid is added to lignocellulosic biomass prior to entering the pretreatment reactor (e.g., in an upstream impregnation and/or heating chamber), and not in the pretreatment reactor. In general, the sulfur dioxide and/or sulfurous acid may include freshly-added make-up acid and/or recycled acid (e.g., recycled from previous pretreatment reactions).

The addition of acid (e.g., sulfur dioxide and/or sulfurous acid) to the lignocellulosic biomass, at one or more points in the process, provides acidified lignocellulosic biomass. The term "acidified lignocellulosic biomass", as used herein, refers to the fact that the pH of a sample of the lignocellulosic biomass corresponds to acidic conditions, and is not intended to indicate whether or not a reaction between the acid and the lignocellulosic biomass occurs.

In general, the acidified lignocellulosic biomass will reside within a reactor zone of the pretreatment reactor for a time referred to as the residence time or pretreatment time. Notably, the residence time does not necessarily include the time required to ramp the temperature of the lignocellulosic biomass up to within a few degrees of the pretreatment temperature. The pretreatment time and pretreatment temperature may be dependent on the type of feedstock, the amount/type of pretreatment chemicals, and/or the desired degree of pretreatment. In one embodiment, the degree of pretreatment is selected to convert most of the hemicellulose component to soluble sugars (e.g., xylose, mannose, arabinose, and glucose), but little of the cellulose component to sugars (e.g., which may be hydrolyzed in a subsequent enzymatic hydrolysis). For example, in one embodiment, the degree of pretreatment is selected such that the amount of xylan hydrolyzed to xylose is greater than about 50 wt %, about 60 wt %, about 70 wt %, about 80 wt %, or about 90 wt %. In one embodiment, the level of pretreatment is selected to minimize production of sugar degradation products such as furfural and 5-hydroxymethyl furfural (HMF), which are potential fermentation inhibitors.

In one embodiment, the residence time is less than about 60 minutes. In one embodiment, the residence time is less than about 30 minutes. In one embodiment, the residence time is less than about 10 minutes. In one embodiment, the residence time is less than 7 minutes. In one embodiment, the residence time is greater than 30 seconds and less than 8 minutes. In one embodiment, the residence time is less than 7 minutes. In general, providing a residence time that is greater than about 2 minutes and less than about 10 minutes, when the temperature is greater than about 180° C. may be advantageous in terms of providing an efficient pretreatment without the production of a large number of potentially inhibitory sugar degradation products.

In one embodiment, sufficient acid is added to provide a final pH less than about 2. In one embodiment, sufficient acid is added to provide a final pH less than about 1.5. In another embodiment, sufficient acid is added to provide a pH less than about 1.25. In another embodiment, sufficient acid is added to provide a pH close to about 1.

In principle, the pH of the acidified biomass is measured after all of the acid has been added (e.g., prior to entering the pretreatment reactor, in the pretreatment reactor, or immediately after being discharged from the pretreatment reactor, depending if the acid is added prior to and/or while in the pretreatment reactor). In practice, the pH is often difficult to measure prior to pretreatment, due to the extremely thick nature of high consistency slurries. It may also be impractical to measure the pH before or during pretreatment when sulfur dioxide is added to the slurry as a gas in the pretreatment reactor. The pH is more readily measured after pretreatment, when the slurry is thinner. Accordingly, the term "final pH", as used herein, refers to the pH measured after pretreatment, at ambient temperature. In embodiments wherein the pretreated biomass has a large undissolved solids content and/or is relatively thick, the final pH is measured from a filtrate, pressate, or centrate of the sample (e.g., or other liquid from a solids-liquid separation). In another embodiment, wherein at least a portion of the acid is added in a heating chamber and/or in the pretreatment reactor, a sample of pretreated biomass (e.g., after flashing) is cooled and squeezed to express the liquid, from which the final pH is measured. In another embodiment, a sample of pretreated biomass (e.g., after flashing) is centrifuged to provide liquid from which the final pH is measured. The final pH of the pretreated material is measured prior to washing, dilution with water, and/or pH adjustment for enzymatic hydrolysis.

Although the final pH is generally related to the sulfur dioxide loading, it may also depend on other factors, including the type of feedstock and/or whether another acid (or base or salt) has been added. For example, if the lignocellulosic feedstock inherently has a high alkali content (e.g., potassium or calcium) that is not leached and/or washed away, a relatively high sulfur dioxide loading may be required to reach the desired pH (e.g., oat straw and corn stover are often associated with relatively high alkali content). The final pH may also depend on the severity of the cooking and/or the degree of flashing of the sulfur dioxide.

Notably, improved hydrolysis results have been found when the pretreatment is conducted such that the final pH of the pretreated material discharged from the pretreatment reactor is less than less than about 1.5, and more particularly, less than about 1.25 (i.e., measured at ambient temperature and from the filtrate, pressate, or centrate of the sample when the sample has a large undissolved solids content and/or is relatively thick).

In one embodiment, sufficient acid is added to provide a sulfur dioxide dosage of at least 6 wt % (e.g., weight of sulfur dioxide on weight of dry lignocellulosic biomass). In one embodiment, sufficient acid is added to provide a sulfur dioxide loading of at least 10 wt % (e.g., weight of sulfur dioxide on weight of dry lignocellulosic biomass). In one embodiment, sufficient acid is added to provide a sulfur dioxide loading of at least 15 wt % (e.g., weight of sulfur dioxide on weight of dry lignocellulosic biomass). In one embodiment, sufficient acid is added to provide a sulfur dioxide loading of at least 20 wt % (e.g., weight of sulfur dioxide on weight of dry lignocellulosic biomass).

The term "sulfur dioxide loading", as used herein, refers to the amount of sulfur dioxide fed to the pretreatment reactor per amount of dry lignocellulosic biomass fed to the pretreatment reactor, which is calculated from the grams of sulfur dioxide provided per gram of dry lignocellulosic biomass (e.g., as a weight percentage (wt %)). The term "sulfur dioxide loading", as used herein, may also refer the "equivalent sulfur dioxide loading", which is a term that may be used when the sulfur dioxide is added to the lignocellulosic biomass as sulfurous acid. In particular, the term "equivalent sulfur dioxide loading", as used herein, refers to the theoretical amount of sulfur dioxide provided, calculated from the grams of sulfurous acid added, expressed as equivalent sulfur dioxide provided per gram of dry lignocellulosic biomass.

In general, the effectiveness of the pretreatment may be at least partially dependent on the sulfur dioxide loading. For example, larger amounts of sulfur dioxide and/or sulfurous acid may provide a more digestible substrate (e.g., up to a point).

The instant disclosure recognizes that sulfur dioxide is volatile, and thus will generally partition between the vapour phase and the aqueous phase while resident in the pretreatment reactor, and thus that the amount of sulfur dioxide available for pretreatment may be dependent on the volume and/or configuration of the reactor and the headspace.

The term "headspace", as used herein, refers to the space in the sealed pretreatment reactor and/or system above and/or around the biomass (e.g. the biomass slurry). For example, if the biomass slurry has a relatively low consistency (e.g., about 6 wt %), the headspace includes the space in the pretreatment reactor above the liquid level, whereas if the biomass slurry has a relatively high consistency (e.g., about 15 wt % to about 67 wt %, and thus may be supported in a basket within the pretreatment reactor), the headspace may include the space in the pretreatment reactor that is above and/or around the biomass slurry. Notably, in each case, the headspace may include space one or more vapour reservoirs that are formed within and/or are in fluid connection with, the pretreatment reactor (e.g., as illustrated in U.S. Ser. No. 62/293,481, filed on Feb. 10, 2016, which is hereby incorporated by reference).

The term "vapour space", as used herein, refers to both the headspace and the void space in the biomass slurry. For example, if the biomass slurry has a relatively low consistency (e.g., below 15 wt %), the void space may include gas pockets or bubbles in the slurry, whereas if the biomass slurry has a relatively high consistency (e.g., above 15 wt %), the void space may include gas pockets, gas bubbles, and/or the space between wet particles. Advantageously, the vapour space may contain sulfur dioxide used to drive the pretreatment forward and/or provide a more efficient pretreatment. For example, the vapour space may contain sulfur dioxide that replaces sulfur dioxide, sulfurous acid, and/or the corresponding dissociation products, consumed by the pretreatment (e.g., to form lignosulfonates and/or other sulfonic acids) as the pretreatment progresses. In fact, while the effectiveness of pretreatment is at least partially dependent on the sulfur dioxide loading, it has been found that the effectiveness of the pretreatment may be also dependent on the amount of sulfur dioxide that remains within the aqueous slurry. This is reasonable, in that the sulfur dioxide in the headspace may not be in direct contact with the feedstock.

However, determining the concentration of sulfur dioxide within the slurry can be challenging. In principle, the partitioning of sulfur dioxide between the slurry and the headspace can be determined by measuring the concentration of sulfur dioxide in each phase. In practice, this is very difficult in a high-temperature pretreatment reactor. Alternately, in principle, the partitioning of sulfur dioxide between vapor and liquid phases may be calculated based on the vapor-liquid equilibrium of the system, at the system temperature. In practice, this may also be difficult because of the complexity of the chemical species that are present and the lack of confirmed data on which to base the calculation.

In accordance with one embodiment, the proportion of sulfur dioxide in the slurry phase is estimated to be equal to the proportion of the pretreatment reactor volume that is occupied by the slurry, at the relevant range of pretreatment temperatures. In fact, this appears to be in line with data for pure $SO_2$/water systems. For example, assuming that the Henry's Law constant for $SO_2$/water at 210° C. is 1.4*exp((2900)(1/483.15−1/298.15))=0.034 Mol/Kg bar, at 1 bar $SO_2$ partial pressure, the solubility of $SO_2$ in water is 0.034 Mol/kg. With the density of water at 210° C. equal to 0.853 kg/L, the dissolved $SO_2$ concentration is (0.034)(0.853)=0.029 mol/L. In the vapor phase, if we assume an ideal gas, then the $SO_2$ concentration is (1 mole/22.4 L)(273.15/483.15)=0.025 mol/L which is very comparable to the concentration in the water.

It has been found that, given that the dissolved $SO_2$ concentration and vapour phase $SO_2$ concentration are similar at 210° C., and given that the effectiveness of the pretreatment may be more dependent on the amount of sulfur dioxide that remains within the aqueous slurry, the effectiveness of the pretreatment is dependent on the product of the sulfur dioxide loading and the proportion of the pretreatment reactor volume that is occupied by the slurry, $V_s$. In particular, it has been found that the pretreatment is particularly effective when the sulfur dioxide loading, as corrected with the ratio of $V_s$ to $V_r$, is between certain values. More specifically, it has been found that improved pretreatment is achieved when the volume adjusted sulfur dioxide loading, which is equal to the product of the total sulfur dioxide loading and the ratio of $V_s$ to $V_r$, is greater than a certain value.

Notably, the sulfur dioxide loading, is based on the amount of sulfur dioxide and/or sulfurous acid fed to the pretreatment reactor (with or separately from the lignocellulosic biomass), and thus does not include sulfur dioxide and/or sulfurous acid used to impregnate the biomass, but not carried forward into the pretreatment reactor. In embodiments wherein there are two tandem pretreatment reactors, the sulfur dioxide loading may be the same or different for the two reactors. For example, in one embodiment, a first pretreatment reactor is associated with a first sulfur dioxide loading, whereas a second downstream pretreatment reactor is associated with a second higher sulfur dioxide loading (e.g., is fed unreacted $SO_2$ from the first pretreatment reactor and additional top-up $SO_2$ fed only to the second pretreatment reactor). In general, the preferred range for the volume adjusted sulfur dioxide loading (e.g., greater than 0.8 wt %), only needs to be provided for one pretreatment reactor in order to provide improved pretreatment.

Given that $V_r=V_s+V_h$, where $V_h$ is the volume of the headspace, it is apparent that low sulfur dioxide loadings and/or relatively large headspaces may result in the volume adjusted sulfur dioxide loading being too low to provide an effective pretreatment. In particular, the grams of sulfur dioxide fed to pretreatment per gram of dry lignocellulosic biomass fed to the pretreatment reactor may need to be selected in dependence upon the slurry volume in (e.g., the working volume or operating volume) the pretreatment reactor. For example, the grams of sulfur dioxide fed to pretreatment per gram of dry lignocellulosic biomass may need to be increased when there is a relatively large headspace (e.g., as typically found in steam guns, wherein $V_s/V_r$ is typically under 0.1, and often under 0.05).

In addition to selecting the volume adjusted sulfur dioxide loading to be above a certain value, it has been also found that the pretreatment may be further improved by also considering the moisture content of the acidified lignocellulosic biomass. For example, the relatively dilute conditions used to encourage mixing within Parr-type reactors (i.e., a water content of more than 90%) may dilute the sulfur dioxide/sulfurous acid excessively, thus potentially reducing the effectiveness of the pretreatment, whereas the relatively dry conditions commonly used when impregnating wood chips (e.g., moisture content less than 60%) may provide insufficient water for an effective pretreatment. In fact, the amount of water present during pretreatment is believed to affect the effectiveness of pretreatment. Without being bound by theory, the amount of water present may affect how much sulfur dioxide is in solution relative to the gas phase, whether a concentrated amount of sulfurous acid is in close proximity to and/or able to penetrate the fibres, the efficiency of the hydrothermal effect, the sulfonation of (or other reactions with) the lignin, and/or the dissolution of lignin. In addition, limiting the water content to below a certain value may provide a more efficient and rapid heat-up to the pretreatment temperature, thus providing a more uniform cook, which is likely to increase effectiveness of the pretreatment.

In fact, it has been found that improved hydrolysis has been achieved by balancing: (i) effective concentration of sulfur dioxide in the lignocellulosic biomass slurry; (ii) the effective sulfur dioxide dosage; (iii) the moisture content of the lignocellulosic biomass slurry in pretreatment; and (iv) the final pH pretreatment. Notably, both the effective concentration of sulfur dioxide in the lignocellulosic biomass slurry and the effective sulfur dioxide dosage are dependent on the ratio of the slurry volume ($V_s$) and total volume ($V_r$) of the pretreatment reactor. Each of these parameters is discussed in further detail, as follows.

(i) Effective Concentration of Sulfur Dioxide in Slurry

The estimation of the sulfur dioxide concentration in the slurry starts by relating all of the sulfur dioxide present in the pretreatment reactor to the weight of water in the slurry in the pretreatment reactor. In particular, the sulfur dioxide concentration in the slurry (i.e., $SO_{2(Total,water)}$), is calculated from the total amount of sulfur dioxide present within the pretreatment reactor and the amount of water present in the pretreatment reactor (i.e., water added to the lignocellulosic biomass and/or water inherently present in the lignocellulosic biomass, but excluding steam added to heat the lignocellulosic biomass) and is calculated from the grams of sulfur dioxide present per gram of moisture present in the slurry (e.g., as a percentage (wt %)). In one embodiment, the grams of sulfur dioxide present within the reactor is determined from the sulfur dioxide loading. In another embodiment, wherein at least some sulfur dioxide is prevented from leaving the pretreatment reactor as at least some of the pretreated material is discharged, the grams of sulfur dioxide present within the reactor is determined from both the sulfur dioxide loading and the grams of sulfur dioxide prevented from leaving the reactor. The grams of moisture present may be determined from the solids consistency and total weight of the solids fed to the pretreatment reactor. Since sulfur dioxide is volatile, it will partition between the vapour phase (e.g., in the headspace) and the liquid phase (e.g., in the aqueous slurry), and thus, this concentration may be corrected to account for the volume of headspace. The "volume adjusted" sulfur dioxide slurry concentration, also referred to as the "effective concentration of sulfur dioxide in the slurry", or $SO_{2(VA,water)}$, is calculated as follows.

$$SO_{2(VA,water)} = SO_{2(Total,water)} \frac{V_s}{V_r} \tag{1}$$

As indicated in Equation (2), improved hydrolysis results have been found when the effective $SO_2$ concentration of sulfur dioxide in the slurry, $SO_{2(VA, water)}$, is between about 0.25 wt % and about 1.5 wt %.

$$SO_{2(VA,water)} = SO_{2(Total,water)} \frac{V_s}{V_r} = 0.25 \text{ wt \% to } 1.5 \text{ wt \%} \tag{2}$$

(ii) Effective Sulfur Dioxide Dosage

As discussed above, the sulfur dioxide loading is obtained from the total amount of sulfur dioxide fed to the pretreatment reactor and the amount of solids (on a dry basis) fed to the pretreatment rector, and is calculated from the grams of sulfur dioxide provided per gram of dry lignocellulosic biomass provided (e.g., as a percentage (wt %)).

The sulfur dioxide dosage, $SO_{2(Total,dry)}$, is obtained from the total amount of sulfur dioxide present within the pretreatment reactor and the amount of solids (on a dry basis) present in the pretreatment reactor, and is calculated from the grams of sulfur dioxide present per gram of dry lignocellulosic biomass present (e.g., as a percentage (wt %)). In one embodiment, the grams of sulfur dioxide present per gram of dry lignocellulosic biomass present is equivalent to the sulfur dioxide loading. In another embodiment, the grams of sulfur dioxide present per gram of dry lignocellulosic biomass present is the sulfur dioxide loading corrected to include the grams of sulfur dioxide prevented from exiting the pretreatment reactor as pretreated material is discharged from the reactor. In one embodiment, the grams of sulfur dioxide prevented from leaving the pretreatment reactor is estimated from the volume of the headspace within the reactor and a concentration of sulfur dioxide in the headspace (e.g., which may be determined by measuring the sulfur dioxide partial pressure and/or another method).

While the sulfur dioxide dosage, $SO_{2(Total,dry)}$ may be related to the effectiveness of pretreatment, it has been found that it better to use the "volume adjusted sulfur dioxide dosage", $SO_{2(VA,dry)}$, calculated as follows.

$$SO_{2(VA,dry)} = SO_{2(Total,dry)} \frac{V_s}{V_r} \tag{3}$$

The "volume adjusted sulfur dioxide dosage", $SO_{2(VA,dry)}$, may be also referred to herein as the "effective sulfur dioxide dosage".

Referring to Equation (4), improved hydrolysis results have been found when the effective sulfur dioxide dosage, $SO_{2(VA,dry)}$, is >0.8 wt %.

$$SO_{2(VA,dry)} = SO_{2(Total,dry)} \frac{V_s}{V_r} > 0.8 \text{ wt \%} \tag{4}$$

Referring to Equation (5), improved hydrolysis results have been found when the effective sulfur dioxide dosage, $SO_{2(VA,dry)}$, is greater than 1 wt %.

$$SO_{2(VA,dry)} = SO_{2(Total,dry)} \frac{V_s}{V_r} > 1 \text{ wt \%} \qquad (5)$$

In one embodiment, more improved pretreatment is achieved when the volume adjusted sulfur dioxide dosage $(SO_{2(VA,dry)})$ is greater than 2 wt %. In one embodiment, improved pretreatment is achieved when the volume adjusted sulfur dioxide dosage $(SO_{2(VA,dry)})$ is between about 0.8 wt % and about 8 wt %.

(iii) Moisture Content of the Lignocellulosic Biomass Slurry

As discussed above, improved pretreatment is provided when both the volume adjusted sulfur dioxide dosage and the moisture content of the lignocellulosic biomass are within predetermined limits. In particular, improved pretreatment is observed when the moisture content of the lignocellulosic biomass is limited to between about 49 wt % and about 85 wt % (e.g., a consistency between about 51 wt % and about 15 wt %). Without being bound by theory, providing an effective sulfur dioxide dosage, $SO_{2(VA,dry)}$, that is greater than about 0.8% with a sufficient moisture content, may provide sufficient $SO_2$ to sulfonate a significant fraction of the lignin, which may improve the effectiveness of the pretreatment.

The effective sulfur dioxide dosage on solids, $SO_{2(VA, dry)}$, and the effective concentration of sulfur dioxide in the slurry, $SO_{2(VA,water)}$, are related to the consistency of the lignocellulosic biomass slurry, $C_f$, as follows.

$$SO_{2(VA,dry)} = SO_{2(VA,water)} \frac{(100 - Cf)}{Cf} \qquad (6)$$

As discussed above, the amount of water present in pretreatment has been found to affect the effectiveness of pretreatment, and thus hydrolysis. For example, the amount of water present may affect how much sulfur dioxide is in solution relative to the gas phase, whether a concentrated amount of sulfurous acid is in close proximity to the fibres, the sulfonation of (or other reactions with) the lignin, and/or the dissolution of lignin. For example, at relatively high consistencies (i.e., above about 51 wt %) there may be insufficient water to dissolve lignin and/or provide sufficient moisture for an effective pretreatment, whereas at relatively low consistencies (i.e., below about 15 wt %), there may be too much water to efficiently and/or economically bring the lignocellulosic biomass to the pretreatment temperature. In addition, a relatively low consistency may affect the effective $SO_2$ concentration in the slurry, $SO_{2(VA, water)}$. For example, a relatively high water content may excessively dilute the $SO_2$ in the slurry, thus reducing the effective $SO_2$ concentration in the slurry to below 0.25 wt % (e.g., improved pretreatment has been found for values between about 0.25 wt % and about 1.5 wt %). In addition, a relatively low consistency may increase the pH to above the optimal range.

(iv) Pretreatment pH

In practice, we have found that relatively good hydrolyses are provided when the pH of the slurry at the end of pretreatment is less than about 1.5. In addition, it has been found that providing an effective sulfur dioxide dosage on solids that is more than 0.8 wt % and an effective sulfur dioxide slurrying concentration that is between 0.25 wt % and 1.5 wt %, for wheat straw, typically yields a pH that is less than about 1.5 at the end of pretreatment.

Notably, these pretreatments conditions are expected to provide improved hydrolysis for most lignocellulosic feedstocks pretreated at temperatures between about 170° C. and about 230° C. for a duration between about 30 seconds and 10 minutes, and in particular, for non-woody lignocellulosic biomass pretreated at temperatures between about 180° C. and about 220° C. for a duration between about 30 seconds and 10 minutes.

If, however, the pH of the slurry at the end of pretreatment is greater than 1.5, this may be an indication that the pretreatment conditions for the selected feedstock should be adjusted in order to provide improved hydrolysis. For example, some lignocellulosic feedstocks, such as softwood, may require more sulfur dioxide and/or sulfurous acid in order to provide a pH less than about 1.5. Optionally, the pH may be reduced by the addition of another acid, such as sulfuric acid, in addition to the sulfur dioxide/sulfurous acid.

As discussed above, a relatively effective pretreatment may be achieved when the pretreatment conditions are selected to balance: (i) effective concentration of sulfur dioxide in the lignocellulosic biomass slurry; (ii) the effective sulfur dioxide dosage; (iii) the moisture content of the lignocellulosic biomass in pretreatment; and (iv) the final pH of pretreatment. More specifically, improved pretreatment may be achieved when the effective $SO_2$ slurry concentration is between about 0.25 wt % and about 1.5 wt %, the effective $SO_2$ dosage above about 0.8 wt %, and the moisture content of the slurry between about 49 and 85 wt %, and the final pH is below about 1.5 (e.g., as measured at the end of the pretreatment).

These conditions are further discussed with reference to FIG. 2, which shows how the effective $SO_2$ dosage, $SO_{2(VA, dry)}$, and effective $SO_2$ slurry concentration, $SO_{2(VA, wet)}$, can be used to help determine the preferred pretreatment conditions (i.e., according to one embodiment) and/or how they relate to consistency of the slurry.

As discussed above, the effective sulfur dioxide dosage on solids, $SO_{2(VA,dry)}$, and the effective concentration of sulfur dioxide in the slurry, $SO_{2(VA,water)}$, are related to the consistency of the lignocellulosic biomass slurry, $C_f$, according to Eq. (6).

Figure 2:
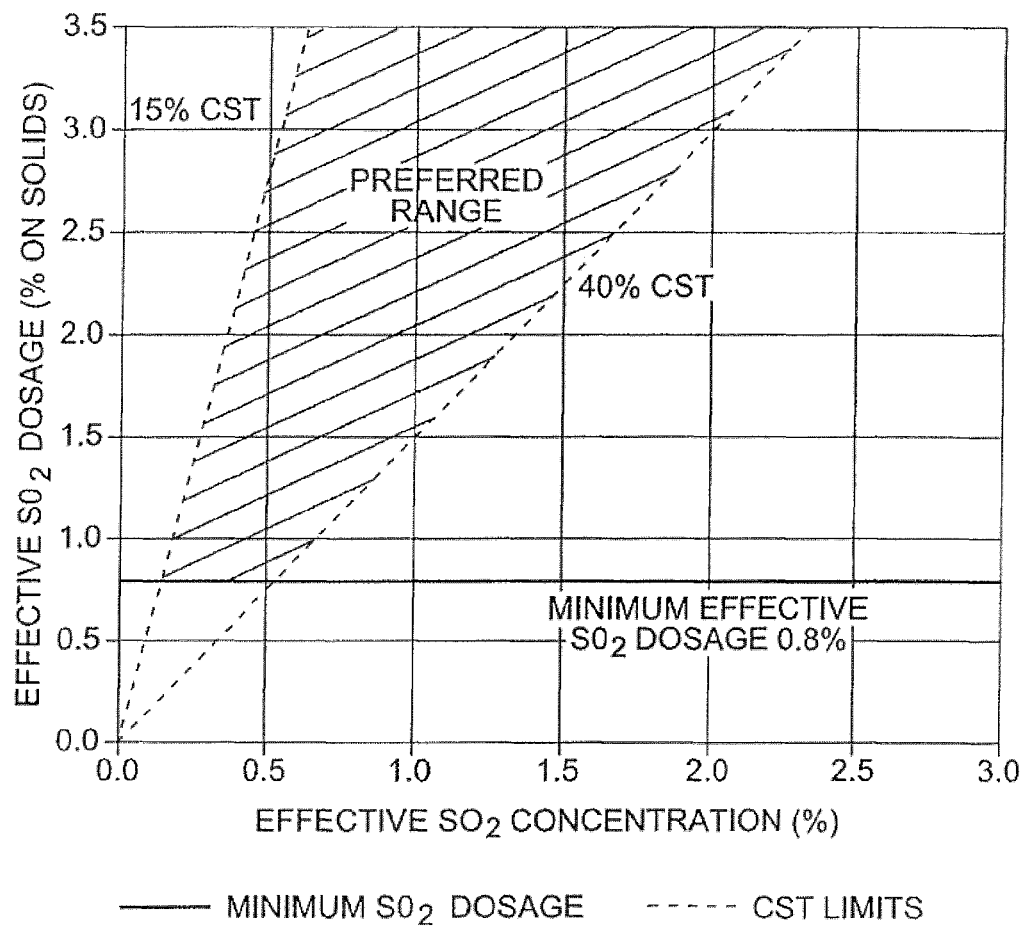
FIG. 2 is a graph illustrating various pretreatment conditions in accordance with one embodiment of the invention.

Referring to FIG. 2, consistencies corresponding to 15 wt % and 40 wt % are illustrated by the linear dashed lines (---). In one embodiment, the effective sulfur dioxide dosage on solids, $SO_{2(VA, dry)}$, and the effective concentration of sulfur dioxide in the slurry, $SO_{2(VA,water)}$, are selected such that they correspond to a value on one of the dashed lines or between the two dashed lines (e.g., which are labeled as consistency (cst) limits to illustrate that in this embodiment the preferred consistency range is from 15 wt % to 40 wt %). For example, in one embodiment, the conditions are selected such that the effective sulfur dioxide dosage on solids, $SO_{2(VA,dry)}$, is selected in dependence upon the effective concentration of sulfur dioxide in the slurry, $SO_{2(VA,water)}$, such that the corresponding point on the graph is between the dashed lines. Notably, the effective $SO_2$ dosage on solids corresponding to 0.8 wt % is shown by the solid line (e.g., labeled the minimum effective $SO_2$ dosage to illustrate that in this embodiment the preferred value of the effective $SO_2$ dosage on solids is equal to or greater than 0.8 wt %). In another embodiment, the preferred value of the effective $SO_2$ dosage on solids (e.g., the product of sulfur dioxide dosage and $V_s/V_r$) is greater than about 1.0 wt %.

In one embodiment, the lignocellulosic biomass fed to the pretreatment reactor has a consistency between 14.5 wt % and 40.5 wt %, while the product of sulfur dioxide dosage and $V_s/V_r$ (e.g., the effective $SO_2$ dosage on solids) is greater than 0.8 wt %. In another embodiment, the consistency of the acidified lignocellulosic biomass to be treated in the pretreatment reactor is between 14.5 wt % and 51 wt %, while the product of sulfur dioxide dosage and $V_s/V_r$ (e.g., the effective $SO_2$ dosage on solids) is greater than 0.8 wt %. In one embodiment, the lignocellulosic biomass fed to the pretreatment reactor has a consistency between 14.5 wt % and 51 wt %, while the product of sulfur dioxide dosage and $V_s/V_r$ (e.g., the effective $SO_2$ dosage on solids) is greater than 1 wt %. In one embodiment, the consistency of the acidified lignocellulosic biomass to be treated in the pretreatment reactor is between 14.5 wt % and 40.5 wt %, while the product of sulfur dioxide dosage and $V_s/V_r$ (e.g., the effective $SO_2$ dosage on solids) is greater than 1 wt %.

In general, if sulfuric acid is added to further reduce the pH of the pretreatment, the sulfuric acid will be added in addition to the required dosage and concentration of $SO_2$, and does not change the limits of solids consistency, effective $SO_2$ dosage, and/or $SO_2$ slurry concentration. In general, whether the acid added includes $SO_2$ or $SO_2$ and an additional acid, these conditions result in a pH at the end of pretreatment, measured at ambient temperature, less than about 1.5, or between about 0.5 and 1.5.

Advantageously, selecting the $SO_2$ dosage on solids (i.e., $SO_{2(Total,dry)}$), moisture level during pretreatment, final pH of pretreatment, and/or ratio of slurry volume/total volume of pretreatment reactor such that $SO_{2(TA,dry)}$ as a function of $SO_{2(VA,wet)}$ is within the range defined by FIG. 2, provides a comprehensive approach to maximizing effectiveness of pretreatment. This approach is based on the recognition that each of $SO_2$ dosage on solids (i.e., $SO_{2(Total,dry)}$), moisture content, final pH, and/or the ratio of slurry volume/total volume of the pretreatment reactor may not only affect the effectiveness of the pretreatment on its own, but that the effectiveness may be improved by selecting at least some of these parameters in dependence upon the others. Notably, the dependency of these parameters on the others has not been previously recognized. In particular, the dependence of the required $SO_2$ dosage (e.g., $SO_{2(Total,dry)}$) on the ratio of the slurry volume of the pretreatment reactor, $V_s$, to the total volume of the pretreatment reactor, $V_r$ (e.g., $V_s/V_r$) has not been recognized. Unfortunately, this has led to conflicting results in terms of what conditions have been reported to provide the most effective pretreatment. For example, one group may conclude that the most effective pretreatment results when the $SO_2$ loading is 5%, whereas another group may report that the most effective pretreatment results when the $SO_2$ loading is 2%. In contrast, by selecting each of the concentration of sulfur dioxide in the lignocellulosic biomass slurry and/or the sulfur dioxide dosage in dependence upon $V_s/V_r$, a more complete and/or accurate prediction of the effectiveness of the pretreatment may be achieved. Advantageously, this may improve the performance and consistency of $SO_2$ as a pretreatment acid, thereby resulting in a better process for the commercial production of ethanol.

By providing a more effective pretreatment, the subsequent enzymatic hydrolysis will be more effective. Although the amount of xylose produced during pretreatment may be used as a rough indication of the degree of pretreatment, a more accurate assessment of the effectiveness of pretreatment is obtained by looking at the enzymatic hydrolysis. For example, the effectiveness of pretreatment may be realized by a reduction in enzyme usage, a higher cellulose conversion, and/or a shorter hydrolysis time, in enzymatic hydrolysis. By selecting the effective $SO_2$ dosage and slurry concentration to be within the ranges defined by FIG. 2, it has been found that the enzymatic hydrolysis requires ¼ to ½ the amount of enzyme to convert the cellulose to glucose, or that the xylose yield may be increased by 3% to 6%, relative to a pretreatment that uses conditions outside this range. Since the cost of enzymes is a significant contributor to the cost of the process, this may advance the commercialization of $SO_2$ catalyzed pretreatment.

As discussed above, each of the (i) effective concentration of sulfur dioxide in the lignocellulosic biomass slurry and (ii) the effective sulfur dioxide dosage is dependent on the slurry volume ($V_s$) and total volume ($V_r$) of the pretreatment reactor. In fact, while volume of the headspace conventionally has been ignored when determining the conditions for effective pretreatment, it has been found that the volume of the headspace ($V_h$) may be relatively important and/or should at least considered when selecting the $SO_2$ dosage and/or pretreatment moisture level. In fact, it has been found that the effectiveness of the pretreatment, measured as the amount of xylose produced, is dependent on headspace volume and/or ratio of $V_{s\ to}$ Vr. For example, see Example 11.

In general, any pretreatment reactor that provides the selected conditions for pretreatment may be used. For example, in one embodiment, the pretreatment conditions (e.g., temperature, pH, sulfur dioxide dosage, and/or residence time) are selected to maximize the hydrolysis of xylan and to minimize the hydrolysis of cellulose to glucose. For example, in one embodiment, the pretreatment conditions are selected such that pretreatment temperature is above 180° C., and more specifically above 185° C., and that the pH at the end of pretreatment (e.g., final pH) is under 1.5.

In general, the pretreatment reactor may be operated in continuous mode, batch mode, or semi-batch mode. For example, the pretreatment reactor may be a vertical reactor, a horizontal reactor, or an inclined reactor. In one embodiment, the pretreatment reactor is a vertical reactor and includes a rotary sweeper (not shown) that conveys the pretreated biomass to a screw conveyor so that it can be discharged via a blow-out valve. In one embodiment, the pretreatment reactor is a horizontal reactor that includes a screw conveyor that feeds the pretreated biomass to the blow-out valve.

In one embodiment, the pretreatment reactor is a horizontal reactor and the biomass to be treated therein has a consistency between about 15 wt % and about 51 wt %. In one embodiment, the pretreatment reactor is a horizontal reactor and the biomass to be treated therein has a consistency between about 20 wt % and about 35 wt %.

In embodiments wherein biomass having a consistency between about 15 wt % and about 51 wt % is fed to the pretreatment reactor, and wherein the pretreatment 10 does not significantly break down the cellulose component of the biomass (e.g., although some or all of the hemicellulose component may be hydrolyzed), the biomass discharged from the pretreatment reactor may have a relatively high consistency (e.g., greater than about 15 wt % or even greater than about 20 wt %) and may be relatively hot (e.g., at a temperature greater than about 170° C. and more commonly greater than about 180° C. prior to any flashing).

In one embodiment, the pretreatment reactor is a horizontal reactor. Advantageously, the use of a horizontal reactor may increase the amount of biomass that is in close proximity to sulfur dioxide in the vapour space and/or headspace of the pretreatment reactor. In particular, since the vapour space may contain excess sulfur dioxide that may drive the pretreatment forward and/or may provide a more efficient pretreatment, and since the horizontal configuration allows more lignocellulosic biomass to be adjacent to and/or closer to the vapour space, a more rapid, complete, uniform and/or efficient pretreatment may be achieved. For example, the horizontal pretreatment reactor may provide better mass transfer. In one embodiment, the horizontal pretreatment reactor includes an elongated chamber including a screw conveyor. Optionally, the horizontal pretreatment reactor includes a plurality of inlets for injecting steam, sulfur dioxide, and or sulfurous acid, into the elongated heating chamber.

As discussed above, providing a relatively large headspace may improve the effectiveness of the pretreatment. For example, providing a relatively large headspace volume may be advantageous for maintaining the pH of the lignocellulosic biomass within a predetermined range during the pretreatment and/or otherwise maintaining a constant amount of acid near the lignocellulosic biomass. For example, if the acid is consumed as the pretreatment progresses, the vapour space, which contains excess sulfur dioxide, may function as a sulfur dioxide and/or sulfurous acid reserve to help drive the reaction and/or prevent localized depletion of the acid. Notably, the use of a horizontal pretreatment reactor is particularly advantageous when the lignocellulosic biomass has a relatively high consistency at the inlet to the pretreatment reactor (e.g., a consistency greater than about 15 wt %), since a relatively large vapour space may allow the vapour phase sulfur dioxide to impregnate the biomass more uniformly.

Optionally, the pretreatment reactor is provided with a charge of sulfur dioxide as described in as illustrated in U.S. Ser. No. 62/293,481, filed on Feb. 10, 2016, which is hereby incorporated by reference for the purposes of describing such pretreatment reactors. For example, in one embodiment, the pretreatment system includes a pretreatment reactor that provides a charge of sulfur dioxide (e.g., maintains a supply of sulfur dioxide within or available to the reactor during the continuous pretreatment cycle, as described in U.S. Ser. No. 62/293,481). In this case, the sulfur dioxide loading may not accurately reflect the amount of sulfur dioxide within the reactor, and it may be particularly advantageous to refer to and/or determined the sulfur dioxide dosage. For example, the sulfur dioxide dosage may include the amount of sulfur dioxide fed to the pretreatment reactor plus the amount of sulfur dioxide retained within the reactor as a charge (e.g., within the headspace) while the pretreated feedstock exits the pretreatment reactor, per amount of dry lignocellulosic biomass fed to the reactor, expressed as a percentage. In one embodiment, the sulfur dioxide dosage is calculated from the sulfur dioxide loading as corrected to include the sulfur dioxide charge. For example, in one embodiment, the sulfur dioxide charge may be calculated using measured and/or calculated concentrations of sulfur dioxide within the headspace (e.g., determined using sulfur dioxide partial pressure measurements). In embodiments where there is no sulfur dioxide charge present the sulfur dioxide loading and sulfur dioxide dosage will be typically the same.

In one embodiment, the pretreatment reactor is a horizontal reactor for treating lignocellulosic biomass having a consistency greater than 10 wt %, greater than about 15 wt %, or greater than about 20 wt %.

In one embodiment, the sulfur dioxide dosage is selected in dependence upon the vapour space volume and/or consistency of the lignocellulosic biomass. Selecting the sulfur dioxide dosage in dependence upon the vapour space volume is advantageous in that the concentration of the sulfur dioxide available in the vapour phase may be sufficiently high to drive the reaction, replenish sulfur dioxide in solution, and/or maintain a low pH. In general, there may be some compromise when selecting headspace volume. For example, a relatively small headspace may concentrate vapour phase sulfur dioxide close to the lignocellulosic biomass, whereas a larger headspace may contain a larger amount of vapour phase sulfur dioxide. In one embodiment, the headspace volume is between about 50% and about 90% the volume of the pretreatment reactor. In another embodiment, the headspace volume is between about 60% and about 85% the volume of the pretreatment reactor. In another embodiment, the headspace volume is between about 50% and about 80% the volume of the pretreatment reactor. Providing a relatively large vapour space volume advantageously allows vapour phase sulfur dioxide to fill the void area, which may then function as localized sulfur dioxide reservoir(s).

Providing a headspace volume that is between about 60% and about 80% the volume of the pretreatment reactor (i.e., such that $V_s/V_r$ is between about 0.20 and about 0.4) advantageously allows an effective sulfur dioxide dosage of 0.8% to be achieved using a sulfur dioxide dosage between 4 wt % and 2 wt % (e.g., compared to a sulfur dioxide dosage of 8 wt %, which is required when $V_s/V_r$ is about 0.1, as may be found in steam guns). In other words, selecting the appropriate headspace volume (e.g., or $V_s/V_r$) may allow a reduction in the amount of sulfur dioxide used by ½, or more, for the substantially same pretreatment effectiveness.

Referring again to Eq. 6, an effective sulfur dioxide dosage of 0.8 wt % will correspond to an effective sulfur dioxide slurry concentration of 0.25 wt % and 1.5 wt % when the consistency, $C_f$, is 24 wt % and 65 wt %, respectively.

In one embodiment, the ratio of volume of slurry to the volume of reactor is less than about 0.8. In one embodiment, the ratio of the volume of the slurry to the volume of reactor is between about 0.1 and about 0.6. In one embodiment, the ratio of the volume of the slurry to the volume of the reactor is between about 0.15 and 0.5. In one embodiment, a ratio outside of these ranges is provided.

The above-described slurry and/or reactor volumes may be calculated and/or measured. In one embodiment, slurry volume is measured at the start of pretreatment (e.g., at time zero and/or close to the biomass input end of a continuous pretreatment reactor), since these values may change as the pretreatment progresses. In one embodiment, the slurry volume is calculated as the weight of the slurry (kg) divided by the density of the slurry, for which we assume the density of water, 1000 $kg/m^3$. In one embodiment, wherein the reactor volume is not known, the reactor volume is calculated by determining the volume of water required to fill the reactor.

Flashing

After the pretreatment time has elapsed, the pretreated lignocellulosic biomass may be discharged from the pretreatment reactor. In one embodiment, this includes reducing the pressure on the pretreated lignocellulosic biomass. Alternatively, the pressure may be reduced at a stage further downstream. In one embodiment, the pressure is reduced by flashing 20. For example, in one embodiment, the pressure is reduced using one or more flash tanks in fluid connection with the pretreatment reactor.

In general, when the pressure on a hot, high-pressure, stream is reduced (e.g., by being discharged into a lower pressure tank referred to as a flash tank), the stream temperature drops, which releases heat that evaporates a volatile portion of the stream (i.e., to produce a flash stream). In general, the temperature of the cooled stream is related to the pressure in the flash tank. For example, if the flash tank is at atmospheric pressure, the stream may be cooled to about 100° C.

In one embodiment, the pretreated lignocellulosic biomass is discharged from the pretreatment reactor into a flash tank that provides a flash stream including steam and sulfur dioxide and a condensate stream comprising a cooled pretreated lignocellulosic biomass composition. For example, the cooled pretreated lignocellulosic biomass composition may comprise undissolved solids such as unconverted cellulose and/or insoluble lignin, and/or soluble compounds such as sugars (e.g., xylose, glucose, and arabinose), organic acids (e.g., acetic acid and glucuronic acid), soluble lignin (e.g., including soluble products of reactions between sulfur dioxide/sulfurous acid and lignin, such as sulfonic acids and lignosulfonic acids), soluble sugar degradation products (e.g., furfural, which may be derived from C5 sugars, and hydroxymethylfurfural (HMF), which may be derived from C6 sugars) and/or one or more salts (e.g., sulfite salts). Notably, although acetic acid, furfural, and/or HMF may be potential inhibitors to fermentation, the use of sulfur dioxide and/or sulfurous acid may produce lower concentrations of these potential inhibitors. More specifically, the use of a relatively high dosage of sulfur dioxide and a pretreatment temperature above 185° C. has been found to provide a relatively low amount of inhibitors and/or inactivating compounds. In one embodiment, less than about 5% weight of furfural relative to the weight of feedstock may be produced. For example, in one embodiment, less than 2.5 g/L of furfural is produced. In another embodiment, less than 1.5 g/L of furfural is produced.

In addition, the use of a relatively high dosage of sulfur dioxide and a pretreatment temperature above 185° C. has been found to provide a relatively large amount of xylose. In particular, the pretreatment may be conducted at a temperature and for a time selected to produce xylose in an amount that is at least 70% or 75% of the potentially available xylose (e.g., on a weight by weight basis). The amount of potentially available xylose is determined by carbohydrate assay.

In general, the pretreated biomass composition may be fed to enzymatic hydrolysis 30 with washing, with minimal washing, or without washing. While washing may remove potential inhibitors and/or inactivators, thus increasing enzyme efficiency, it may also remove fermentable sugars, thus reducing ethanol yield. Since the combination of high sulfur dioxide dosage and a pretreatment temperature above 185° C. may produce lower concentrations of potential inhibitors and/or inactivators, the process described herein may not require washing, dilution, and/or other processing that removes inhibitors in order to provide a high ethanol yield. Accordingly, in one embodiment, the pretreated feedstock composition is fed to an enzymatic hydrolysis with little or no washing or other processing that removes a significant amount of soluble compounds (e.g., such as lime precipitation). For example, in one embodiment, the pretreated feedstock composition is fed to enzymatic hydrolysis such that most of the soluble compounds are transferred to enzymatic hydrolysis with most of the undissolved solids. In one embodiment, the concentration of soluble compounds fed to the enzymatic hydrolysis is at least 20% of the concentration of dissolved solids in the pretreated feedstock composition. In one embodiment, the concentration of soluble compounds fed to the enzymatic hydrolysis is at least about 50% of the concentration of soluble compounds in the pretreated feedstock composition. In one embodiment, at least about 55%, at least about 60%, at least about 65%, at least about 70%, at least about 75%, at least about 80%, at least about 85% or at least 90%, on a weight/volume basis, of the soluble compounds in the pretreated feedstock composition are fed to the enzymatic hydrolysis. In one embodiment, the concentration of soluble compounds in a sample is determined by vacuum filtering the sample through glass microfiber filter paper of pore size 1.6 micron, collecting and weighing the filtrate, drying the filtrate overnight at 105° C., and weighing the contents using an analytical balance. The concentration of soluble compounds may then be expressed as the grams of dry contents per gram of filtrate or grams, of dry contents per liter of filtrate if the density of the filtrate is measured.

According to one embodiment, the concentration of xylose in the stream fed to the enzymatic hydrolysis is at least 50% of the concentration of xylose in the pretreated lignocellulosic biomass composition. According to another embodiment, the concentration of xylose in the stream fed to the enzymatic hydrolysis is at least about 60% of the concentration of xylose in the pretreated lignocellulosic biomass composition. According to another embodiment, the concentration of xylose in the stream fed to the enzymatic hydrolysis is at least about 70% of the concentration of xylose in the pretreated lignocellulosic biomass composition. According to another embodiment, the concentration of xylose in the stream fed to the enzymatic hydrolysis is at least 80% of the concentration of xylose in the pretreated lignocellulosic biomass composition. The concentration of xylose may be determined using HPLC (e.g., after neutralization). Providing little or no washing of the pretreated feedstock composition is advantageous in that it requires less process water and provides a simpler process.

Optionally, the pretreated lignocellulosic biomass composition is subjected to a temperature and/or pH adjustment in order to bring the temperature and/or pH of the pretreated composition into a range compatible with enzyme(s) used in the enzymatic hydrolysis 30 and/or microorganisms used in the fermentation 40. For example, depending upon the pH of the pretreated lignocellulosic biomass composition, a base (e.g., calcium hydroxide, potassium hydroxide, sodium hydroxide, ammonia gas, etc.) may be added to increase the pH of and/or substantially neutralize the pretreated biomass composition. The base may be added to the pretreated biomass composition after it is cooled, before cooling, and/or as it is cooled. For example, in one embodiment, lime is added to the pretreated material before or after flashing. In one embodiment, lime is added to the pretreated material after a minimal washing. In general, the addition of base will be upstream and/or simultaneous with enzyme addition. If base is added downstream of enzyme addition, the contact time of the enzyme with the relatively acidic pretreated biomass composition may be minimized to avoid enzyme inactivation.

In general, the pH at which an enzyme is reasonably active depends on the particular enzyme(s) utilized in the cellulose hydrolysis, and may be determined readily by those of skill in the art. For example, many cellulases may have an optimum pH range between about 4 and about 7, and often about 5. In one embodiment, sufficient pH adjusting chemical is added to bring the pH of the pretreated biomass composition to between about 4 and about 8. In another embodiment, sufficient pH adjusting chemical is added to bring the pH of the pretreated biomass composition to between about 4.5 and about 6.

In general, the temperature at which an enzyme is reasonably active depends on the particular enzyme(s) utilized in the cellulose hydrolysis, and may be determined readily by those of skill in the art. For example, conventional cellulases often have an optimum temperature range between about 40° C. and about 60° C., and more commonly around 50° C., whereas thermostable and/thermophilic enzymes may have optimum temperatures that are much higher (e.g., as high as, or greater than 80° C.).

Advantageously, using a relatively high sulfur loading (e.g., greater than 10 wt %, or greater than 15 wt %) and sulfur dioxide recovery from the flash, when at least 30% to 100% of the $SO_2$ in the flash is recovered and/or recycled improves the economics of the process. In one embodiment, at least 50% of initial $SO_2$ charged into the system is flashed off following pretreatment. In one embodiment, about 40%-80% of initial $SO_2$ charged into the system is flashed off following pretreatment. In one embodiment, more than about 65% of initial $SO_2$ charged into the system is flashed off following pretreatment.

Enzymatic Hydrolysis

After the optional cooling and pH adjustment, enzyme(s) may be added to the pretreated biomass composition using known techniques (e.g., upstream and/or in the hydrolysis reactor). In one non-limiting example, enzyme addition is conducted by adding the enzyme(s) to a reservoir, such as a tank, to form an enzyme solution, which is then introduced to the pretreated biomass composition. In a further non-limiting example, the enzyme(s) is introduced to the pretreated feedstock composition via chemical injection quills, which are commercially available. Alternatively, enzyme may be injected into the pretreated feedstock composition through appropriately sized tubing or via a pipe. In general, addition of enzyme results in an enzymatic hydrolysis 30 wherein the cellulose in the pretreated biomass composition is converted to glucose.

In one embodiment, enzyme addition includes the addition of cellulase, which is an enzyme(s) that breaks cellulose chains into glucose. In particular, the term "cellulase" refers to any of several enzymes produced by fungi, bacteria, or protozoans that catalyze cellulolysis. For example, the term cellulase may denote a multi-enzyme mixture comprising exo-cellobiohydrolases (CBH), endoglucanases (EG) and β-glucosidases (βG) that can be produced by a number of plants and microorganisms. Among the most widely studied, characterized and commercially produced cellulases are those obtained from fungi of the genera *Aspergillus, Humicola, Chrysosporium, Melanocarpus, Myceliopthora, Sporotrichum* and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least four EG enzymes. As well, EGI, EGII, EGIII, EGV and EGVI cellulases have been isolated from *Humicola insolens*. In addition to CBH, EG and βG, there are several accessory enzymes that may aid in the enzymatic digestion of cellulose (see WO 2009/026722 (Scott), which is incorporated herein by reference and Harris et al., 2010, Biochemistry, 49:3305-3316). These include glycoside hydrolase 61 (GH61), swollenin, expansin, lucinen and cellulose-induced protein (Cip). For example, enzymes containing glycoside hydrolase 61 may improve hydrolysis.

In general, the enzyme dose may depend on the activity of the enzyme at the selected pH and temperature, the reaction time, the volume of the reactor, and/or other parameters. It should be appreciated that these parameters may be adjusted as desired by one of skill in the art to achieve optimal conditions. In one embodiment, the cellulase is added at a dosage between about 2 to 20 mg protein per gram cellulase. In one embodiment, the cellulase is added at a dosage between about 2 to 15 mg protein per gram cellulase. In one embodiment, the cellulase is added at a dosage between about 2 to 12 mg protein per gram cellulase. The protein may be quantified using either the bicinchoninic acid (BCA) assay or the Bradford assay.

In one embodiment, the hydrolysis is conducted at or near the temperature and/or pH optimum of the enzyme(s). For example, conventional cellulase may have optimum pH values between about 4.5 and about 5.5 and a temperature optimum between about 40° C. and about 60° C. In one embodiment, the enzymatic hydrolysis is conducted at a temperature above about 56° C., or 57° C. Conducting the hydrolysis at temperatures above about 56° C., and in particular, at temperatures above 57° C. or 58° C. may be advantageous in that microbial contamination may be reduced. Reduced microbial contamination may be particularly advantageous in $SO_2$ catalyzed systems, wherein the production of inhibitors to microbial contamination may be lower.

In one embodiment, the enzymatic hydrolysis and fermentation are conducted in separate vessels so that each biological reaction can occur at its respective optimal temperature. For example, in one embodiment, the hydrolysis is conducted in one or more dedicated hydrolysis reactors, which may be connected in series or in parallel. In general, the hydrolysis may be conducted in continuous, fed-batch, or batch mode. In one embodiment, the hydrolysis is conducted in continuous mode, which may offer greater productivity and lower costs. For example, in one embodiment, the hydrolysis is conducted one or more continuous stirred tank reactors (CSTRs) and/or one or more plug flow reactors (PFRs). In the plug flow reactor, the slurry is pumped through a pipe or tube such that it exhibits a relatively uniform velocity profile across the diameter of the pipe/tube and such that residence time within the reactor provides the desired conversion. In one embodiment, the hydrolysis includes a plurality of hydrolysis rectors including a PFR and a CSTR in series, as for example, described in U.S. Pat. No. 8,709,770, which is hereby incorporated by reference. In general, the number of hydrolysis reactors in the system may depend on the cost of the reactors, the volume of the pretreated biomass composition, and/or other factors. For a commercial-scale ethanol plant, the typical number of hydrolysis reactors may be, for example, 4 to 12. In order to maintain the desired hydrolysis temperature, the hydrolysis reactors may be jacketed with steam, hot water, or other heat sources. The total residence time in the enzymatic hydrolysis reactors is typically between about 24 hours and about 250 hours, depending on the degree of conversion desired, although could be shorter or longer.

Fermentation

In fermentation 40, the sugars produced during pretreatment (e.g., xylose and glucose) and/or enzymatic hydrolysis (e.g., glucose) are converted to alcohols, and in particular, to ethanol. For example, in one embodiment, the fermentation uses one or more microorganisms to convert the sugars to ethanol.

In general, the fermentation microorganism(s) may include any yeast and/or bacteria. For example, in one embodiment, the fermentation is carried out with *Saccharomyces* spp. yeast, which are attractive because of their capacity to produce ethanol.

In one embodiment, glucose and/or other hexoses derived from the cellulose are fermented to ethanol using a wild-type *Saccharomyces cerevisiae* or a genetically modified yeast. In one embodiment, xylose and or arabinose derived from the hemicelluloses are fermented to ethanol using a yeast strain that naturally contains, or has been engineered to contain, the ability to ferment these sugars to ethanol. Examples of microbes that have been genetically modified to ferment xylose include recombinant *Saccharomyces* strains into which has been inserted either (a) the xylose reductase (XR) and xylitol dehydrogenase (XDH) genes from *Pichia stipitis* (see for example U.S. Pat. Nos. 5,789,210, 5,866,382, 6,582,944 and 7,527,927 and European Patent No. 0450430) or (b) fungal or bacterial xylose isomerase (XI) gene (see for example U.S. Pat. Nos. 6,475,768 and 7,622,284). Examples of yeasts that have been genetically modified to ferment L-arabinose include, but are not limited to, recombinant *Saccharomyces* strains into which genes from either fungal (for example U.S. Pat. No. 7,527,951) or bacterial (for example WO 2008/041840) arabinose metabolic pathways have been inserted. Alternatively, xylose and other pentose sugars may be fermented to xylitol by yeast strains selected from the group consisting of *Candida, Pichia, Pachysolen, Hansenula, Debaryomyces, Kluyveromyces* and *Saccharomyces*.

In one embodiment, glucose derived from the cellulose during enzymatic hydrolysis is fermented to butanol by a microorganism such as *Clostridium acetobutylicum*.

The dose of the microorganism(s) will depend on other factors, such as the activity of the microorganism, the desired reaction time, the volume of the reactor and other parameters. It should be appreciated that these parameters may be adjusted as desired by one of skill in the art to achieve optimal conditions.

In one embodiment, the fermentation may be performed at or near the temperature and/or pH optimum of the corresponding microorganism. For example, *Saccharomyces cerevisiae* may have optimum pH values between about 4 and about 5.5 and a temperature optimum between about 25° C. and about 35° C.

In one embodiment, the enzymatic hydrolysis and fermentation are conducted in separate vessels so that each biological reaction can occur at its respective optimal temperature. In another embodiment, the hydrolysis (e.g., which may be also referred to as saccharification) is conducted simultaneously with the fermentation in same vessel. For example, in one embodiment, a simultaneous saccharification and fermentation (SSF) is conducted at temperature between about 35° C. and 38° C., which is a compromise between the 50° C. to 55° C. optimum for cellulase and the 25° C. to 35° C. optimum for yeast.

Regardless of whether the biological conversion includes a separate hydrolysis and fermentation (SHF), simultaneous saccharification and fermentation (SSF), or hybrid hydrolysis and fermentation (HHF) (e.g., wherein the two separate steps are conducted in a same reactor, but at different temperatures), the reactor(s) may contain the C5 sugars and/or the C6 sugars. More specifically, the reactors may contain not only the glucose released during cellulose hydrolysis, but also one or more sugars arising from the pretreatment (e.g., xylose, glucose, arabinose, mannose, and/or galactose), for a co-fermentation. Alternatively, in a SHF, the C5 sugars and/or C6 sugars produced during pretreatment are fed to a separate fermentation reactor and/or series of reactors than the C6 sugars produced during enzymatic hydrolysis.

In one embodiment, the fermentation is conducted on a sugar solution containing both C5 and C6 sugars using only *Saccharomyces cerevisiae*. In another embodiment, the fermentation is conducted on a sugar solution containing both C5 and C6 sugars using a mixture wherein C5 utilizing and ethanol producing yeasts (e.g., such as *Pichia fermentans* and *Pichia stipitis*) are cocultured with *Saccharomyces cerevisiae*.

In one embodiment, the fermentation is supplemented with additional nutrients required for the growth of the fermentation microorganism. For example, yeast extract, specific amino acids, phosphate, nitrogen sources, salts, trace elements and vitamins may be added to the hydrolyzate slurry to support their growth. In one embodiment, yeast recycle is employed.

In general, the fermentation may be conducted in continuous, fed-batch, or batch mode. In one embodiment, the fermentation is conducted in continuous mode, which may offer greater productivity and lower costs. In one embodiment, the fermentation is conducted in a plurality of fermentation tanks. For example, in one embodiment, the fermentation is conducted one or more continuous stirred tank reactors (CSTRs) and/or one or more plug flow reactors (PFRs). Advantageously, continuous mode operation may offer less reactor down time and smaller reactor volumes.

Alcohol Recovery

In general, the alcohol produced during fermentation is recovered 50, a process wherein alcohol may be concentrated and/or purified from the fermented solution (e.g., which may or may not have been subjected to a solids-liquid separation to remove unconverted cellulose, insoluble lignin, and/or other undissolved substances).

In one embodiment, alcohol recovery (e.g., ethanol recovery) uses one or more distillation columns that separate the alcohol from other components (e.g., water). In general, the distillation column(s) in the distillation unit may be operated in continuous or batch mode, although are typically operated in a continuous mode. Heat for the distillation process may be introduced at one or more points, either by direct steam injection or indirectly via heat exchangers. When the alcohol is ethanol, after distillation, the water remaining in the concentrated ethanol stream (i.e., vapour) may be removed from the ethanol rich vapour by a molecular sieve resin, by membrane extraction, or other methods known to those of skill in the art for concentration of ethanol beyond the 95% that is typically achieved by distillation (e.g., a vapour phase drying). The vapour may then be condensed and denatured.

Sulfur Dioxide Recovery

In general, sulfur dioxide obtained from the flash stream may be sent to sulfur dioxide recovery 60. More specifically, the flash stream, which contains excess sulfur dioxide and/or sulfur dioxide generated from solution as a result of the increased temperature and/or pressure reduction, is fed to a sulfur dioxide recovery unit.

In general, gas containing sulfur dioxide having a concentration in the range of about 1% to about 100% may be purified and/or condensed and/or may be used to provide liquid sulfur dioxide. For example, some processes of purifying and/or condensing sulfur dioxide gas and/or preparing liquid sulfur dioxide, which can be used to provide gas phase sulfur dioxide, include compressing and condensing (e.g., at high sulfur dioxide concentrations), partial condensation (e.g., at low sulfur dioxide concentrations), and absorption and acidification (e.g., scrubbing low concentrations of sulfur dioxide with ammonium bisulfite). For example, at atmospheric pressure pure sulfur dioxide will condense at −10.1° C., and at increased pressures will begin to condense at higher temperatures (i.e., will condense at 32.2° C. at 388 kPa (56.3 psig)).

In one embodiment, the sulfur dioxide recovery 60 includes a partial condenser that provides a first stream comprising a condensate (e.g., from the steam) and a second stream comprising gaseous sulfur dioxide. In one embodiment, the first stream comprising the condensate may be fed to a sulfur dioxide stripper, which removes any residual sulfur dioxide from the condensate to provide another stream of gaseous sulfur dioxide (e.g., the two streams of gaseous sulfur dioxide are optionally combined to provide a combined gas stream). The sulfur dioxide gas stream, or combined sulfur dioxide stream, may be dried (e.g., by countercurrent washing with 98% sulfuric acid), compressed, and/or condensed. In one embodiment, the sulfur dioxide, which is optionally stored temporarily, is recycled directly back into the process. In one embodiment, the recycling includes generating gaseous sulfur dioxide from liquid sulfur dioxide for impregnating the lignocellulosic biomass, or forming a sulfurous acid solution that is used to impregnate the lignocellulosic biomass. In one embodiment, gaseous sulfur dioxide is compressed and stored for recycling back into the process.

In one embodiment, the sulfur dioxide recovery 60 includes a sulfur dioxide scrubbing system. For example, in one embodiment, the sulfur dioxide scrubbing system comprises one or more packed absorbers (e.g., in series). In one embodiment, the absorbers include amine-based, alkali-based, or other absorbers.

In one embodiment, the sulfur dioxide recovery 60 includes a regenerative sulfur dioxide scrubbing system. In one embodiment, the sulfur dioxide-rich absorbers are fed to a regeneration or stripping column in which the sulfur dioxide is removed (e.g., by steam) and the absorber regenerated. In one embodiment, the regenerative sulfur dioxide scrubbing system is wet sulfur dioxide scrubbing system. In one embodiment, the regenerative sulfur dioxide scrubbing system is a dual alkali system using a first alkali absorber to scrub the gas stream, and a second alkali to regenerate the absorber.

In one embodiment, the regenerative sulfur dioxide scrubbing system is disposed downstream of a partial condenser that provides a first stream comprising a condensate (e.g., from the steam) and a second stream comprising gaseous sulfur dioxide. For example, in one embodiment, the second stream comprising gaseous sulfur dioxide is fed to a regenerative wet sulfur dioxide scrubbing system to provide the recovered sulfur dioxide. In one embodiment, the recovered sulfur dioxide is further processed to provide commercial grade liquid sulfur dioxide. In one embodiment, the recovered or further processed sulfur dioxide gas stream is dried (e.g., by countercurrent washing with 98% sulfuric acid), compressed, and condensed as liquid sulfur dioxide. Alternatively, the recovered sulfur dioxide is converted into elemental sulfur, which may be used to provide the recycled sulfur dioxide.

In one embodiment, the sulfur recovery 60 comprises a sulfur burner, which burns sulfur in the presence of a high concentration of oxygen, to provide the sulfur dioxide. In one embodiment, the sulfur recovery 60 comprises a sulfur burner that uses the flash stream, or a stream derived from the flash stream, to reduce the temperature in the sulfur burner.

Advantageously, the sulfur dioxide recovery 60 allows the recycling of sulfur within the system, and thus improves the process economics (e.g., since less sulfur dioxide and/or sulfurous acid needs to be purchased for pretreatment). In addition, the sulfur dioxide recovery improves the economics of using a high sulfur dioxide loading, particularly, when the sulfur dioxide recovery 60 is efficient at high sulfur dioxide concentrations. Accordingly, the process may exploit the advantages of combining high sulfur dioxide loadings with temperatures above about 180° C. (e.g., fewer and/or lower concentrations of potential inhibitors combined with a more efficient pretreatment), without significant increases in cost.

In fact, providing relatively high sulfur dioxide loadings (e.g., either from gaseous sulfur dioxide and/or sulfurous acid) without a volatile solvent (e.g., ethanol) advantageously facilitates a simple flash steam recovery of sulfur dioxide. In addition, it simplifies any further purification and/or processing of the sulfur dioxide recovered from the flash stream. Since the recovery may be relatively simple and efficient, the cost of the relatively high sulfur loading is not as limiting. Accordingly, the advantages of using a high sulfur loading for pretreatment may be exploited.

In addition to the cost of high sulfur dioxide loading, sulfur dioxide may not have been used at high loadings in $SO_2$ catalyzed pretreatment because, with the pKa of sulfur dioxide being about 1.81, at pH values above 1.8, which corresponds to low loadings, the bisulfite species ($HSO_3^-$) is more predominant. Bisulfite and or bisulfite salts have been used in sulfite pulping and/or Sulfite Pretreatment to Overcome Recalcitrance of Lignocellulose (SPORL) processes, the latter of which includes a sulfite treatment followed by a mechanical size reduction. The conditions for sulfite pulping and/or SPORL are generally different from $SO_2$-catalyzed pretreatment. For example, sulfite pulping is typically carried out between pH 1.5 and 5, whereas SPORL is typically conducted at relatively low temperatures (e.g., lower than $SO_2$ catalyzed pretreatment). In addition, both sulfite pulping and SPORL are typically conducted in digesters wherein the lignocellulosic biomass (e.g., woody biomass) is submerged and/or mixed with excess liquid (e.g., sulfite salt containing) referred to as the liquor for relatively long time periods (e.g., over an hour). In contrast, it is advantageous to conduct $SO_2$ catalyzed pretreatments under conditions wherein there is not a lot of free liquid, thus allowing a more uniform and/or rapid penetration of the sulfur dioxide and/or steam during the relatively short pretreatment time (e.g., under 30 minutes).

Advantageously, the combination of relatively high sulfur dioxide dosage and a pretreatment temperature above about 180° C. has been found to produce fewer and/or less inhibitors/inactivators, and/or a concentration of inhibitors/inactivators that does not significantly affect the ethanol yield from fermentation, even when the pretreated lignocellulosic biomass composition is not substantially washed, diluted, and/or otherwise treated to reduce fermentation inhibition/inactivation (e.g., other than the pH and/or temperature adjustment to where the enzyme(s) is reasonably active).

Further advantageously, by accounting for the slurry volume of the pretreatment reactor and/or the consistency of the slurry at the beginning of pretreatment, a more efficient sulfur dioxide dosage may be selected (e.g., such that the effective sulfur dioxide dosage is above 0.8 wt % and the effective sulfur dioxide concentration in the slurry is between 0.25 wt % and 1.5 wt %). Alternatively, by accounting for the slurry volume of the pretreatment reactor, and a desired sulfur dioxide dosage, the moisture level of the lignocellulosic biomass may be selected such that the effective sulfur dioxide concentration in the slurry is between 0.25 wt % percent and 1.5 wt %. Further alternatively, by accounting for the consistency of the slurry at the beginning of pretreatment and a desired sulfur dioxide dosage, the slurry volume of the pretreatment reactor may be selected accordingly (e.g., to improve the effectiveness of pretreatment).

Figure 3:
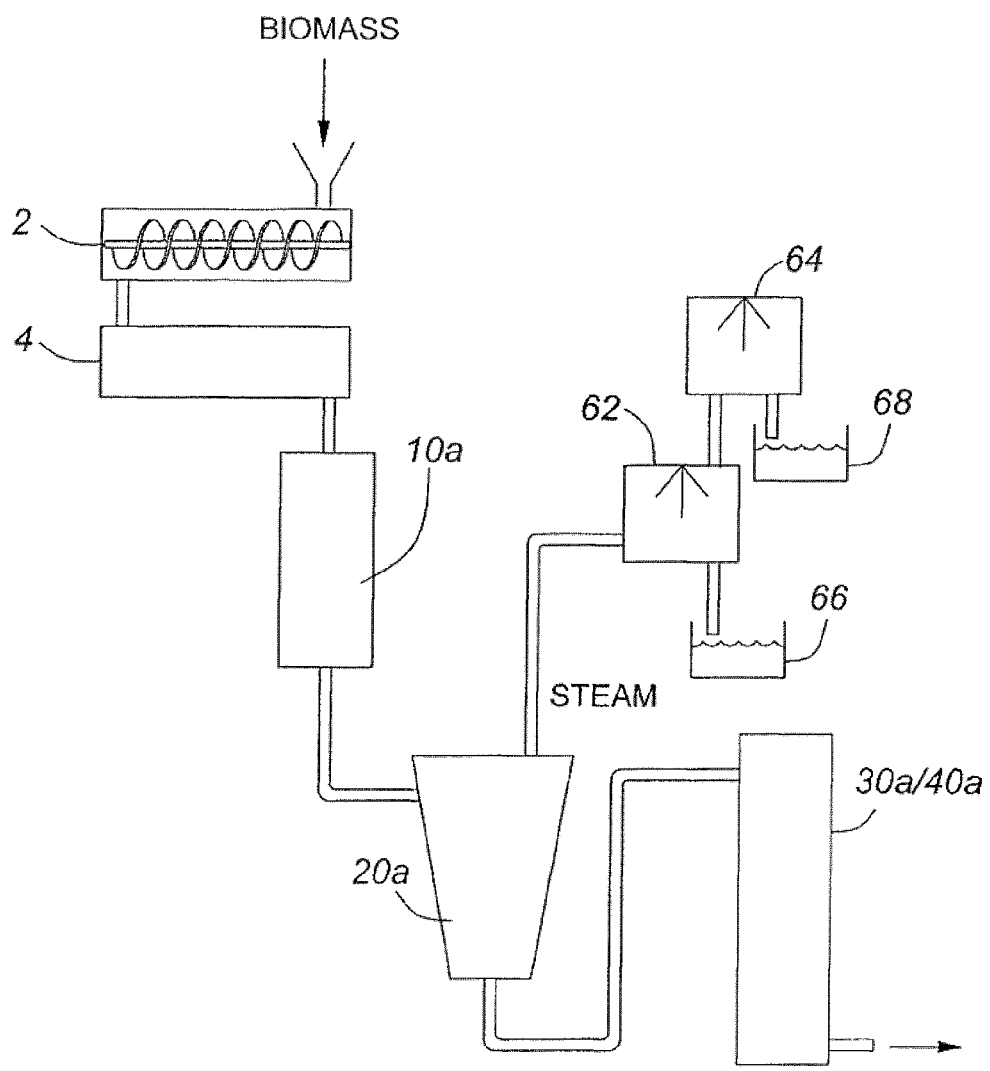
FIG. 3 is a schematic diagram showing a system for producing alcohol in accordance with one embodiment of the invention.

Referring to FIG. 3, there is shown a system in accordance one embodiment of the invention, which may be used to perform the method discussed with reference to FIG. 1. In operation, lignocellulosic biomass is optionally slurried and provided to an optional pressurized dewatering system 2, an optional heating chamber 4, and a pretreatment reactor 10a. Although illustrated as three separate components for demonstrative purposes, it should be understood that the pretreatment reactor 10a may be part of a pretreatment system that includes these and/or other components, which may be provided as one or more separate components and/or as integrated components. For example, in one embodiment, the pretreatment is provided according to one of the pretreatment systems described in US Publication Nos. 2010/0056774 and/or 2013/0071903, which are hereby incorporated by reference and particularly for the purpose of describing such pretreatment systems.

Optionally, the slurry is soaked prior to being dewatered. The optionally soaked slurry, which may have a consistency of about 1 wt % to about 12 wt %, and more commonly between about 2 wt % to about 10 wt %, is fed to the pressurized dewatering system 2. The pressurized dewatering system 2 may include a predraining zone (not shown), wherein at least some of the water is removed and fed to a high pressure pump (not shown), which creates a high pressure zone for further dewatering. The pressurized dewatering system 2 reduces the moisture content of the biomass to an amount selected for pretreatment. For example, in one embodiment, the pressurized dewatering system 2 includes a pressurized dewatering press or a pressurized plug screw feeder (e.g., as described in US Publication No. 2010/0056774). In one embodiment, the pressured dewatering system 2 is at a pressure between about 70 psia and about 800 psia. The dewatered biomass (e.g., which may or may not be in plug form and may have a consistency between about 15 wt % and about 40 wt %), may then be fed to the optional heating chamber 4, as for example, described in US Publication No. 2013/0071903, and then to the pretreatment reactor 10a.

Sulfur dioxide and/or sulfurous acid may be added in the pressurized dewatering system 2, in the heating chamber 4, and/or directly into the pretreatment reactor 10a. For example, in one embodiment, gaseous sulfur dioxide is added to the biomass upstream of the inlet of a pressurized screw press, at the inlet to a pressurized screw press, in a dewatering zone of a pressurized screw press, in the pressurized plug screw feeder, in the heating chamber, and/or in the reaction zone of the pretreatment reactor.

The pretreatment reactor 10a, which for exemplary purposes is shown as a vertical reactor, may be any reactor that may contain the biomass while the biomass is subject to at least a portion of the pretreatment. For example, in one embodiment the pretreatment reactor is a vertical reactor, such as an upflow or downflow vertical reactor. In another embodiment, the pretreatment reactor is a horizontal or inclined reactor. The pretreatment reactor 10a may be equipped with an internal mechanism, such as a screw, conveyor, or similar mechanism, for conveying the lignocellulosic biomass within a reactor zone of the pretreatment reactor. Optionally, the pretreatment reactor 10a includes a sulfur dioxide reservoir or charge, as for example, described in U.S. Prov. US. Ser. No. 62/293,481, filed on Feb. 10, 2016, which is hereby incorporated by reference.

In one embodiment, the pretreatment reactor 10a includes one or more inlets for injecting steam into the biomass. Accordingly, the pretreatment reactor 10a may be held at a predetermined temperature and/or pressure. For example, in one embodiment the one or more inlets for injecting steam are provided near the reactor zone of the pretreatment reactor 10a.

In general, the biomass will be treated in the pressurized pretreatment reactor 10a at an elevated temperature (e.g., above 170° C.) for a specific amount of time. In general, the temperature, pressure, and/or residence time of the biomass in the reaction zone may depend upon a number of variables, including the pH in the reaction zone and the desired degree of pretreatment. In one embodiment, the biomass has a residence time in the pretreatment reactor 10a from about 10 seconds to about 20 minutes, or about 10 seconds to about 10 minutes. The final pH for the pretreatment may be between about 0.5 and about 1.5, or between about 1.0 and about 1.5. Notably, the partially dewatered lignocellulosic feedstock may be heated prior to its entry into the reaction zone (e.g., in the optional heating chamber 4), in the reaction zone, or a combination thereof.

When the biomass has been resident in the reactor zone of the pretreatment reactor 10a for the pretreatment time, the pretreated biomass is then discharged into a flash tank 20a to provide the pretreated biomass. Since the flash tank 20a is held at a pressure that is lower than the pressure of the pretreatment reactor 10a during pretreatment, the temperature of the pretreated biomass will drop from the pretreatment temperature to a temperature dependent on the pressure in the flash tank. For example, if the flash tank is at about atmospheric pressure, the pretreated biomass temperature will be about 100° C. If the flash tank is below atmospheric pressure, the temperature will be lower than 100° C. If the flash tank is held above atmospheric pressure, the temperature will be greater than 100° C.

The cooled, pretreated biomass composition produced by the pretreatment reactor 10a and flash tank 20a is fed to a hydrolysis tank 30a or a combined hydrolysis/fermentation tank 30a/40a, followed by alcohol recovery (not shown). Depending on the temperature and/or pH of the cooled, pretreated biomass composition, it may be subjected to a temperature and/or pH adjustment (not shown). For example, in one embodiment, the cooled, pretreated biomass composition is actively cooled.

The flash stream exiting from the top of the flash tank 20a may include steam, gaseous sulfur dioxide, and/or other volatile compounds (e.g., which may depend on the pressure of the flash tank). In general, the flash stream may be fed to any sulfur dioxide recovery (e.g., as described in International Patent Application PCT/CA2016/050292, filed Mar. 16, 2016, which is hereby incorporated by reference and particularly for the purpose of describing such sulfur dioxide recovery systems). In the embodiment illustrated in FIG. 3, the flash stream is fed to a two-stage system. More specifically, the flash stream is fed to a partial condenser 62, wherein most of the steam is condensed and collected in reservoir 66. For example, the partial condenser may include a tower that is suitably packed and provided with a water spray or shower. The sulfur dioxide gas passes through the partial condenser and exits from the top, where it is fed to a sulfur dioxide absorption tower 64. The second stage sulfur dioxide absorption tower 64, which is likewise packed with a suitable packing material and equipped with a water spray or shower, provides a cool spray of water that absorbs the sulfur dioxide to form a sulfurous acid solution that is collected in reservoir 68. Notably, while the temperature of the water spray in tower 64 is selected to absorb sulfur dioxide, the temperature of the water in tower 62 is selected to keep the sulfur dioxide in gaseous form (e.g., is higher). Nevertheless, the aqueous solution in reservoir 66 may contain some sulfur dioxide and thus may be fed to a sulfur dioxide stripper for further processing. The sulfurous acid solution from the reservoir 68 may be further purified and/or concentrated and recycled back into the process (i.e., to provide the catalyst for pretreatment).

Figure 4:
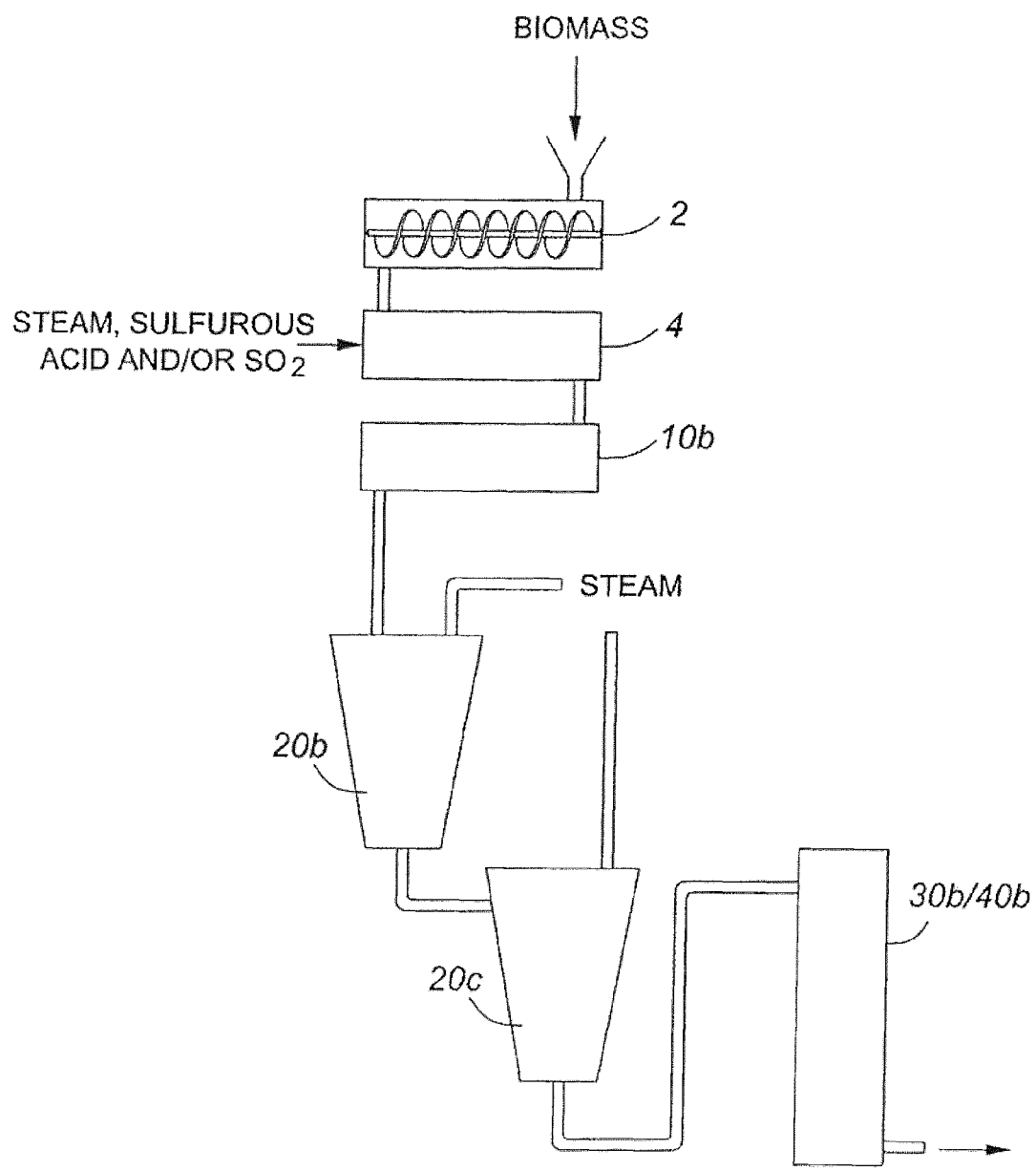
FIG. 4 is a schematic diagram showing a system for producing alcohol in accordance with one embodiment of the invention.

Referring to FIG. 4, there is shown another embodiment of a system in accordance with one embodiment of the invention. In operation, lignocellulosic biomass is slurried and provided to a pressurized dewatering system 2, a heating chamber 4, and pretreatment reactor 10b. Although illustrated as three separate components for demonstrative purposes, it should be understood that the pretreatment reactor 10b may be part of a pretreatment system that includes these and/or other components, which may be provided as one or more separate components and/or as integrated components. For example, in one embodiment, the pretreatment is provided according to one of the pretreatment systems described in US Publication Nos. 2010/0056774 and/or 2013/0071903, which are hereby incorporated by reference and particularly for the purpose of describing such pretreatment systems.

Optionally, the slurry is soaked prior to being dewatered. The optionally soaked slurry, which may have a consistency of about 1 wt % to about 12 wt %, and more commonly between about 2 wt % to about 10 wt %, is fed to the pressurized dewatering system 2. The pressurized dewatering system 2 may include a predraining zone (not shown), wherein at least some of the water is removed and fed to a high pressure pump (not shown), which creates a high pressure zone for further dewatering. The pressurized dewatering system 2 reduces the moisture content of the biomass to an amount suitable for pretreatment. For example, in one embodiment, the pressurized dewatering system 2 includes a pressurized dewatering press or a pressurized plug screw feeder (e.g., as described in US Publication No. 2010/0056774). In one embodiment, the pressured dewatering system 2 is at a pressure between about 70 psia and about 800 psia. The dewatered biomass (e.g., which may or may not be in plug form and may have a consistency between about 20 wt % and about 67 wt %), may then be fed to the heating chamber 4, as for example, described in US Publication No. 2013/0071903, and then to the pretreatment reactor 10b.

Steam, sulfur dioxide and/or sulfurous acid are added in the heating chamber 4, which is disposed upstream of the pretreatment reactor 10b. Optionally, steam, sulfur dioxide, and/or sulfurous acid, are also added directly to the pretreatment reactor 10b. In one embodiment, the heating chamber 4 includes a rotating shaft having one or more disintegrating elements disposed thereon for breaking up and/or fluffing up dewatered biomass (e.g., breaking up plugs and/or plug segments of the lignocellulosic biomass) produced by the pressurized dewatering system 2. In one embodiment, the disintegrating elements rotate at a speed selected to fluff up the dewatered biomass thus distributing the fibres and water content over a larger area. Accordingly, the disintegrating elements may provide a more uniform sulfur dioxide and/or steam impregnation.

The pretreatment reactor 10b, which for exemplary purposes is shown as a horizontal reactor, may be any reactor that may contain the biomass while the biomass is subject to at least a portion of the pretreatment. The pretreatment reactor 10b may be equipped with an internal mechanism, such as a screw, conveyor, or similar mechanism, for conveying the lignocellulosic feedstock within a reactor zone of the pretreatment reactor. In one embodiment, the pretreatment reactor 10b includes one or more inlets for injecting steam into the biomass. Optionally, the one or more steam injection inlets are used to hold the pretreatment reactor at a predetermined temperature and/or pressure. In one embodiment, the one or more inlets for injecting steam are provided near the reactor zone of the pretreatment reactor 10b.

In general, the biomass will be treated in the pressurized pretreatment reactor 10b at an elevated temperature (e.g., above 170° C.) for a specific amount of time. In general, the temperature, pressure, and/or residence time of the biomass in the reaction zone may depend upon a number of variables, including the pH in the reaction zone and the degree of pretreatment. In one embodiment, the biomass has a residence time in the pretreatment reactor from about 10 seconds to about 30 minutes, or about 10 seconds to about 600 seconds. The final pH for the pretreatment may be between about 0.5 and about 1.5, or between about 1.0 and about 1.5. Notably, the partially dewatered lignocellulosic feedstock may be heated prior to its entry into the reaction zone (e.g., heated in the heating chamber 4), in the reaction zone, or a combination thereof.

When the biomass has been resident in the reactor zone of the pretreatment reactor 10b for the pretreatment time, the pretreated biomass is then discharged into a flash tank 20b to provide the pretreated biomass. The pretreated biomass is then fed to a second flash tank 20c. Since the flash tank 20b is held at a pressure that is lower than the pressure of the pretreatment reactor 10b, the temperature of the pretreated biomass will drop from the pretreatment temperature to a temperature dependent on the pressure in the flash tank 20b. In this embodiment, the first flash tank 20b and a second flash tank 20c are part of a flashing system. In general, the pressure of the first flash tank 20b will be higher than the pressure of the second flash tank 20c. Since the first flash tank 20b is held at a pressure that is lower than the pressure of the pretreatment reactor 10b, but higher than the pressure of the second flash tank 20c, the temperature of the pretreated biomass composition will drop as it passes from the pretreatment reactor 10b, to the first flash tank 20b, and to the second flash tank 20c.

The cooled, pretreated biomass composition produced by the pretreatment and flashing is fed to at least one hydrolysis tank 30b followed by at least one fermentation tank 40b, and/or at least one combined hydrolysis/fermentation tank 30b/40b. A stream containing the fermentation product (i.e., alcohol), is fed to alcohol recovery (not shown). Depending on the temperature and/or pH of the cooled, pretreated biomass composition, it may be subjected to a temperature and/or pH adjustment (not shown) prior to enzymatic hydrolysis and/or fermentation. For example, in one embodiment, the cooled, pretreated biomass composition is actively cooled.

The flash stream vented from each of the flash tanks 20b/20c is optionally fed to a sulfur dioxide recovery (not shown). For example, in one embodiment, the flash stream vented from each of the flash tanks 20b/20c is optionally fed to a sulfur dioxide recovery system, as for example, disclosed in International Patent Application PCT/CA2016/

050292, which is hereby incorporated by reference and particularly for the purpose of describing such sulfur dioxide recovery systems.

Figure 5:
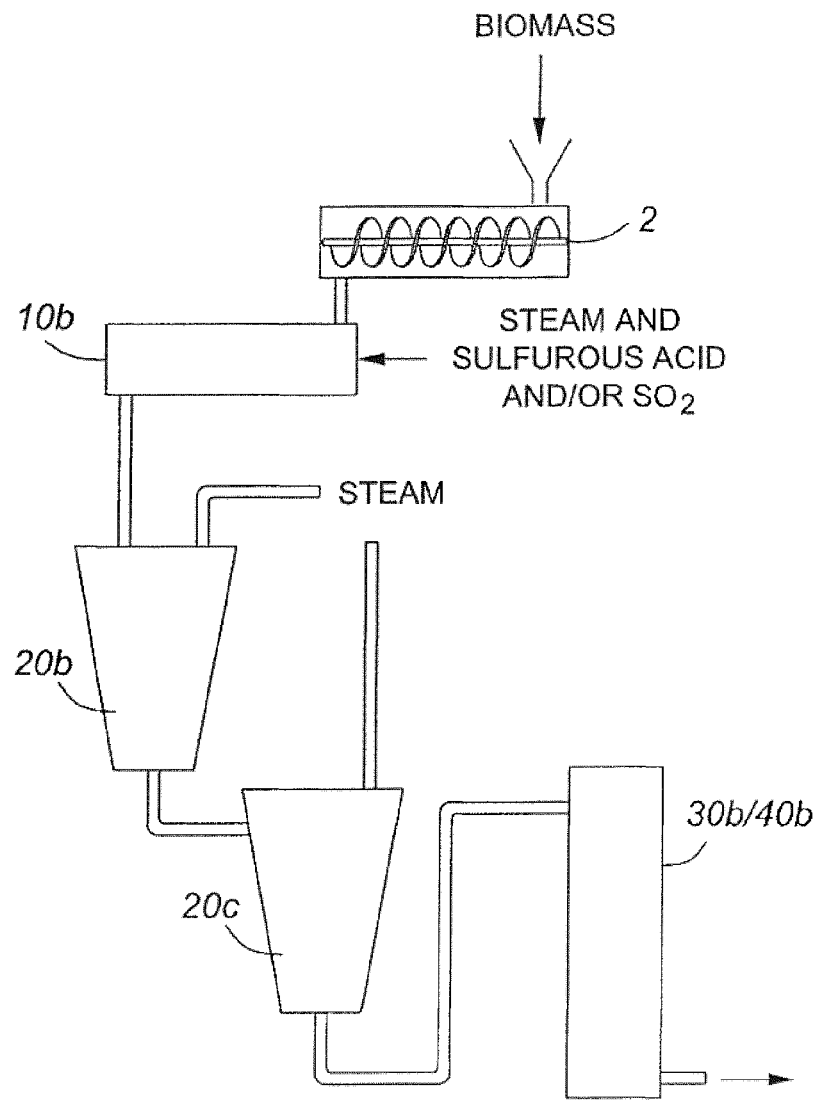
FIG. 5 is a schematic diagram showing a system for producing alcohol in accordance with one embodiment of the invention.

Referring to FIG. 5, there is shown another embodiment of a system in accordance with one embodiment of the invention. In operation, lignocellulosic biomass is slurried and provided to a pressurized dewatering system 2, followed by a pretreatment reactor 10b. Although illustrated as two separate components for demonstrative purposes, it should be understood that the pretreatment reactor 10b may be part of a pretreatment system that includes these and/or other components, which may be provided as one or more separate components and/or as integrated components. For example, in one embodiment, the pretreatment is provided according to one of the pretreatment systems described in US Publication Nos. 2010/0056774 and/or 2013/0071903, which are hereby incorporated by reference and particularly for the purpose of describing such pretreatment systems.

Optionally, the slurry is soaked prior to being dewatered. The optionally soaked slurry, which may have a consistency of about 1 wt % to about 12 wt %, and more commonly between about 2 wt % to about 10 wt %, is fed to the pressurized dewatering system 2. The pressurized dewatering system 2 may include a predraining zone (not shown), wherein at least some of the water is removed and fed to a high pressure pump (not shown), which creates a high pressure zone for further dewatering. The pressurized dewatering system 2 reduces the moisture content of the biomass to an amount suitable for pretreatment. For example, in one embodiment, the pressurized dewatering system 2 includes a pressurized dewatering press or a pressurized plug screw feeder (e.g., as described in US Publication No. 2010/0056774). In one embodiment, the pressured dewatering system 2 is at a pressure between about 70 psia and about 800 psia. The dewatered biomass (e.g., which may or may not be in plug form and may have a consistency between about 20 wt % and about 67 wt %), may then be fed to the pretreatment reactor 10b.

In this embodiment, steam, sulfur dioxide and/or sulfurous acid are added directly to the pretreatment reactor 10b. The pretreatment reactor 10b, which for exemplary purposes is shown as a horizontal reactor, may be any reactor that may contain the biomass while the biomass is subject to at least a portion of the pretreatment. The pretreatment reactor 10b may be equipped with an internal mechanism, such as a screw, conveyor, or similar mechanism, for conveying the lignocellulosic feedstock within a reactor zone of the pretreatment reactor. In one embodiment, the steam is introduced into the pretreatment reactor 10b via one or more inlets for injecting steam into the biomass. Optionally, the one or more steam injection inlets are used to hold the pretreatment reactor at a predetermined temperature and/or pressure. In one embodiment, the one or more inlets for injecting steam are provided upstream and/or near the reactor zone of the pretreatment reactor 10b.

In general, the biomass will be treated in the pressurized pretreatment reactor 10b at an elevated temperature (e.g., above 180° C.) for a specific amount of time. In general, the temperature, pressure, and/or residence time of the biomass in the reaction zone may depend upon a number of variables, including the pH in the reaction zone and the degree of pretreatment. In one embodiment, the biomass has a residence time in the pretreatment reactor from about 10 seconds to about 30 minutes, or about 10 seconds to about 600 seconds. The pH for the pretreatment may be between about 0.5 and about 1.5, or between about 1.0 and about 1.5.

When the biomass has been resident in the reactor zone of the pretreatment reactor 10b for the pretreatment time, the pretreated biomass is then discharged into a flash tank 20b to provide the pretreated biomass. The pretreated biomass is then fed to a second flash tank 20c. Since the flash tank 20b is held at a pressure that is lower than the pressure of the pretreatment reactor 10b, the temperature of the pretreated biomass will drop from the pretreatment temperature to a temperature dependent on the pressure in the flash tank 20b. In this embodiment, the first flash tank 20b and a second flash tank 20c are part of a flashing system. In general, the pressure of the first flash tank 20b will be higher than the pressure of the second flash tank 20c. Since the first flash tank 20b is held at a pressure that is lower than the pressure of the pretreatment reactor 10b, but higher than the pressure of the second flash tank 20c, the temperature of the pretreated biomass composition will drop as it passes from the pretreatment reactor 10b, to the first flash tank 20b, and to the second flash tank 20c.

The cooled, pretreated biomass composition produced by the pretreatment and flashing is fed to at least one hydrolysis tank 30b followed by at least one fermentation tank 40b, and/or at least one combined hydrolysis/fermentation tank 30b/40b. A stream containing the fermentation product (i.e., alcohol), is fed to alcohol recovery (not shown). Depending on the temperature and/or pH of the cooled, pretreated biomass composition, it may be subjected to a temperature and/or pH adjustment (not shown) prior to enzymatic hydrolysis and/or fermentation. For example, in one embodiment, the cooled, pretreated biomass composition is actively cooled.

The flash stream vented from each of the flash tanks 20b/20c is optionally fed to a sulfur dioxide recovery (not shown). For example, in one embodiment, the flash stream vented from each of the flash tanks 20b/20c is optionally fed to a sulfur dioxide recovery system, as for example, disclosed in International Patent Application PCT/CA2016/050292, which is hereby incorporated by reference and particularly for the purpose of describing such sulfur dioxide recovery systems.

Figure 6:
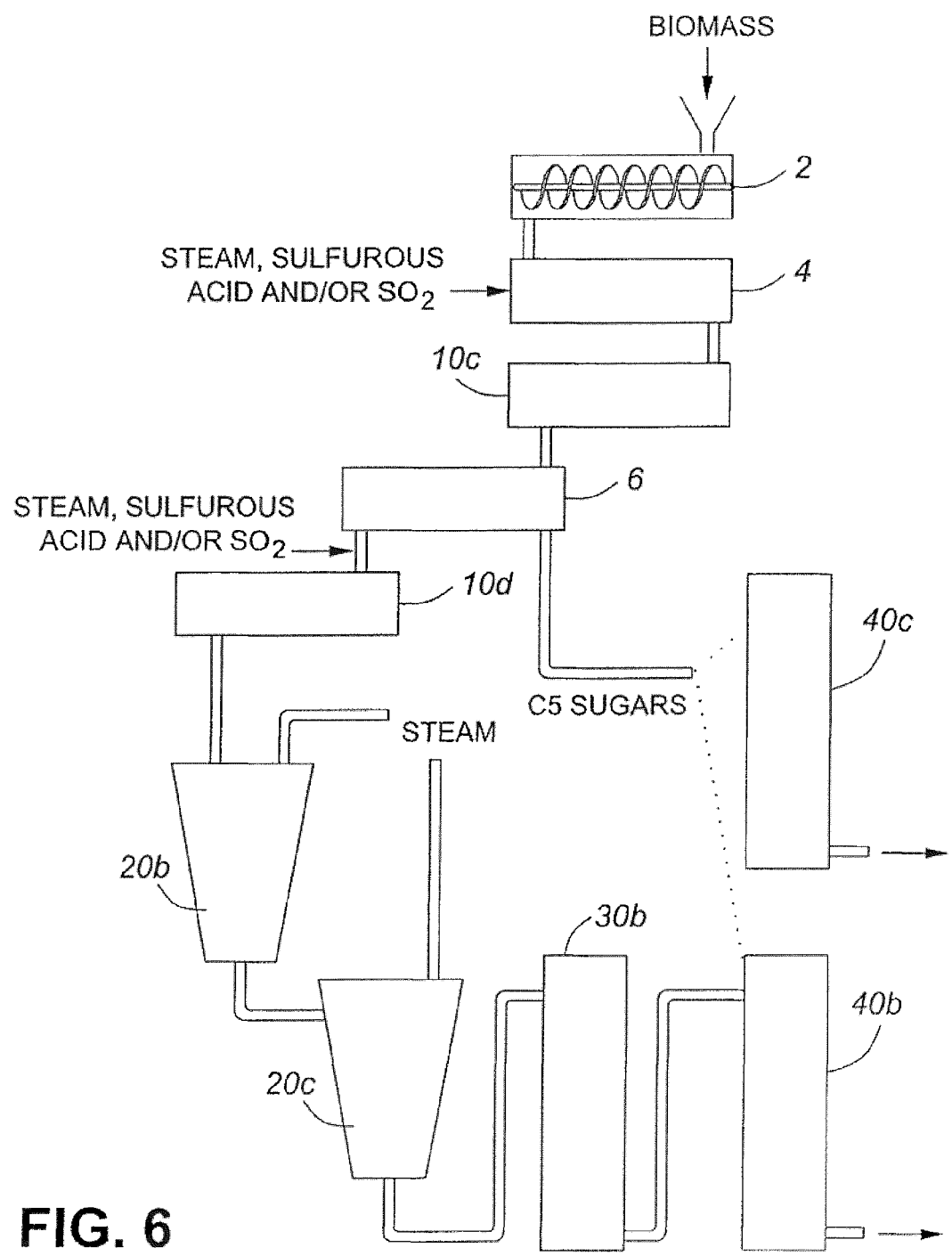
FIG. 6 is a schematic diagram showing a system for producing alcohol in accordance with one embodiment of the invention

Referring to FIG. 6, there is shown another embodiment of a system in accordance with one embodiment of the invention. In operation, lignocellulosic biomass is slurried and provided to a pressurized dewatering system 2, a heating chamber 4, a first pretreatment reactor 10c, a solid liquid separator 6, and a second pretreatment reactor 10d. Although illustrated as five separate components for demonstrative purposes, it should be understood that the pretreatment reactors 10c/10d may be part of a pretreatment system that includes these and/or other components, which may be provided as one or more separate components and/or as integrated components. In one embodiment, these components are held at the same pressure. In another embodiment, one or more components are held at different pressures. In one embodiment, at least one of the components includes and/or is based on a pretreatment system described in US Publication Nos. 2010/0056774 and/or 2013/0071903, which are hereby incorporated by reference and particularly for the purpose of describing such pretreatment systems.

Optionally, the slurry is soaked prior to being dewatered. The optionally soaked slurry, which may have a consistency of about 1 wt % to about 12 wt %, and more commonly between about 2 wt % to about 10 wt %, is fed to the pressurized dewatering system 2. The pressurized dewatering system may include a predraining zone (not shown), wherein at least some of the water is removed and fed to a high pressure pump (not shown), which creates a high pressure zone for further dewatering. The pressurized dewatering system 2 reduces the moisture content of the biomass to an amount suitable for pretreatment. For example, in one embodiment, the pressurized dewatering system 2 includes a pressurized dewatering press or a pressurized plug screw feeder (e.g., as described in US Publication No. 2010/0056774). In one embodiment, the pressured dewatering system 2 is at a pressure between about 70 psia and about 800 psia. The dewatered biomass (e.g., which may or may not be in plug form and may have a consistency between about 15 wt % and about 40 wt %), may then be fed to the heating chamber 4, as for example, described in US Publication No. 2013/0071903, and then to the pretreatment reactor 10c.

Steam, sulfur dioxide and/or sulfurous acid are added in the heating chamber 4, which is disposed upstream of the pretreatment reactor 10c. Optionally, steam, sulfur dioxide, and/or sulfurous acid, are also added directly to the pretreatment reactor 10c. In one embodiment, the heating chamber 4 includes a rotating shaft having one or more disintegrating elements disposed thereon for breaking up plugs and/or plug segments of the lignocellulosic biomass produced by the pressurized dewatering system 2 and/or for fluffing up compressed dewatered lignocellulosic biomass. For example, in one embodiment, the disintegrating elements rotate at a speed selected to fluff up the dewatered biomass, thus distributing the fibres and water content over a larger area. Accordingly, the disintegrating elements may provide a more uniform sulfur dioxide and/or steam impregnation.

The pretreatment reactor 10c, which for exemplary purposes is shown as a horizontal reactor, may be any reactor that may contain the biomass while the biomass is subject to at least a portion of the pretreatment. The pretreatment reactor 10c may be equipped with an internal mechanism, such as a screw, conveyor, or similar mechanism, for conveying the lignocellulosic feedstock within a reactor zone of the pretreatment reactor. Optionally, the pretreatment reactor 10c includes one or more inlets for injecting steam into the biomass, which may be used to hold the pretreatment reactor at a predetermined temperature and/or pressure. In one embodiment, the one or more inlets for injecting steam are provided near the reactor zone of the pretreatment reactor 10c.

In general, the biomass will be treated in the pressurized pretreatment reactor 10c at an elevated temperature (e.g., above 100° C.) for a specific amount of time. In general, the temperature, pressure, and/or residence time of the biomass in the reaction zone may depend upon a number of variables, including the pH in the reaction zone and the degree of pretreatment.

In this embodiment, the pretreatment is conducted in two stages, the first stage occurring in the first pretreatment reactor 10c, the second stage occurring in the second pretreatment reactor 10d. The conditions in the first pretreatment reactor 10c are selected to hydrolyze at least a portion of the hemicellulose and provide C5 sugars (e.g., such as xylose), whereas the conditions in the second pretreatments reactor 10d, are selected to increase digestability of the lignocellulosic biomass. Accordingly, the severity of the pretreatment in the first reactor 10c may be low relative to the severity of the pretreatment in the second reactor 10d. For example, in one embodiment, the pretreatment temperature in the first reactor 10c is below 180° C., whereas a pretreatment temperature in the second reactor 10d is greater than 180° C. In one embodiment, the biomass has a total residence time in the two pretreatment reactors of about 10 seconds to about 30 minutes, or about 10 seconds to about 600 seconds. The pH for the pretreatment may vary about 0.5 and about 1.5, or between about 1.0 and about 1.5, for at least one of the reactors. Notably, the partially dewatered lignocellulosic feedstock may be heated prior to its entry into the reaction zone (e.g., in the heating chamber 4), in the reaction zone, or a combination thereof.

When the biomass has been resident in the pretreatment reactor 10c for the pretreatment time, the pretreated biomass is then fed to the solid liquid separator 6. The solid liquid separator 6 removes at least a portion of the liquid, which includes C5 sugars produced during the first stage of pretreatment, while a stream containing the solid portion, including unreacted cellulose, is fed to the second pretreatment reactor 10d.

In this embodiment, the pretreatment conditions in the second pretreatment reactor 10d are selected to further improve accessibility and/or susceptibility of the cellulose to enzyme (e.g., for enzymatic hydrolysis). Accordingly, the severity of the pretreatment may be relatively high. For example, in one embodiment, the pretreatment temperature is above 180° C.

When the biomass has been resident in the reactor zone of the pretreatment reactor 10d for the pretreatment time, the pretreated biomass is then discharged into a flash tank 20b to provide the pretreated biomass. The pretreated biomass is then fed to a second flash tank 20c. Since the flash tank 20b is held at a pressure that is lower than the pressure of the pretreatment reactor 10b, the temperature of the pretreated biomass will drop from the pretreatment temperature to a temperature dependent on the pressure in the flash tank 20b. In this embodiment, the first flash tank 20b and a second flash tank 20c are part of a flashing system. In general, the pressure of the first flash tank 20b will be higher than the pressure of the second flash tank 20c. Since the first flash tank 20b is held at a pressure that is lower than the pressure of the pretreatment reactor 10b, but higher than the pressure of the second flash tank 20c, the temperature of the pretreated biomass composition will drop as it passes from the pretreatment reactor 10b, to the first flash tank 20b, and to the second flash tank 20c.

The cooled, pretreated biomass composition produced by the pretreatment and flashing is fed to at least one hydrolysis tank 30b followed by at least one fermentation tank 40b, and/or at least one combined hydrolysis/fermentation tank 30b/40b.

A stream containing the fermentation product (i.e., alcohol), is fed to alcohol recovery (not shown). Depending on the temperature and/or pH of the cooled, pretreated biomass composition, it may be subjected to a temperature and/or pH adjustment (not shown) prior to enzymatic hydrolysis and/or fermentation. For example, in one embodiment, the cooled, pretreated biomass composition is actively cooled.

The flash stream vented from each of the flash tanks 20b/20c is optionally fed to a sulfur dioxide recovery (not shown). For example, in one embodiment, the flash stream vented from each of the flash tanks 20b/20c is optionally fed to a sulfur dioxide recovery system, as for example, disclosed in International Patent Application PCT/CA2016/050292, which is hereby incorporated by reference and particularly for the purpose of describing such sulfur dioxide recovery systems.

As discussed above, providing a system that includes sulfur dioxide recovery may facilitate processes that have a relatively high sulfur dioxide loading (e.g., greater than about 6 wt %). Advantageously, pretreatment at temperatures over 185° C. and at a relatively high sulfur dioxide loading have been shown to provide a more effective hydrolysis.

In particular, it has been found that an effective sulfur dioxide dosage greater than about 0.8 wt %, and in particular greater than about 1 wt %, an effective sulfur dioxide slurry concentration between about 0.25 wt % and 2.5 wt %, and/or at final pH values less than about 1.5, provide very efficient hydrolyses, particularly when compared to conventional sulfuric acid pretreatment. In general, an efficient hydrolysis may be recognized by a relatively high glucose conversion, the use of relatively less enzyme, and/or a relatively short hydrolysis time.

Figure 7:
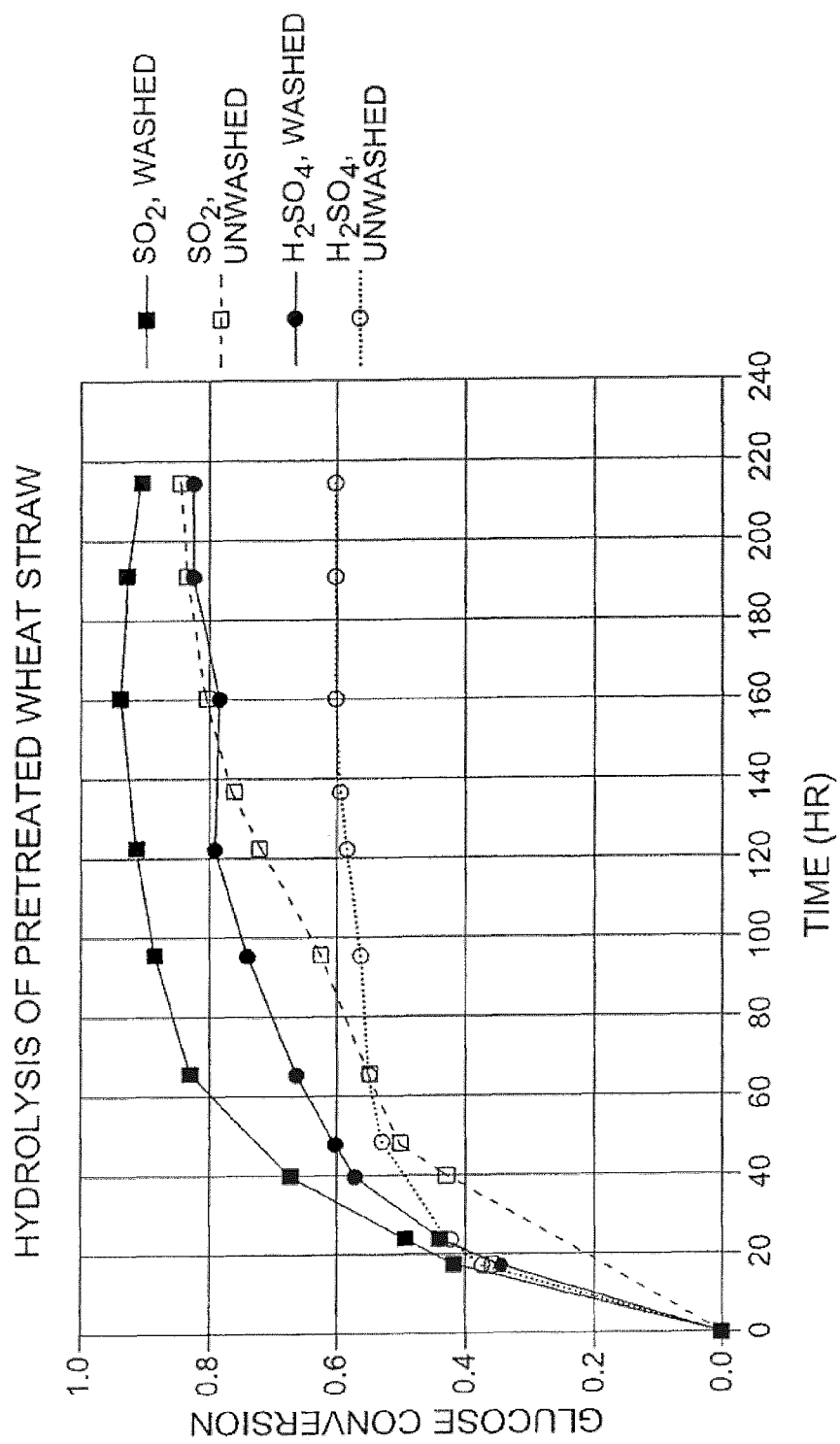
FIG. 7 is a plot of glucose conversion versus hydrolysis time for hydrolysis of $SO_2$ and $H_2SO_4$ catalyzed pretreated material.

A comparison of a $SO_2$ catalyzed pretreatment conducted at a sulfur dioxide dosage greater than about 10% relative to a conventional $H_2SO_4$ catalyzed pretreatment is provided in FIG. 7. More specifically, FIG. 7 shows the glucose conversion for a hydrolysis following a sulfur dioxide catalyzed pretreatment wherein the effective sulfur dioxide dosage is approximately 2.2 wt %, the effective sulfur dioxide slurry concentration is 0.89 wt %, and the final pH is less than 1.5.

In particular, FIG. 7 shows the glucose conversion for washed and unwashed samples prepared by pretreating straw with $SO_2$ and for washed and unwashed samples prepared by pretreating straw with $H_2SO_4$. The preparation of the samples is discussed in the Examples. Referring again to FIG. 7, the glucose conversion achieved for $SO_2$ catalyzed pretreatment conducted at relatively high sulfur dioxide dosage (e.g., $SO_2$ washed) is higher than the glucose conversion achieved for conventional $H_2SO_4$ catalyzed pretreatment (e.g., $H_2SO_4$ washed), thus showing improved efficiency. Alternatively, or additionally, improved efficiency is recognized by the fact that the $SO_2$ catalyzed washed sampled reached 0.8 glucose conversion in about 60 hours, while the $H_2SO_4$ catalyzed washed sample took about 160 hours to reach 0.8 glucose conversion.

As discussed above, and as illustrated in FIG. 7, an improved hydrolysis may be provided when the pretreatment is conducted such that the effective sulfur dioxide dosage is approximately 2.54 wt % (e.g., above 0.8 wt %), while the effective sulfur dioxide slurry concentration is approximately 1.07 wt % (e.g., between 0.25 wt % and 1.5 wt %), and the final pH is less than 1.5.

Figure 8:
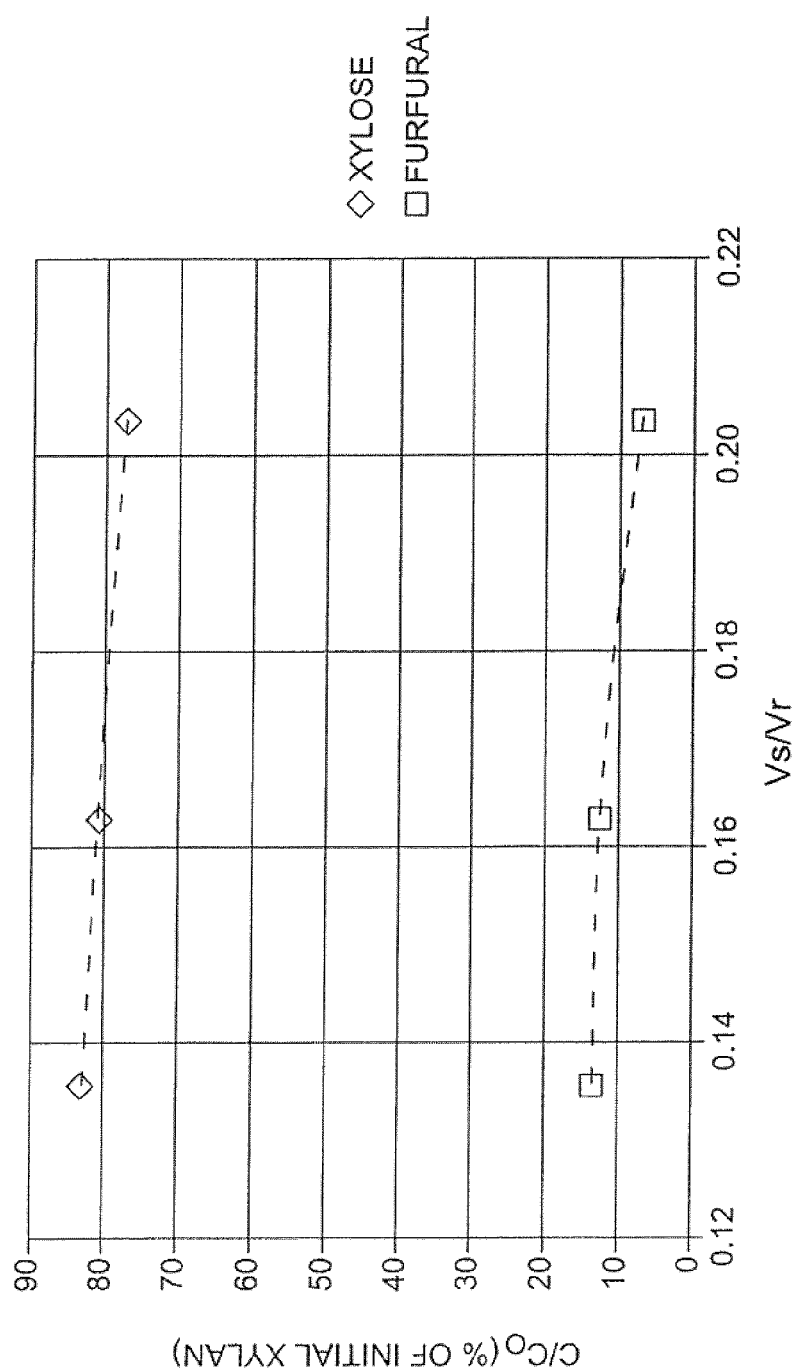
FIG. 8 is a plot illustrating xylose produced as a function of $V_s/V_r$ for a slurry having a consistency of about 30 wt %.

In order to explore various concentration ranges and/or the role of the ratio $V_s/V_r$ on pretreatment, various experiments were conducted using pretreatment reactors having different volumes, as illustrated in Example 11. Referring to FIG. 8, the results indicate that xylose concentration (e.g., and thus xylan dissolution) increases with decreasing $V_s/V_r$ (e.g., increasing headspace). Without being bound by theory, the increased xylan dissolution may be related to providing optimum sulfur dioxide concentrations in the vapour phase and/or in solution.

EXAMPLES

Example 1: $SO_2$ Catalyzed Pretreatment of Lignocellulosic Material

An $SO_2$ catalyzed batch pretreatment of wheat straw was conducted in 25 mL, stainless steel, laboratory tubular reactors (i.e., about 5 inches in length). The wheat straw was hammer-milled such that a large portion of the particles was less than about 1 inch (2.54 cm) length and ¼ inch (0.635 cm) width. In general, less than 5% of the particles were longer than 2 inches (5.08 cm) and up to 10% of the particles were fines, the size of dust. The glucan content of the straw was 34.61%, the xylan content was 20.09%, and the lignin content was 20.49% on a dry basis. The total solids (TS) content of the straw was 93.25%, which equates to 6.75% moisture. The carbohydrate assay was based on Determination of Structural Carbohydrates and Lignin in Biomass-LAP (Technical Report NREL/TP-510-42618).

Each tubular reactor was charged with approximately 1.646 g of accurately weighed wheat straw and 3.47 mL (3.57 g with a density of 1.03 g/ml) of sulfurous acid solution (>6% $H_2SO_3$, from Sigma-Aldrich), thus providing a slurry having a consistency of about 30 wt % and a pH of 1.1 measured at ambient conditions.

The sulfur dioxide dosage, which in this case is the same as the sulfur dioxide loading, is calculated as follows:

$$SO_{2(Total,dry)} = \frac{\text{g SO2 added}}{\text{g biomass added} * TS \text{ content}} \quad (7)$$

$$= \frac{\text{volume H2SO3 (mL) added} * \frac{6 \text{ g}}{100 \text{ mL}} * \frac{Mw \text{ SO2}}{Mw \text{ H2SO3}}}{\text{g biomass added} * TS \text{ content}}$$

$$= \frac{3.47 * 6 * 64.066/(100 * 82.07)}{1.646 * 0.9325}$$

$$= 10.6 \text{ wt \% (i.e., on solids)}$$

The total moisture present in the biomass is given as 1.646 g*6.75% moisture=0.11 g. The total mass of moisture in the reactor is 3.57 g+0.11 g=3.68 g.

The volume of the slurry is calculated as follows:

$$V_S = \frac{\text{mass of slurry added}}{\text{density of slurry}} \quad (8)$$

$$= \frac{3.57 + 1.646 \text{ g}}{1.00 \frac{\text{g}}{\text{mL}} \text{(assumed)}}$$

$$= 5.23 \text{ mL}$$

Figure 11:
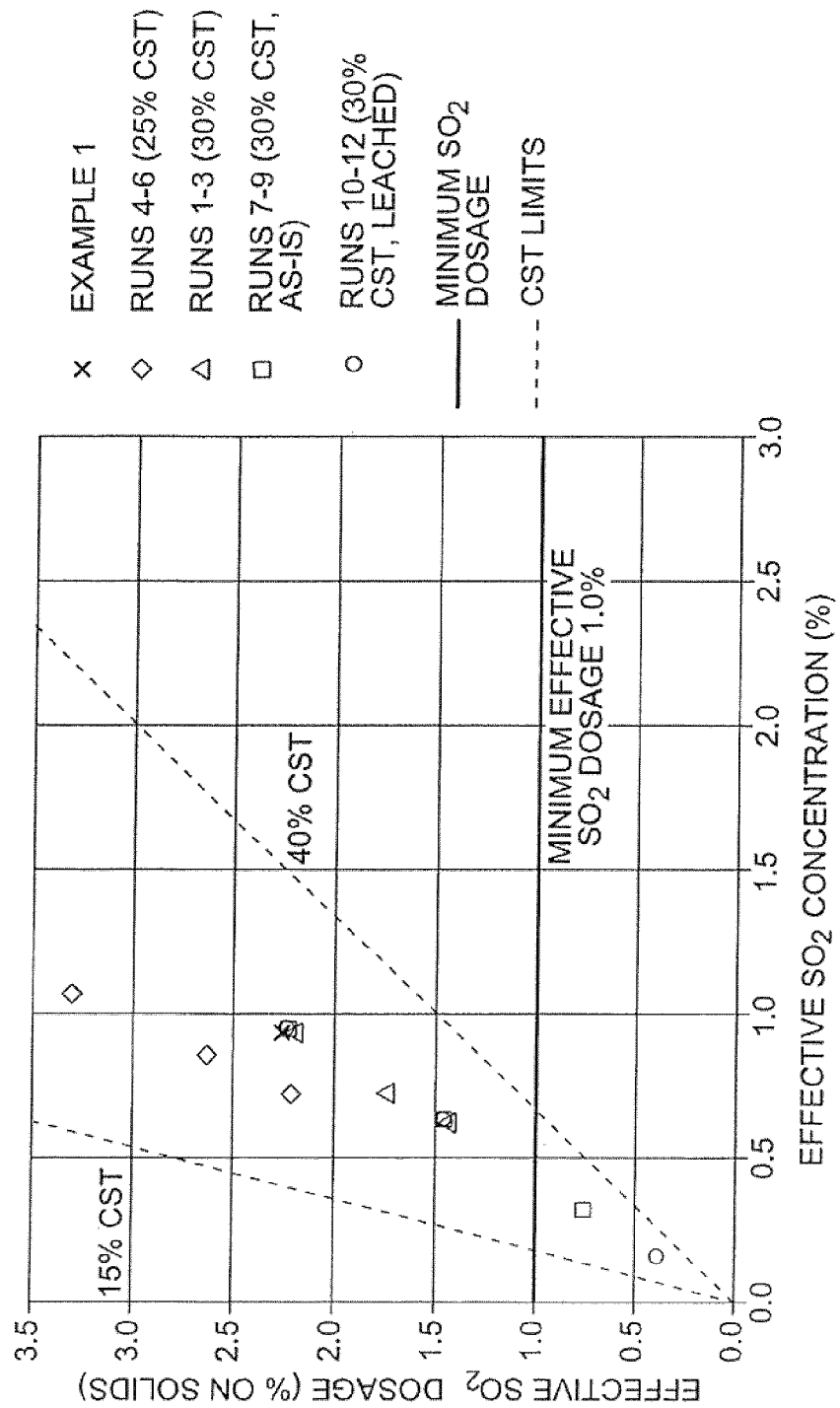
FIG. 11 is a graph illustrating the volume adjusted sulfur dioxide dosage and volume adjusted sulfur dioxide concentration corresponding to different runs.

The ratio of the volume of slurry to the total volume of the pretreatment reactor, $V_s/V_r$=5.23/25=0.209. Accordingly, the effective sulfur dioxide dosage is given as approximately 2.22 wt % (i.e., 10.6 wt %*0.209), whereas the effective sulfur dioxide slurry concentration is given as 0.92 wt % (i.e., 0.209*(6%*3.47 ml/3.68 g)*(64.07/82.07)*100%). This operating point is shown in FIG. 11 with an X.

Each tubular reactor was repeatedly shaken/inverted and then placed in an oil bath preheated to 195° C. The tubular reactor remained immersed in the oil bath for 5 minutes. At the end of the 5 minute pretreatment time, the tubular reactor was removed from the oil bath, suspended in air for about 10 seconds to allow oil to drip off the sides, and placed in an ice bath for 5 minutes. Four such pretreatment reactions were carried out at identical conditions to provide enough material for analysis and subsequent processing. The contents of the tubular reactors (e.g., pretreated material) were removed, weighed, and combined in a sealable plastic bag.

A portion of the pretreated material was removed for washing, to prepare a washed pretreatment sample for hydrolysis. Another portion of the pretreated material was removed to prepare an unwashed pretreatment sample for hydrolysis. The washed and unwashed samples were subject to enzymatic hydrolysis starting on the same day as the pretreatment.

A portion of the pretreated material was reserved to determine the undissolved solids (UDS) concentration, total solids (TS) concentration, dissolved solids (DS) concentration, and/or the concentration of monomeric sugars and/or degradation products.

More specifically, the filtrate collected by a 0.22-micron filter paper in a syringe from a portion of the $SO_2$ pretreated material was found to contain 9.77 g/L glucose, 75.42 g/L xylose, 0.21 g/L HMF and 4.36 g/L of furfural, using the method described in Example 6.

The carbohydrate content of the $SO_2$ pretreated material was ascertained with a carbohydrate assay based on Determination of Structural Carbohydrates and Lignin in Biomass-LAP (Technical Report NREL/TP-510-42618). The $SO_2$ pretreated material was found to contain 57.84% cellulose, 1.61% xylan and 27.88% insoluble lignin, w/w on a dry basis.

All experiments conducted with or based on $SO_2$/sulfurous acid are carried out in a fume hood, including the drying of samples for determining the dissolved solids and total solids concentrations.

Example 2: $H_2SO_4$ Catalyzed Pretreatment of Lignocellulosic Material

A $H_2SO_4$-catalyzed batch pretreatment of wheat straw was conducted in a 97 L steam gun, for comparison with the $SO_2$ catalyzed pretreatment. The wheat straw was hammer-milled such that a large portion of the particles were about 1 inch (2.54 cm) length and ¼ inch (0.635 cm) width. In general, less than 5% of the particles were longer than 2 inches (5.08 cm) and up to 10% of the particles were fines, the size of dust. The straw had a glucan content of 34.61%, a xylan content of 20.09%, a lignin content of 20.49%, on a dry basis. The total solids content of the straw was 89.5%, which equates to 10.5% moisture.

To prepare for pretreatment, 400 g of the milled wheat straw was soaked overnight in a solution prepared from 22.3 mL of 96.5% $H_2SO_4$ and 6.72 L of water, thus providing a slurry having a consistency of about 5% and a pH of 1.30. Excess $H_2SO_4$ solution was drained from the wheat straw, which was then placed in a Bock basket centrifuge for 30 seconds. The centrifuged, $H_2SO_4$ soaked lignocellulosic feedstock, which had a total solids (TS) concentration of 29.18%, was then stored at about 4° C.

The steam gun, which was preheated by repeatedly heating to 200° C. with steam and venting, was charged with 1000 g of the centrifuged, $H_2SO_4$ soaked straw and cooked for 2 minutes. After 2 minutes, the steam gun was depressurized to less than 5 psig and the pretreated straw was removed from the steam gun. The pretreated material, which weighed 948.5 g and had a UDS of 19.63 wt %, was cooled before storage at about 4° C.

A portion of the pretreated material was removed for washing, to prepare a washed pretreatment sample for hydrolysis. Another portion of the pretreated material was removed to prepare an unwashed pretreatment sample for hydrolysis.

A portion of the pretreated material was reserved to determine the undissolved solids (UDS) concentration, total solids (TS) concentration, dissolved solids (DS) concentration, and/or the concentration of monomeric sugars and/or degradation products.

More specifically, the filtrate generated by a Buchner funnel with 1.6-micron filter paper from a portion of the $H_2SO_4$ pretreated material contained 17.54 g/L glucose, 63.42 g/L xylose, 0.45 g/L HMF and 1.89 g/L of furfural.

The carbohydrate content of the $H_2SO_4$ pretreated material was ascertained with a carbohydrate assay based on Determination of Structural Carbohydrates and Lignin in Biomass-LAP (Technical Report NREL/TP-510-42618). The $H_2SO_4$ pretreated material was found to contain 54.33% cellulose, 1.40% xylan, and 29.72% insoluble lignin, w/w on a dry basis.

Example 3: Determination of Undissolved Solids Concentration

The determination of the undissolved solids (UDS) content, also referred to as the consistency, is carried out as follows. A fixed amount of a sample containing undissolved solids is dispensed into a plastic weigh dish and the weight is recorded accurately using an analytical scale. A glass microfiber filter paper circle of pore size 1.6 microns, appropriately sized for a Buchner funnel, is placed in an aluminum weighing tin and the combined weight of the tin and filter paper is recorded. After transferring the pre-weighed filter paper to the Buchner funnel, the pre-weighed sample is passed through the filter paper to isolate the solids. Small volumes of de-ionized water are used to ensure that the solids are quantitatively transferred from the weigh dish to the Buchner funnel. The solids are then washed using excess deionized water, after which the washed sample and filter paper are transferred into the pre-weighed aluminum tin. Care should be taken to ensure the solids are quantitatively transferred. After drying the aluminum tin in a 105° C. oven overnight, the contents are weighed accurately and the UDS is quantified by determining, as a percent, the number of grams of dry solids per gram of sample. UDS measurements are performed in duplicate and averaged.

UDS measurements are performed on unwashed pretreated samples to determine the amount of pretreated sample to add to the hydrolysis flask (e.g., using about 0.5 g aliquots).

Example 4: Measurement of Total Solids Concentration in a Pretreated Feedstock Composition The determination of the total solids (TS) content is carried out as follows. A fixed amount of a sample is dispensed into a pre-weighed aluminum tin (if sample is washed) or crucible (if sample is unwashed). After drying the aluminum tin/crucible in a 105° C. oven or muffle furnace (disposed in a fume hood) overnight, the contents are weighed accurately and the total solids are quantified by determining, as a percent, the number of grams of dry solids per gram of sample. TS measurements are performed in duplicate and averaged.

TS measurements are performed on washed pretreated samples to determine the amount of pretreated sample to add to the hydrolysis flask (e.g., using about 0.5 g aliquots).

TS measurements are performed on unwashed pretreated samples as an alternate method for determining the concentration of dissolved solids.

Example 5: Measurement of Dissolved Solids Concentration in a Pretreated Feedstock Composition The determination of the dissolved solids concentration of a pretreated feedstock composition is carried out as follows. A glass microfiber filter paper circle of pore size 1.6 microns that has not been pre-wetted is placed in a Buchner funnel.

A sample of a pretreated feedstock composition is applied to the filter paper and filtered by vacuum. The filtrate is collected and weighed into a pre-weighed crucible. After drying the crucible in a 105° C. muffle furnace (placed in a fume hood) overnight, the contents are weighed accurately and the concentration of dissolved solids is quantified by determining, as a percent, the number of grams of dry solids per gram of filtrate.

Alternatively, the concentration of dissolved solids (% DS) is obtained from $$\% \text{ DS} = \% \text{ TS} - \% \text{ UDS} \quad (9)$$

Example 6: Determination of the Concentration of Monomeric Sugars and/or Degradation Products Determination of the concentration of monomeric sugars and/or degradation products, such as furans, was achieved using high performance liquid chromatography (HPLC).

The sugar composition (e.g., concentration of glucose and/or xylose) of pretreated material and/or of aliquots from the enzymatic hydrolysis was determined using a Dionex ICS-3000 ion chromatography system equipped with an electrochemical detector (ED40) with gold electrode. Separation was performed on a CarboPac™ PA1 column (4×250 mm) and a PA1 guard column (4×50 mm). The detector temperature and column temperature were both 30° C. NaOH (10 and 200 mM solutions) was used as an eluent at a flow rate of 1.5 mL/min. All sample injection volumes were 25 µL. Sugar concentrations were calculated by comparison to standard sugar samples containing arabinose, galactose, glucose, xylose and cellobiose (Certified from Absolute Standards).

Concentration of furans (e.g., concentration of 5-(hydroxymethyl)furfural (HMF) and/or furfural) in the pretreated material and/or in aliquots from the enzymatic hydrolysis were determined using a Dionex ICS-3000 ion chromatography system equipped with a Dionex AD25 Absorbance detector set at 278 nm. Separation was performed on a Varian Microsorb-MV C18 (4×250 mm) and Phenomenex Security guard column with Carbo-H cartridges. Detector temperature and column temperature were both 30° C. A solution of 5:95 (v/v) ACN:deionized water was used as an eluent at a flow rate of 1 mL/min. All sample injection volumes were 25 Furan concentrations were calculated by comparison to standard furan samples containing 5-(Hydroxymethyl)furfural (HMF), furfuryl alcohol, and furfural (certified from Absolute Standards).

The filtrate from a portion of the $SO_2$ pretreated material from Example 1 was found to contain 9.77 g/L glucose, 75.42 g/L xylose, 0.21 g/L HMF, and 4.36 g/L of furfural.

The filtrate from a portion of the $H_2SO_4$ pretreated material from Example 2 was found to contain 17.54 g/L glucose, 63.42 g/L xylose, 0.45 g/L HMF, and 1.89 g/L of furfural.

Example 7: Preparation of the Washed Pretreatment Samples for Hydrolysis

Washed pretreatment samples were prepared by suspending a portion of pretreated sample in ultra-purified water (Milli-Q™) in an approximately 1:1 (v/v) ratio, filtering the suspension through glass fiber filter paper (G6, 1.6 microns), and then repeating the alternating steps of adding the same volume of ultra-purified water (Milli-Q™) to the pretreated solids followed by filtration through the glass fiber filter paper, another eight times.

The washed pretreatment solids were added to a pre-weighed 50 mL Erlenmeyer flask, in an amount selected to provide a consistency of about 10 wt % for hydrolysis (e.g., corresponding to about 1 g of dry pretreated material for a total weight of the flask contents, including the enzyme, of 10 g). To determine the amount of wet, washed pretreatment solids that corresponds to 1 g of dry pretreatment material, 1 g is divided by the total solids (TS) of the washed pretreated sample.

In the washed $SO_2$ catalyzed pretreatment samples prepared according to Examples 1 and 7, the TS was found to be 21.43%, thus providing a target weight of wet slurry to be added to the Erlenmeyer flask of 4.6662 g.

Once an accurately weighed amount of washed pretreatment solids (target weight of 4.6662 g) has been added to the Erlenmeyer flask, 0.420 mL sodium citrate (2.38 M of citrate buffer pH adjusted to 5.2 with 30% NaOH) was added to the flask (e.g., an amount selected to provide a target 100 mM concentration once the enzyme is added). Ultra-purified water (Milli-Q™) was then added to bring the flask contents up to a target weight, predetermined to bring the final weight of the contents to 10 g once enzyme is added. The flasks were incubated at 52° C., with moderate shaking at about 250 rpm, for 30 minutes to equilibrate substrate temperature.

Example 8: Preparation of the Unwashed Pretreatment Samples for Hydrolysis

Unwashed pretreatment samples were prepared by adjusting the pH of a portion of the as-is pretreated material to about 5 by adding a solution of 30% lime ($Ca(OH)_2$) in small increments. The pH-adjusted pretreatment material was then added to a pre-weighed 50 mL Erlenmeyer flask, in an amount selected to provide a consistency of about 10 wt % for hydrolysis (e.g., corresponding to about 1 g of dry pretreated material for a total weight of the flask contents, including the enzyme, of 10 g). To determine the amount of pretreated slurry that corresponds to 1 g of dry pretreatment material, 1 g is divided by the UDS of the pH adjusted pretreated sample.

In the unwashed $SO_2$ catalyzed pretreatment samples prepared according to Example 1, the UDS of the pH-adjusted pretreated sample was found to be 17.42%, thus providing a target weight of wet slurry to be added to the Erlenmeyer flask of 5.7389 g.

Once an accurately weighed amount of unwashed slurry (target weight of 5.7389 g) has been added to the Erlenmeyer flask, 0.420 mL of 2.38 M sodium citrate buffer (prepared by adjusting the pH of citric acid monohydrate to about 5.2 with 30% NaOH) was added to the flask (e.g., an amount selected to provide a target 100 mM concentration once enzyme). Ultra-purified water (Milli-Q™) was then added to bring the flask contents up to a target weight, predetermined to bring the final weight of the contents to 10 g once enzyme is added. The flasks were incubated at 52° C., in an orbital shaker (250 rpm), for 30 minutes to equilibrate substrate temperature.

Example 9: Enzymatic Hydrolysis of Pretreated Samples

Hydrolysis was initiated by adding liquid cellulase enzyme to the Erlenmeyer flasks prepared in Examples 7 and 8 (i.e., containing the pretreated material, citrate buffer, and make-up water), thus bringing the total content weight up to 10 g. Enzyme was added at a dosage of 5 mg/g (i.e., mg protein/g of cellulose). The flasks were incubated at 52° C. in an orbital shaker (250 rpm) for 215 hours.

The pH of the washed samples were maintained at about 5 (e.g., between 4.8 and 5.2) for the duration of the hydrolysis by the citrate buffer. The pH of the unwashed samples were periodically adjusted to 5 (i.e., twice a day for the first 72 hours of hydrolysis, and once a day for the remaining duration of the hydrolysis). The pH was adjusted by adding a solution of 30% lime ($Ca(OH)_2$) in 10 µL increments by using a 50 µL Eppendorf pipet. The volume of pH adjusting solution added was recorded, and used to adjust total volume when calculating cellulose conversion.

The hydrolyses were followed by measuring the sugar monomers in the hydrolysate. More specifically, aliquots obtained at 16, 24, 40, 48, 60, and 72 hours of hydrolysis, and at 24 hours intervals after the 72 hours, were used to analyze the sugar content. Each aliquot was obtained at the specific time interval by swirling the flask, withdrawing 200 µL of the flask contents with a wide-bore pipette tip and depositing it in a 1.5 mL Eppendorf centrifuge tube, placing the centrifuge tube in a boiling water for 10 minutes to deactivate the enzyme, and storing the aliquot at about 4° C. for subsequent sugar analysis.

To assay samples for monomeric sugars, the samples were warmed to room temperature and were centrifuged for 4 minutes at 14,800 rpm. The supernatant was diluted in water for measuring the glucose with the HPLC, and were measured using the method in Example 6.

Since the slurries in the hydrolysis flasks were too thick at time 0 hours, the glucose measurements at time 0 hours was calculated using the glucose concentration measured for the corresponding filtrate, the enzyme solution glucose contribution, and the total volume of the contents of the corresponding hydrolysis flask, which includes volume added from the lime addition, buffer solution, make-up water, and enzyme addition.

The glucose conversion was determined assuming:

$$\text{Max. glucose} = \left(\frac{\text{g of dry substrate} * \% \text{ cellulose in the substrate}}{\text{aqueous volume (L)}}\right) * \left(\frac{180.1559 \text{ g/mol}}{162.16 \text{ g/mol}}\right) \quad (10)$$

$$\text{Glucose conversion} = \frac{\text{concentration of glucose in aliquot}}{\text{maximum glucose}} \quad (11)$$

The values of maximum glucose are 67.9 g/L for the $SO_2$-catalyzed pretreatments and 52.9 g/L for the sulfuric acid-catalyzed pretreatments. The results are presented in FIG. 7. More specifically, FIG. 7 shows a plot of glucose conversion as a function of time for both washed and unwashed samples, for both $SO_2$ and $H_2SO_4$ catalyzed pretreatments, with a 5 mg/g enzyme loading.

Referring to the assays referred to in Examples 1 and 2, the $SO_2$ catalyzed pretreatment resulted in more cellulose (e.g., 57.84% compared to 54.22%), more xylan (1.61% compared to 1.40%), and less insoluble lignin (e.g., 27.88% compared to 29.72%), relative to the $H_2SO_4$ catalyzed pretreatment. In addition, the filtrate from the $SO_2$ catalyzed pretreatment resulted in less glucose (9.77 g/L compared to 17.54 gL), more xylose (75.42 g/L compared to 63.42 g/L), less HMF (0.21 g/L compared to 0.45 g/L), and more furfural (4.36 g/L compared to 1.89 g/L), relative to the $H_2SO_4$ catalyzed pretreatment.

Referring to FIG. 7, hydrolysis of the $SO_2$ catalyzed pretreatment washed sample reached about 0.9 glucose conversion at 160 hours, whereas hydrolysis of the $H_2SO_4$ catalyzed pretreatment washed sample only reached 0.8 glucose conversion at 160 hours. By comparison, hydrolysis of the $SO_2$ catalyzed pretreatment unwashed sample reached 0.8 glucose conversion at 160 hours, whereas hydrolysis of the $H_2SO_4$ catalyzed pretreatment unwashed sample only reached 0.6 glucose conversion at 160 hours.

Although the hydrolysis of each washed pretreated material was generally more efficient than the hydrolysis of the corresponding unwashed pretreated material, the surprising result is that the hydrolysis of the unwashed $SO_2$ catalyzed pretreatment material reached substantially the same, or higher, glucose conversion as the hydrolysis of the washed $H_2SO_4$ catalyzed pretreatment material at times over 160 hours. In particular, even though the hydrolysis of the unwashed $SO_2$ catalyzed pretreatment material started out relatively slowly (e.g., slow relative to the hydrolysis of the unwashed $H_2SO_4$ catalyzed pretreatment material), with time it eventually surpassed the glucose conversion obtained by hydrolysis of the washed $H_2SO_4$ catalyzed pretreatment material. Accordingly, without being bound by theory, it does not appear that there is a high concentration of inactivating compounds in the unwashed $SO_2$ catalyzed pretreatment material (e.g., for comparison, the hydrolysis of the $H_2SO_4$ catalyzed pretreatment material plateaus around 0.6, thus indicating at least some inactivation of the enzyme).

Advantageously, since the hydrolysis of the unwashed $SO_2$ catalyzed pretreatment material reached substantially the same, or a higher, glucose conversion as the hydrolysis of the washed $H_2SO_4$ catalyzed pretreatment material, the $SO_2$ catalyzed pretreatment may provide a reasonable alternative to $H_2SO_4$ catalyzed pretreatment, even when the pretreated material is not washed and/or diluted before being fed to hydrolysis. Although the cost of $SO_2$ catalyzed pretreatment may be more than the cost of $H_2SO_4$ catalyzed pretreatment (e.g., due to the cost of $SO_2$ compared to $H_2SO_4$, and due to the required equipment, including $SO_2$ recovery) this cost may be offset by providing little to no washing and by the reduction in the amount of enzyme required. For example, preliminary experiments have indicated that $SO_2$ pretreatment may use less than 50% of the enzyme conventionally used for hydrolyzing $H_2SO_4$ catalyzed pretreated materials, while still providing a high glucose conversion. In addition, since the $SO_2$ may be recovered in a sulfur recovery unit, the costs may be further reduced.

In general, an efficient hydrolysis may exploit a relatively high glucose conversion, use less enzyme, and/or have shorter hydrolysis times. For example, referring again to FIG. 7, high efficiency hydrolysis of $SO_2$ catalyzed pretreated material is demonstrated by the high glucose conversion of the $SO_2$ washed sample, and/or by the fact that the $SO_2$ catalyzed washed sampled reached 0.8 glucose conversion in about 60 hours, while the $H_2SO_4$ catalyzed washed sample took 160 hours to reach 0.8 glucose conversion.

Example 10: Determining the Glucan, Xylan, and Lignin Content

As described above, the cellulose/glucan content, xylan content, and/or lignin content discussed in Examples 1 and 2 is determined by a carbohydrate assay based on Determination of Structural Carbohydrates and Lignin in Biomass-LAP (Technical Report NREL/TP-510-42618). In particular, the carbohydrate assay was modified specifically for wheat straw and/or pretreated wheat straw. For example, the wheat straw sample was treated with 69 wt % sulfuric acid, wherein 1.5 mL of sulfuric acid is provided per 0.15 g of sample. The sample was incubated in a water bath at 50° C. for 30 minutes. An additional 43.5 mL water was added to provide an acid concentration of about 3.6 wt % $H_2SO_4$. The sample was then set in an autoclave set at 116° C. for 50 minutes. Once the sample was cooled, the determination of carbohydrate content, and in particular the sugar monomers, was determined using high performance liquid chromatograph (HPLC). A sugar recovery standard (SRS) containing known concentrations of arabinose, galactose, glucose, xylose, and 3.6 wt % $H_2SO_4$ was also placed in an autoclave set 116° C. for 50 minutes. The determination of sugar monomers in the SRS was used to correct for losses due to decomposition of the sugars. In particular, the corrected xylan and/or glucan content was determined using the following equation:

$$\frac{Carbohydrate_{corrected}(\text{mg})}{\text{fiber g}} = \frac{\frac{monomeric\ sugar_{HPLC}(\text{g/L})}{\%\ R_{SRS}/100} \times Volume\ Diluted\ (\text{mL}) \times MW\ ratio}{Wt\ of\ sample\ (\text{g}) \times \%\ total\ solids\ content} \times 100 \quad (12)$$

where $$\%\ R_{SRS} = \frac{(C_{sugar\ HPLC}(\text{g/L})\ in\ SRS)_{autoclaved}}{(C_{sugar\ HPLC}(\text{g/L})\ in\ SRS)_{nonautoclaved}} \times 100, \quad (13)$$

% $R_{SRS}$=Percent recovery for individual sugar in sugar recovery standard
$C_{sugar}$=Concentration of individual sugar, and
MW ratio=molecular weight ratio of polymeric sugar ($C_5$ or $C_6$) to monomeric sugar ($C_5$ or $C_6$)
For calculating xylan content, $$MW\ ratio = \quad (14)$$

$$\frac{MW\ repeating\ unit}{2 \times MW\ C5} = \frac{MW\ C_{10}H_{16}O_8}{2 \times MW\ C_5H_{10}O_5} = \frac{264.23}{2 \times 150.13} = 0.88$$

For calculating glucan content, $$MW\ ratio = \quad (15)$$

$$\frac{MW\ repeating\ unit}{2 \times MW\ C6} = \frac{MW\ C_{12}H_{20}O_{10}}{2 \times MW\ C_6H_{12}O_6} = \frac{324.28}{2 \times 180.15} = 0.90$$

The calculated lignin content corresponds to the acid-insoluble lignin.

Example 11: Demonstration of Effective SO2 Concentration and Dosage by Varying the Headspace Volume The effect of headspace volume, and in particular $V_s/V_r$, on the effectiveness of the $SO_2$ pretreatment was examined by conducting $SO_2$ catalyzed batch pretreatment of wheat straw in three laboratory tubular reactors having different volumes (i.e., 25 mL, 31.25 mL, and 37.5 mL). Each reactor was formed from a stainless steel tube (i.e., about 5, 6.25, and 7.5 inches in length and about 9/16 inch internal diameter). Each end of each tube was secured with a hex Swagelok fitting and cap.

The wheat straw was hammer-milled to provide an average particle size of about ¼ inch (0.635 cm) and had a glucan content of 34.61% and a total solids (TS) content of 91.6 wt %, on a dry basis. The carbohydrate assay used to determine the glucan content was based on Determination of Structural Carbohydrates and Lignin in Biomass-LAP (Technical Report NREL/TP-510-42618).

To prepare samples having a consistency of about 30 wt %, each tubular reactor was charged with approximately 1.64 g of accurately weighed wheat straw (i.e., corresponding to about 1.5 g, on a dry basis) and 3.35 mL (3.45 g at a density of 1.03 g/ml) of sulfurous acid solution (≥6% $H_2SO_3$, from Sigma-Aldrich), and the reactor sealed.

The sulfur dioxide dosage, which in this case is the same as the sulfur dioxide loading, is calculated as follows:

$$SO_{2(Total, dry)} = \frac{\text{g SO2 added}}{\text{g biomass dry}} \quad (16)$$

$$= \frac{volume\ H2SO3\ (\text{mL})\ added * \frac{6\ \text{g}}{100\ \text{mL}} * \frac{Mw\ SO2}{Mw\ H2SO3}}{\text{g biomass added} * TS\ content}$$

$$= \frac{3.35 * 6 * 64.066/(100 * 82.07)}{15}$$

$$= 10.5\ \text{wt \%}\ (\text{i.e., on dry solids})$$

The total moisture present in the biomass is 0.14 g (e.g., where 1.64 g−1.5 g=0.14 g). The total mass of moisture in the reactor is 3.45 g+0.14 g=3.59 g.

The sulfur dioxide slurry concentration is calculated as follows:

$$SO_{2(Total, wet)} = \frac{\text{g SO2 added}}{\text{g moisture}} \quad (17)$$

$$= \frac{volume\ H2SO3\ (\text{mL})\ added * \frac{6\ \text{g}}{100\ \text{mL}} * \frac{Mw\ SO2}{Mw\ H2SO3}}{\text{g moisture}}$$

$$= \frac{3.35 * 6 * 64.066/(100 * 82.07)}{3.59}$$

$$= 4.45\ \text{wt \%}$$

The volume of the slurry is calculated as follows:

$$V_S = \frac{\text{mass of slurry added}}{\text{density of slurry}} = \frac{1.64\ \text{g} + 3.45\ \text{g}}{1.0\frac{\text{g}}{\text{mL}}(\text{assumed})} = 5.09\ \text{mL} \quad (18)$$

The ratio of the volume of slurry to the total volume of the pretreatment reactor, $V_s/V_r$=5.09/25=0.204, 5.09/31.25=0.163, and 5.09/37.5=0.136, for the three different runs.

Each tubular reactor was placed in a 26 L oil bath preheated to 195° C., where it remained submerged for 5 minutes. At the end of the 5 minute pretreatment, each tubular reactor was removed from the oil bath, suspended in air for 10 seconds to allow oil to drip from the sides, and placed into an ice bath to cool.

The pH of the pretreated slurry was measured, and the concentration of xylose and furfural from each reactor was measured according to Example 6, and compared to the initial xylan concentration, measured according to Example 10, to provide $C/C_o$. The results are shown in FIG. 8 and/or Table 1. The operating points are shown in FIG. 11.

TABLE 1

Effect of headspace on pretreatment for a slurry having a consistency of about 30%

| Run | Length (inches) | $V_r$ (mL) | $V_s$ (mL) | $V_h$ (mL) | $V_s/V_r$ | $SO_{2(VA,dry)}$ (wt %) | $SO_{2(VA, wet)}$ (wt %) | $C/C_o$ Xylose (%) | $C/C_0$ Furfural (%) | Final pH |
|---|---|---|---|---|---|---|---|---|---|---|
| 1 | 5 | 25 | 5.09 | 19.91 | 0.204 | 2.14 | 0.91 | 77.2 | 6.3 | 1.06 |
| 2 | 6.25 | 31.25 | 5.09 | 26.2 | 0.163 | 1.71 | 0.72 | 80.9 | 11.9 | 0.93 |
| 3 | 7.5 | 37.5 | 5.09 | 32.41 | 0.136 | 1.43 | 0.60 | 82.7 | 12.6 | 0.96 |

Accordingly, the effective sulfur dioxide dosage is given as approximately 2.14 wt %, whereas the effective sulfur dioxide slurry concentration is given as 0.91 wt %, for the pretreatment conducted in the 25 mL tube reactor.

To prepare samples having a consistency of about 25 wt %, each tubular reactor was charged with approximately 1.5 g of accurately weighed wheat straw (dry) and 4.35 mL (4.48 g at a density of 1.03 g/ml) of sulfurous acid solution (≥6% $H_2SO_3$, from Sigma-Aldrich), and the reactor sealed.

The sulfur dioxide dosage, which in this case is the same as the sulfur dioxide loading, is calculated as follows:

$$SO_{2(Total,dry)} = \frac{\text{g SO2 added}}{\text{g biomass dry}} \quad (19)$$

$$= \frac{\text{volume H2SO3 (mL) added} * \frac{6 \text{ g}}{100 \text{ mL}} * \frac{Mw \text{ SO2}}{Mw \text{ H2SO3}}}{\text{g biomass added} * TS \text{ content}}$$

$$= \frac{4.35 * 6 * 64.066/(100 * 82.07)}{1.5}$$

$$= 0.20/1.5$$

$$= 13.3 \text{ wt \%}$$

The total moisture present in the biomass is 0.14 g (e.g., where 1.64 g−1.5 g=0.14 g.) The total mass of moisture in the reactor is 4.48 g+0.14 g=4.62 g.

The sulfur dioxide slurry concentration is calculated as follows:

$$SO_{2(Total,dry)} = \frac{\text{g SO2 added}}{\text{g moisture}} \quad (20)$$

-continued $$= \frac{\text{volume H2SO3 (mL) added} * \frac{6 \text{ g}}{100 \text{ mL}} * \frac{Mw \text{ SO2}}{Mw \text{ H2SO3}}}{\text{g biomass added} * TS \text{ content}}$$

$$= \frac{4.35 * 6 * 64.066/(100 * 82.07)}{4.62}$$

$$= \frac{0.20}{4.62}$$

$$= 4.33 \text{ wt \%}$$

The volume of the slurry is calculated as follows:

$$V_S = \frac{\text{mass of slurry}}{\text{density of slurry}} = \frac{1.64 \text{ g} + 4.48 \text{ g}}{1.0 \frac{\text{g}}{\text{mL}} \text{(assumed)}} = 6.12 \text{ mL} \quad (21)$$

The ratio of the volume of slurry to the total volume of the pretreatment reactor, $V_s/V_r$=6.12/25=0.245, 6.12/31.25=0.196, and 6.12/37.5=0.163, for the three different runs.

Each tubular reactor was placed in a 26 L oil bath preheated to 195° C., where it remained submerged for 5 minutes. At the end of the 5 minute pretreatment, the tubular reactor was removed from the oil bath, suspended in air for 10 seconds to allow the oil to drip from the sides, and placed into an ice bath to cool.

The pH of the pretreated slurries was measured, and the concentration of xylose and furfural from each reactor was measured according to Example 6, and compared to the initial xylan concentration, measured according to Example 10, to provide $C/C_o$. The results are shown in Table 2 and the operating points are shown in FIG. 11.

TABLE 2

Effect of headspace on pretreatment for a slurry having a consistency of about 25%

| Run | Length (inches) | $V_r$ (mL) | $V_s$ (mL) | $V_h$ (mL) | $V_s/V_r$ | $SO_{2(VA,dry)}$ (wt %) | $SO_{2(VA,wet)}$ (wt %) | $C/C_0$ Xylose (%) | $C/C_0$ Furfural (%) | Final pH |
|---|---|---|---|---|---|---|---|---|---|---|
| 4 | 5 | 25 | 6.12 | 18.88 | 0.245 | 3.26 | 1.06 | 84.3 | 6.9 | 1.05 |
| 5 | 6.25 | 31.25 | 6.12 | 25.13 | 0.196 | 2.61 | 0.85 | 74.1 | 10.4 | 0.99 |
| 6 | 7.5 | 37.5 | 6.12 | 31.38 | 0.163 | 2.17 | 0.71 | 86.5 | 13.6 | 0.99 |

As discussed above, the operating points corresponding to Runs 1-6 are shown in FIG. 11. More specifically, FIG. 11 shows that the effective $SO_2$ dosage, $SO_{2(VA, dry)}$, and the effective $SO_2$ slurry concentration, $SO_{2(VA, wet)}$, for these runs is within the preferred consistency limits (e.g., between about 15 wt % and about 40 wt %) of the embodiment illustrated in FIG. 2.

In addition, referring again to Tables 1 and 2 and FIG. 11, the effective $SO_2$ dosage, $SO_{2(VA, dry)}$, for these runs is above 1.0%, while the final pH of the pretreated slurries is below 1.5. Each of these experiments resulted in a xylose yield greater than 70%, which indicates good performance.

Referring to FIG. 8 and Tables 1 and 2, the xylan dissolution and/or degradation generally increases with increasing headspace volume and/or decreasing $V_s/V_r$. In particular, according to FIG. 8, the xylose concentration decreases with increasing $V_s/V_r$. While the reason why increased xylan dissolution is observed with increasing headspace and/or decreasing $V_s/V_r$ is not fully understood, it is believed to be related to the partitioning of sulfur dioxide between the vapor phase and the liquid phase.

Figure 9:
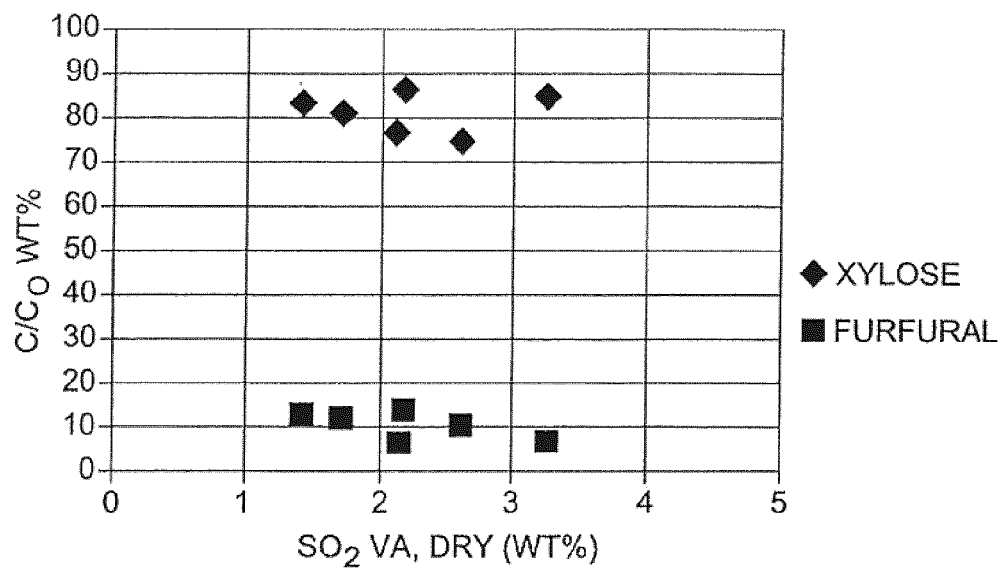
FIG. 9 is a plot illustrating xylose and furfural concentration (e.g., a weight percentage calculated with respect to initial xylan present) produced as a function of $SO_{2(VA,dry)}$ for slurries having a consistency of about 25 wt % and 30 wt %.
Figure 10:
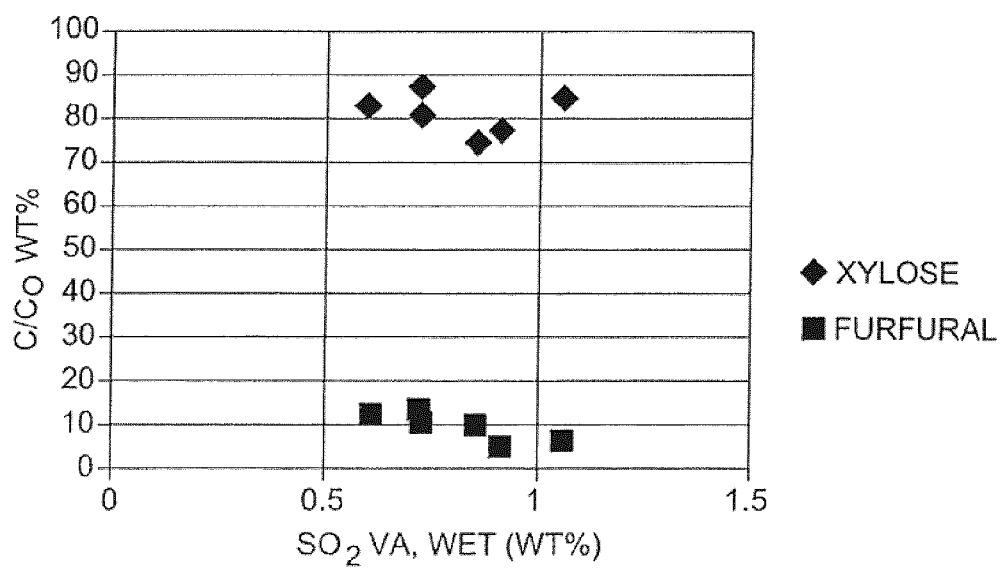
FIG. 10 is a plot illustrating xylose and furfural concentration (e.g., a weight percentage calculated with respect to initial xylan present) produced as a function of $SO_{2(VA,wet)}$ for slurries having a consistency of about 25 wt % and 30 wt %.

Referring to FIGS. 9 and 10, the $SO_{2(VA,dry)}$ and $SO_{2(VA,wet)}$ values from Tables 1 and 2, respectively, have been combined within the same data set and plotted against the xylose and furfural concentrations. Although there may be some scatter within the graphs since the experiments were not done in duplicate, a slight decrease in furfural concentration and possibly a slight increase in xylose yield is observed with increasing $SO_{2(VA,dry)}$ and/or $SO_{2(VA,wet)}$, within these ranges.

As discussed above, the data shown in Tables 1 and 2 and/or FIGS. 8, 9, and 10 indicate that the volume of the headspace, $V_h$, and in particular, a $V_s/V_r$, may influence the effectiveness of pretreatment. In addition, this data may indicate that in addition to the sulfur dioxide dosage, the effective sulfur dioxide dosage and/or effective sulfur dioxide slurry concentration may also influence the effectiveness of pretreatment. This also provides further support that the moisture level of the lignocellulosic feedstock slurry may be important in determining the level of pretreatment. In particular, this data further supports the preferred consistency range of the embodiment illustrated in FIG. 2 (e.g., between about 15 wt % and about 40 wt %), and in particular that in a consistency range between about 25 wt % and about 30 wt %, it may be advantageous to ensure the ratio $V_s/V_r$ is below about 0.6, and in particular, between about 0.10 and about 0.4. For example, reasonable pretreatments were achieved when the ratio $V_s/V_r$ was between about 0.1 and about 0.3.

Notably, comparison of Tables 1 and 2 may indicate that the use of higher consistencies and/or lower sulfur dioxide dosages may be used with higher $V_s/V_r$ values (e.g. relatively lower headspace volumes) while still providing good pretreatments, which is contrary to conventional steam gun practice, which traditionally uses relatively high consistencies in systems wherein $V_s/V_r$ is relatively low (e.g., less than 0.1).

While the concentration of xylose produced during pretreatment may provide a rough indication of the level of pretreatment, and thus the effectiveness of that the pretreatment, a more accurate indication of the effectiveness of the pretreatment is obtained by looking at the enzymatic hydrolysis results. For example, the effectiveness of pretreatment may be realized by a reduction in enzyme usage, a higher cellulose conversion, and/or a shorter hydrolysis time, in enzymatic hydrolysis.

It has been found that $SO_2$-catalyzed pretreatment may provide improved pretreatment, and in particular, may provide improved pretreatment when the pretreatment conditions are selected such that the effective sulfur dioxide dosage on solids is greater than about 0.8 wt %, and in particular, greater than about 1 wt %, the effective sulfur dioxide slurry concentration is between about 0.25 wt % and about 1.5 wt %, and the final pH is less than about 1.5, when the consistency is between about 15 wt % and about 40 wt %.

Example 12: Demonstration of Effective $SO_2$ Concentration and Dosage by Varying $SO_2$ Dosage and Straw The advantages of an appropriate effective $SO_2$ concentration (e.g., in slurry) and dosage (e.g., on solids) has been demonstrated for both leached and as-is feedstock (i.e., leached and as-is wheat straw, respectively), for various $SO_2$ dosages.

The $SO_2$ pretreatment was conducted as $SO_2$ catalyzed batch pretreatment in laboratory tubular reactors having a volume of 25 mL. The reactors were formed from a stainless steel tube (i.e., about 5 inches in length and about 9/16 inch internal diameter). Each end of each tube was secured with a hex Swagelok fitting and cap.

The wheat straw was hammer-milled to provide an average particle size of about ¼ inch (0.635 cm) and had a glucan content of 34.61% and a total solids (TS) content of 91.6 wt %, on a dry basis. The carbohydrate assay used to determine the glucan content was based on Determination of Structural Carbohydrates and Lignin in Biomass-LAP (Technical Report NREL/TP-510-42618).

To prepare the leached wheat straw samples for pretreatment, about 100 g of the hammer-milled wheat straw (e.g., having an average particle size of about ¼ inch (0.635 cm)) was soaked in ultra-purified water (Milli-Q™) in an approximately 18:1 (v/v) water to straw ratio for about 1 hour and 20 minutes, was filtered through glass fiber filter paper, was washed with about 1-2 L of additional ultra-purified water (Milli-Q™), and was then filtered again. The washing and filtering steps were repeated. The leached straw was spread out evenly and air dried to a total solids (TS) content of 94.9 wt % and had a glucan content of 36.1% on a dry basis. The carbohydrate assay used to determine the glucan content was based on Determination of Structural Carbohydrates and Lignin in Biomass-LAP (Technical Report NREL/TP-510-42618).

To prepare the as-is wheat straw samples for pretreatment, the hammer-milled wheat straw (e.g., having an average particle size of about ¼ inch (0.635 cm)) was used as-is (e.g., having a glucan content of 34.61% and a total solids (TS) content of 91.6 wt %, on a dry basis) without washing and/or leaching prior to pretreatment.

To prepare leached and as-is samples having a consistency of about 30 wt %, each tubular reactor was charged with approximately 1.64 g of accurately weighed wheat straw (i.e., corresponding to about 1.5 g, on a dry basis) and 3.35 mL of sulfurous acid solution (i.e., 1-6.5 wt % prepared from ≥6 wt % $H_2SO_3$, from Sigma-Aldrich, and assumed to have a density of 1.03 g/ml), and the reactor sealed.

Each tubular reactor was placed in a 26 L oil bath preheated to the pretreatment temperature (e.g., 210° C.), where it remained submerged for 1-10 minutes. At the end of each pretreatment, each tubular reactor was removed from the oil bath, suspended in air for 10 seconds to allow oil to drip from the sides, and placed into an ice bath to cool.

A total of three pretreatments were conducted for the as-is samples (Runs 7-9) and a total of three pretreatments were conducted for the leached samples (Runs 10-12). As indicated above, the runs varied in both time and amount of sulfur dioxide present. The pretreatment conditions/parameters for all 6 runs are summarized in Tables 3 and 4. For runs 7 and 10, the target initial pH was about 1.15, for runs 8 and 11 the target initial pH was about 1.25-1.3, and for runs 9 and 12, the target initial pH was about 1.7. Notably, although runs 3 and 6 share a common target initial pH, the sulfur dioxide dosage is different for these runs (e.g., since the leaching process may remove buffering agents that may affect the pH at these low $SO_2$ concentrations). The sulfur dioxide dosage, $SO_{2(Total,dry)}$, sulfur dioxide slurry concentration, $SO_{2(Total,wet)}$, and volume of the slurry, $V_s$ were calculated using Eqs. 16, 17, and 18, respectively. The concentration of xylose and furfural from each reactor was measured according to Example 6, and compared to the initial xylan concentration, measured according to Example 10, to provide $C/C_o$. The final pH of the pretreated slurry was measured at ambient temperature. These pretreatment results are also shown in Tables 3 and 4. The operating points are shown in FIG. 11.

TABLE 3

Pretreatment of as-is wheat straw having a consistency of about 30%

| Run | Temperature (° C.) | Time (min) | $H_2SO_3$ in liquid (wt %) | $V_s/V_r$ | $SO_{2(VA,dry)}$ (wt %) | $SO_{2(VA,wet)}$ (wt %) | $C/C_0$ Xylose (%) | $C/C_0$ Furfural (%) | Final pH |
|---|---|---|---|---|---|---|---|---|---|
| 7 | 210 | 3.75 | 6 | 0.204 | 2.19 | 0.94 | 81.6 | 11.5 | 0.89 |
| 8 | 210 | 4.75 | 4 | 0.204 | 1.46 | 0.62 | 80.7 | 15.7 | 0.96 |
| 9 | 210 | 5 | 2 | 0.204 | 0.73 | 0.31 | 67.7 | 6.17 | 1.01 |

TABLE 4

Pretreatment of leached wheat straw having a consistency of about 30%

| Run | Temperature (° C.) | Time (min) | $H_2SO_3$ in liquid (wt %) | $V_s/V_r$ | $SO_{2(VA,dry)}$ (wt %) | $SO_{2(VA,wet)}$ (wt %) | $C/C_0$ Xylose (%) | $C/C_0$ Furfural (%) | Final pH |
|---|---|---|---|---|---|---|---|---|---|
| 10 | 210 | 4 | 6 | 0.204 | 2.19 | 0.94 | 78.5 | 17.5 | 1.01 |
| 11 | 210 | 4.5 | 4 | 0.204 | 1.46 | 0.62 | 78.4 | 11.4 | 1.06 |
| 12 | 210 | 6 | 1 | 0.204 | 0.36 | 0.16 | 55.8 | 12.5 | 1.25 |

Figure 12:
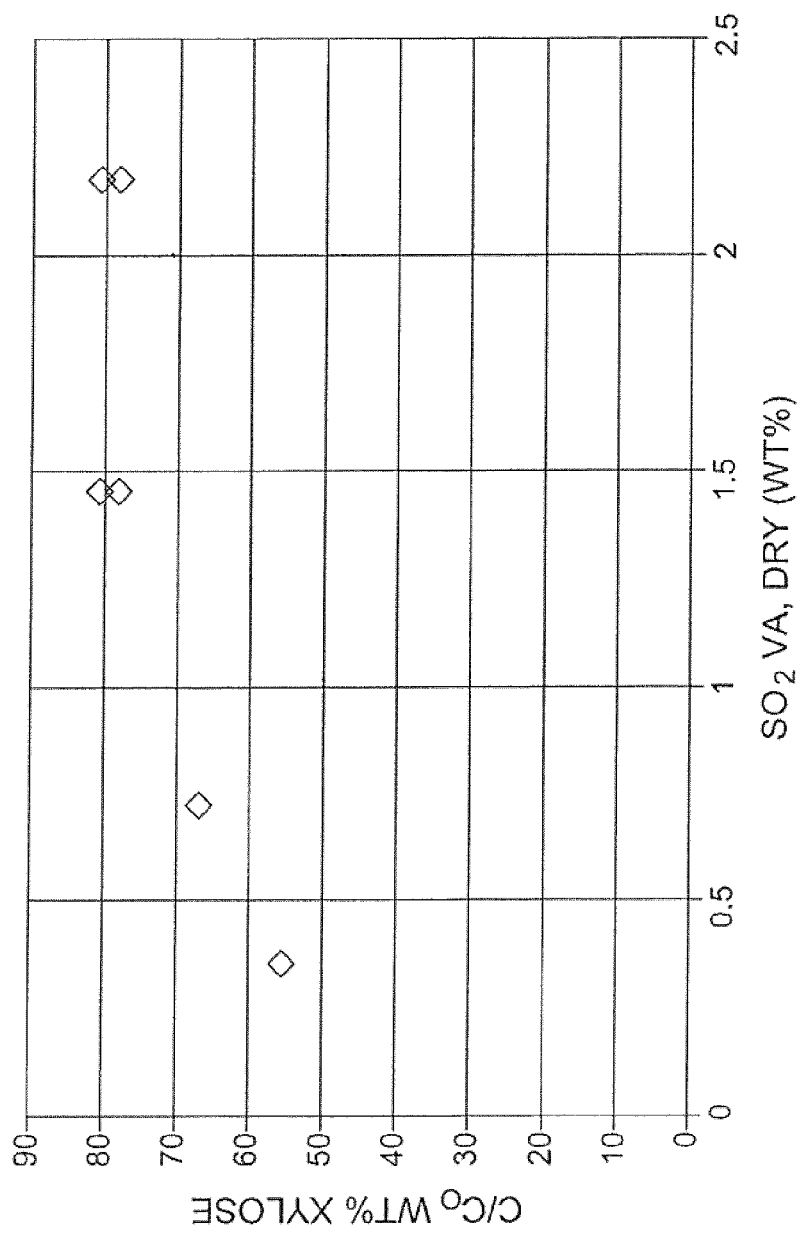
FIG. 12 is a plot illustrating xylose and furfural concentration (e.g., a weight percentage calculated with respect to initial xylan present) produced as a function of $SO_{2(VA,dry)}$ for slurries having various sulfur dioxide dosages.

The xylose concentrations illustrated in Tables 3 and 4 are plotted in FIG. 12, for the different effective sulfur dioxide dosages. Referring also to FIG. 12, the xylose yield appears to be greater than about 70%, which may indicate good performance, when the effective sulfur dioxide dosage, $SO_{2(VA, dry)}$, is greater than about 0.8 wt % (e.g., and $SO_{2(VA, wet)}$ is greater than about 0.4 wt %), and is lower than 70% for runs 9 and 12 wherein the effective sulfur dioxide dosage, $SO_{2(VA, dry)}$ is 0.77 wt % and 0.36 wt %, respectively. These operating points are shown in FIG. 11 as the two data points below the 1.0 wt % effective $SO_2$ dosage limit. Even greater xylose yields (e.g., greater than about 75%) are found when effective sulfur dioxide dosage, $SO_{2(VA, dry)}$ is greater than about 1 wt %.

The advantages of an appropriate effective $SO_2$ concentration (e.g., in slurry) and dosage (e.g., on solids) has been demonstrated for different temperatures at various $SO_2$ dosages. For example, referring to Table 5, as-is samples prepared as per Runs 8 and 9 were pretreated at 190° C. for 8 minutes and 7.5 minutes.

TABLE 5

Pretreatment of as-is wheat straw having a consistency of about 30%

| Run | Temperature (° C.) | Time (min) | $H_2SO_3$ in liquid (wt %) | $V_s/V_r$ | $SO_{2(VA,dry)}$ (wt %) | $SO_{2(VA,wet)}$ (wt %) | $C/C_0$ Xylose (%) | $C/C_0$ Furfural (%) |
|---|---|---|---|---|---|---|---|---|
| 13 | 190 | 8 | 4 | 0.204 | 1.46 | 0.62 | 78.2 | 10.5 |
| 14 | 190 | 7.5 | 2 | 0.204 | 0.73 | 0.31 | 78.9 | 9.76 |

Example 13: Demonstration of Effective SO$_2$ Concentration and Dosage with Steam Gun The advantages of an appropriate effective SO$_2$ concentration (e.g., in slurry) and dosage (e.g., on solids) has been also demonstrated for wheat straw using SO$_2$ in a 58.7 L steam gun.

The wheat straw was hammer-milled to provide an average particle size of about ¼ inch (0.635 cm) and had a glucan content of 34.61% and a total solids (TS) content of 91.6 wt %, on a dry basis. The carbohydrate assay used to determine the glucan content was based on Determination of Structural Carbohydrates and Lignin in Biomass-LAP (Technical Report NREL/TP-510-42618).

To prepare the wheat straw samples for pretreatment, the hammer-milled wheat straw (e.g., having an average particle size of about ¼ inch (0.635 cm)) was sprayed with water using a garden sprayer, in an amount to achieve the desired consistency (e.g., which was determined using the weight of the feedstock before and after spraying).

The steam gun, which was operated in batch mode, was pre-heated by rapidly adding steam to heat the reactor to the desired temperature, followed by a depressurization. This cycle was repeated a total of three times. For each run, a weighed amount of water-sprayed wheat straw (e.g., corresponding to approximately 240-250 g dry mass), was placed within a 100 mesh wire mesh bag, which was supported in a wire basket within the preheated steam gun. The steam gun was sealed and gaseous SO$_2$ was added to the steam gun to provide a target SO$_2$ dosage. The amount of SO$_2$ added was determined from the before and after mass of the SO$_2$ cylinder. After the SO$_2$ was added, steam was added rapidly until the desired pressure (e.g., and thus desired temperature) was reached. In general, the steam was added within 1 minute after the SO$_2$ was added. The reported cooking times began as soon as the steam valve was opened, and thus includes the temperature ramp up time (e.g., ~80 seconds). After the desired cooking time, the pressure in the steam gun was reduced quickly (e.g., to less than 5 psig). After 7 cycles of repressuring the steam gun to about 50 psig with air followed by a rapid depressurization, the pretreated material was removed from the steam gun. These air flushes were conducted to decrease the sulfur dioxide concentration within the pretreated slurry to safe levels. Gaseous emissions from the pressure reductions were collected and/or treated in an environmental control unit. The final pH of the pretreated material was measured after the final flashing/depressurization.

The general steam gun equipment and conditions are described in U.S. Pat. No. 4,461,648 (Foody), which is hereby incorporated by reference. The steam gun pretreatment system was configured for SO$_2$ use. In particular, it was provided with an SO$_2$ inlet coupled to a SO$_2$ canister and appropriate safety systems.

The pretreatment conditions/parameters for the different runs (i.e., Runs 15-21) at 195° C. are summarized in Table 6.

TABLE 6

SO$_2$ Catalyzed Pretreatment of as-is wheat straw in a steam gun

| Run | Consistency (wt %) | Mass of slurry (g) | Time (min) | $V_s/V_r$ | $SO_{2(VA,dry)}$ (wt %) | $SO_{2(VA,wet)}$ (wt %) | $C/C_0$ Xylose (%) | $C/C_0$ Furfural (%) | Final pH |
|---|---|---|---|---|---|---|---|---|---|
| 15 | 34.6 | 685 | 2.87 | 0.012 | 2.00 | 1.01 | 78.3 | 1.49 | 1.22 |
| 16 | 40.88 | 600 | 2.87 | 0.010 | 1.73 | 1.20 | 81.68 | 1.34 | 1.14 |
| 17 | 50.3 | 480 | 2.86 | 0.008 | 1.38 | 1.40 | 76.90 | 1.65 | 1.00 |
| 18 | 61.5 | 400 | 2.88 | 0.007 | 1.16 | 1.86 | 49.13 | 1.08 | 1.69 |
| 19 | 61.5 | 400 | 3.91 | 0.006 | 0.96 | 2.64 | 57.77 | 2.82 | 1.28 |
| 20 | 73.3 | 343 | 3.85 | 0.006 | 0.93 | 2.56 | 45.37 | 2.94 | 0.86 |
| 21 | 50.3 | 480 | 4.06 | 0.008 | 0.93 | 0.94 | 74.12 | 1.74 | 1.18 |

Referring to Table 6, the amount of xylose produced is greater than 70% for consistencies up to 50.3%. At consistencies of 61.5 wt % or greater, the amount of xylose produced is shown to be less than 70 wt %, and thus may be associated with a less effective hydrolysis.

Figure 13:
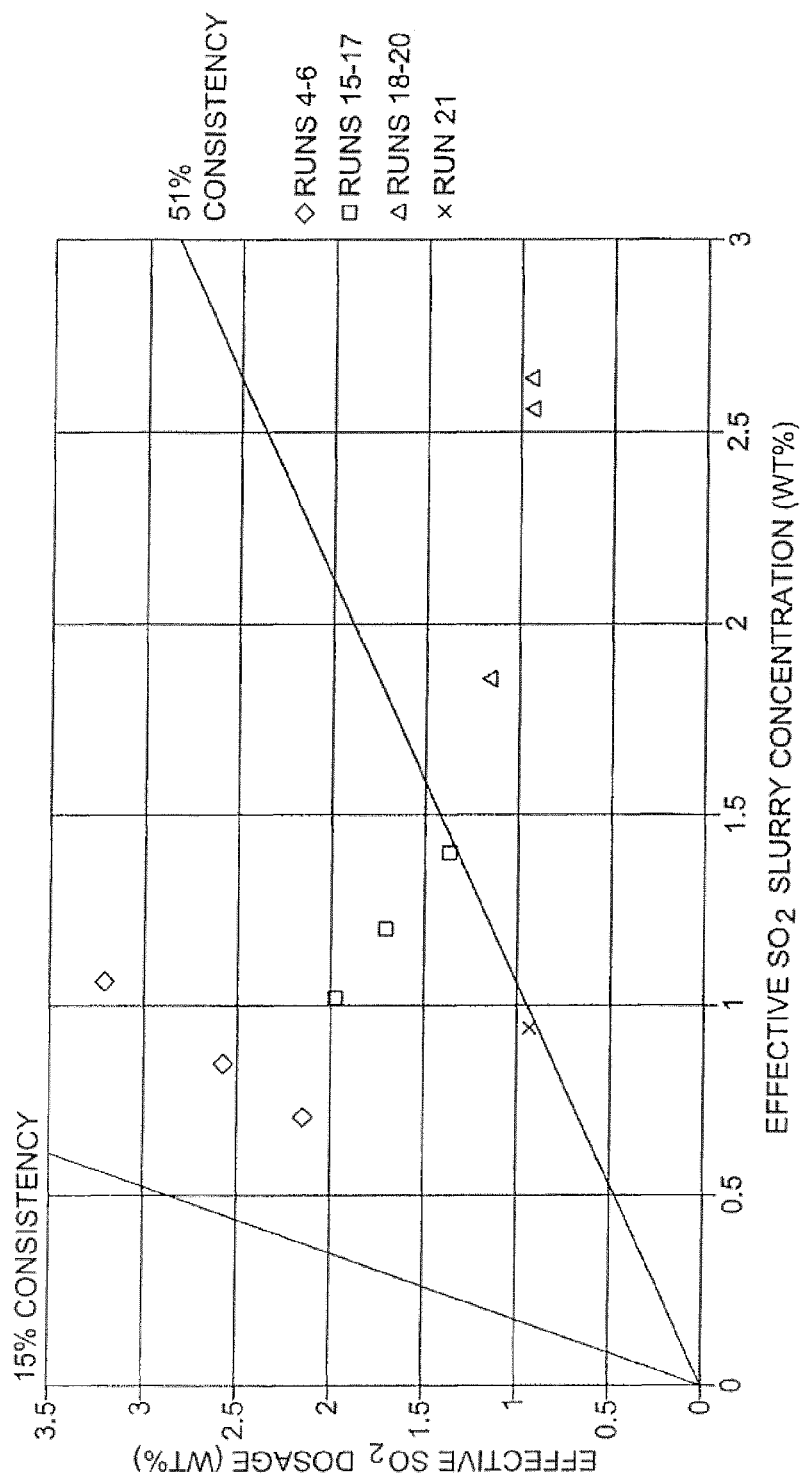
FIG. 13 is a plot of a graph illustrating the volume adjusted total amount of sulfur dioxide available as a function of dry lignocellulosic biomass and moisture for various runs.

The sulfur dioxide dosage, $SO_{2(Total,dry)}$, sulfur dioxide slurry concentration, $SO_{2(Total,wet)}$, and volume of the slurry, $V_s$, were calculated using Eqs. 16, 17, and 18, respectively. The mass of the slurry was calculated from the dry mass added and the consistency. The concentration of xylose and furfural from each reactor was measured according to Example 6, and compared to the initial xylan concentration, measured according to Example 10, to provide $C/C_o$. The operating points are shown in FIG. 13. Data points from runs 4-6 are shown for comparison.

Advantageously, the results illustrated in the Tables and FIGS. 2, 11, and 13 indicate that selecting the appropriate pretreatment conditions/parameters (e.g., sulfur dioxide dosage) in dependence upon $V_s/V_r$ may improve pretreatment. In one embodiment, the pretreatment conditions are selected such that the consistency of the lignocellulosic biomass is between 14.5 wt % and 40.5 wt % and the effective SO$_2$ dosage, $SO_{2(VA, dry)}$, is equal to or greater than 0.8 wt %. In this embodiment, plotting $SO_{2(VA, dry)}$ as a function of $SO_{2(VA, wet)}$ may provide a point within the preferred range illustrated in FIG. 2. In another embodiment, the pretreatment conditions are selected such that the consistency of the lignocellulosic biomass is between 14.5 wt % and 40.5 wt % and the effective SO$_2$ dosage, $SO_{2(VA, dry)}$, is equal to or greater than 1 wt %. In this embodiment, plotting $SO_{2(VA, dry)}$ as a function of $SO_{2(VA, wet)}$ may provide a point within the region between the dotted lines and above the solid line, of FIG. 11. In yet another embodiment, the pretreatment conditions are selected such that the consistency of the lignocellulosic biomass is within the preferred range of 14.5 wt % to 51 wt % and the effective SO$_2$ dosage, $SO_{2(VA, dry)}$, is equal to or greater than 0.8 wt % or 1.0 wt %. In this embodiment, plotting $SO_{2(VA, dry)}$ as a function of $SO_{2(VA, wet)}$ may provide a point within the consistency range illustrated in FIG. 13.

Of course, the above embodiments have been provided as examples only. It will be appreciated by those of ordinary skill in the art that various modifications, alternate configurations, and/or equivalents will be employed without departing from the spirit and scope of the invention. For example, in any of the above described embodiments, a controller configured for adjusting at least one of a flow of the acid, the slurry volume, $V_s$, and/or the consistency of the lignocellulosic feedstock fed to the pretreatment, may be included. Accordingly, the effective sulfur dioxide dosage and/or effective sulfur dioxide slurry concentration may be selected and/or adjusted with the controller to be within a predetermined range. In one embodiment the controller is automated (e.g., includes a processor and/or controlling circuit). In another embodiment, the controller is manually operated (e.g., includes a pressure gauge and/or valve). Accordingly, the scope of the invention is therefore intended to be limited solely by the scope of the appended claims.

The invention claimed is:

1. A method for pretreating and hydrolyzing lignocellulosic biomass comprising:
   a) adding acid to the lignocellulosic biomass to produce acidified lignocellulosic biomass, said acid comprising at least one of sulfur dioxide and sulfurous acid;
   b) pretreating the acidified lignocellulosic biomass in at least one pretreatment reactor to provide a pretreated slurry having a pH less than 1.5, said pretreated slurry comprising cellulose, said acidified lignocellulosic biomass having a consistency between 14.5 wt % and 51 wt %, said at least one pretreatment reactor comprising a first pretreatment reactor, said pretreating conducted at a temperature greater than 170° C. and under pretreating conditions wherein a product of sulfur dioxide dosage and $V_s/V_r$ is greater than 0.8 wt %, where $V_s/V_r$ is a ratio of slurry volume to reactor volume and where sulfur dioxide dosage is a ratio of grams of sulfur dioxide present in the first pretreatment reactor to grams of dry lignocellulosic biomass present in the first pretreatment reactor expressed as a weight percentage; and
   c) hydrolyzing the cellulose from the pretreated slurry with an enzyme to produce glucose.

2. The method according to claim 1, comprising reducing a pressure on the pretreated slurry to produce a flash stream and a cooled pretreated slurry.

3. The method according to claim 2, comprising recovering the acid from at least one of the flash stream and a stream derived from the flash stream.

4. The method according to claim 3, comprising recycling the recovered acid back into the at least one pretreatment reactor.

5. The method according to claim 1, wherein said acid is added to the lignocellulosic biomass in an amount sufficient to provide a sulfur dioxide dosage of at least 6 wt %.

6. The method according to claim 1, wherein said acid is added to the lignocellulosic biomass in an amount sufficient to provide a sulfur dioxide dosage of at least 15 wt %.

7. The method according to claim 1, wherein said acid is added to the lignocellulosic biomass in an amount sufficient to provide a sulfur dioxide dosage of at least 20 wt %.

8. The method according to claim 1, wherein step a) includes adding sulfur dioxide to the lignocellulosic biomass upstream of the first pretreatment reactor, to the first pretreatment reactor, or a combination thereof.

9. The method according to claim 1, wherein the enzyme comprises cellulase at a dosage of less than about 12 milligrams protein per gram of cellulose.

10. The method according to claim 1, wherein adding acid to the lignocellulosic biomass comprises adding an amount of sulfur dioxide sufficient to provide a pretreated slurry having a pH less than 1.25.

11. The method according to claim 3, wherein recovering the acid comprises collecting gaseous sulfur dioxide from the flash stream.

12. The method according to claim 1, wherein $V_s/V_r$ is less than 0.60.

13. The method according to claim 1, wherein $V_s/V_r$ is between 0.10 and 0.40.

14. The method according to claim 1, wherein the effective sulfur dioxide slurry concentration in the first pretreatment reactor is between 0.25 wt % and 1.5 wt %, said effective sulfur dioxide slurry concentration calculated from the product of the sulfur dioxide slurry concentration and $V_s/V_r$, said sulfur dioxide slurry concentration calculated from the ratio of grams of sulfur dioxide present to grams of moisture present expressed as a weight percentage.

15. The method according to claim 1, wherein the product of sulfur dioxide dosage and $V_s/V_r$ is greater than 1 wt %.

16. The method according to claim 1, wherein the product of sulfur dioxide dosage and $V_s/V_r$ is greater than 2 wt %.

17. The method according to claim 1, wherein the lignocellulosic biomass comprises a non-woody lignocellulosic biomass.

18. The method according to claim 1, wherein a residence time of the acidified lignocellulosic biomass in the first pretreatment reactor is between 30 seconds and 8 minutes, and wherein the first pretreatment reactor is held at a temperature between 180° C. and 240° C. for the residence time.

19. The method according to claim 1, wherein said pretreating comprises conducting a sulfur dioxide catalyzed steam explosion pretreatment.

20. A method for pretreating and hydrolyzing lignocellulosic biomass comprising:
   a) adding acid to the lignocellulosic biomass to produce acidified lignocellulosic biomass, said acid comprising at least one of sulfur dioxide and sulfurous acid;
   b) pretreating the acidified lignocellulosic biomass in at least one pretreatment reactor to provide a pretreated slurry, said pretreated slurry comprising cellulose and having a pH that is less than 1.55, said acidified lignocellulosic biomass having a consistency that is greater than 14.5 wt % and less than 50.5 wt %, said at least one pretreatment reactor comprising a first pretreatment reactor having a reactor volume $V_r$ and a slurry volume $V_s$; and
   c) hydrolyzing the cellulose with an enzyme to produce glucose,
   wherein adding the acid to the lignocellulosic biomass comprises adding an amount of the acid that provides an effective sulfur dioxide dosage that is greater than 1 wt % and an effective sulfur dioxide slurry concentration that is between 0.25 wt % and 1.5 wt %, said effective sulfur dioxide slurry concentration calculated from the product of the sulfur dioxide slurry concentration in the first pretreatment reactor and $V_s/V_r$, said sulfur dioxide slurry concentration calculated from the ratio of grams of sulfur dioxide present to grams of moisture present expressed as a weight percentage, said effective sulfur dioxide dosage calculated from the product of sulfur dioxide dosage in the first pretreatment reactor and $V_s/V_r$,
   and wherein said pretreating is conducted at a temperature greater than 170° C.

21. The method according to claim 20, wherein the effective sulfur dioxide dosage is greater than 1.5 wt %.

22. The method according to claim 20, wherein the effective sulfur dioxide dosage is greater than 2 wt %.

23. A method for pretreating and hydrolyzing lignocellulosic biomass comprising:
- a) adding acid to the lignocellulosic biomass to produce acidified lignocellulosic biomass, said acid comprising at least one of sulfur dioxide and sulfurous acid;
- b) pretreating the acidified lignocellulosic biomass in at least one pretreatment reactor to provide a pretreated slurry having a pH less than 1.5, said pretreated slurry comprising cellulose, said acidified lignocellulosic biomass having a consistency between 14.5 wt % and 40.5 wt %, said at least one pretreatment reactor comprising a first pretreatment reactor, said pretreating conducted at a temperature greater than 170° C. and under pretreating conditions wherein a product of sulfur dioxide loading and $V_s/V_r$ is greater than 0.8 wt %, where $V_s/V_r$ is a ratio of slurry volume to reactor volume and where sulfur dioxide loading is a ratio of grams of sulfur dioxide fed to the first pretreatment reactor to grams of dry lignocellulosic biomass fed to the first pretreatment reactor expressed as a weight percentage; and
- c) hydrolyzing the cellulose from the pretreated slurry with an enzyme to produce glucose, wherein said acid is added to the lignocellulosic biomass in an amount sufficient to provide a sulfur dioxide loading of at least 20 wt %.

* * * * *

UNITED STATES PATENT AND TRADEMARK OFFICE
CERTIFICATE OF CORRECTION

PATENT NO. : 10,662,455 B2
APPLICATION NO. : 16/061254
DATED : May 26, 2020
INVENTOR(S) : Jeffrey S. Tolan Page 1 of 2

It is certified that error appears in the above-identified patent and that said Letters Patent is hereby corrected as shown below:

On the Title Page

On Page 2, Column 2, Item (56), Line 58, Other Publications, delete "Fractionism" and insert --Fractionation--.

On Page 3, Column 1, Item (56), Line 10, Other Publications, delete "Bioresouces," and insert --Bioresources,--.

On Page 3, Column 1, Item (56), Line 15, Other Publications, delete "Apita," and insert --Appita,--.

In the Drawings

On Sheet 2 of 12, FIG. 2, Y-Axis, Line 1, delete "S0$_2$" and insert --SO$_2$--.

On Sheet 2 of 12, FIG. 2, Line 8, delete "S0$_2$" and insert --SO$_2$--.

On Sheet 2 of 12, FIG. 2, X-Axis, Line 11 (Approx.), delete "S0$_2$" and insert --SO$_2$--.

In the Specification

In Column 2, Line 65, delete "(V$_S$))" and insert --(V$_S$)--.

In Column 6, Line 47, delete "invention" and insert --invention;--.

In Column 7, Line 47, delete "Retelling" and insert --Referring--.

In Column 20, Line 47 (Approx.), delete "SO$_{2(Totat,dry)}$" and insert --SO$_{2(Total,dry)}$--.

In Column 23, Line 33, delete "SO$_{2(7A,dry)}$" and insert --SO$_{2(VA,dry)}$--.

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,662,455 B2

In Column 24, Line 25, delete "$V_{s\,to}$ Vr." and insert --$V_s$ to $V_r$.--.

In Column 25, Line 14 (Approx.), delete "and or" and insert --and/or--.

In Column 26, Line 39, delete "Cf" and insert --$C_f$--.

In Column 31, Line 7 (Approx.), delete "and or" and insert --and/or--.

In Column 34, Line 29, delete "and or" and insert --and/or--.

In Column 41, Line 58, delete "digestability" and insert --digestibility--.

In Column 44, Line 11 (Approx.), delete "(>6% $H_2SO_3$," and insert --(≥6% $H_2SO_3$,--.

In Column 47, Line 46, delete "25" and insert --25 μL.--.

In Column 49, Line 64, delete "gL)," and insert --g/L),--.

In Column 54, Line 16 (Approx.), delete "g biomass added* TS content" and insert --g moisture--.

In Column 57, Line 4, delete "$V_s$." and insert --$V_s$,--.